Figure 1:
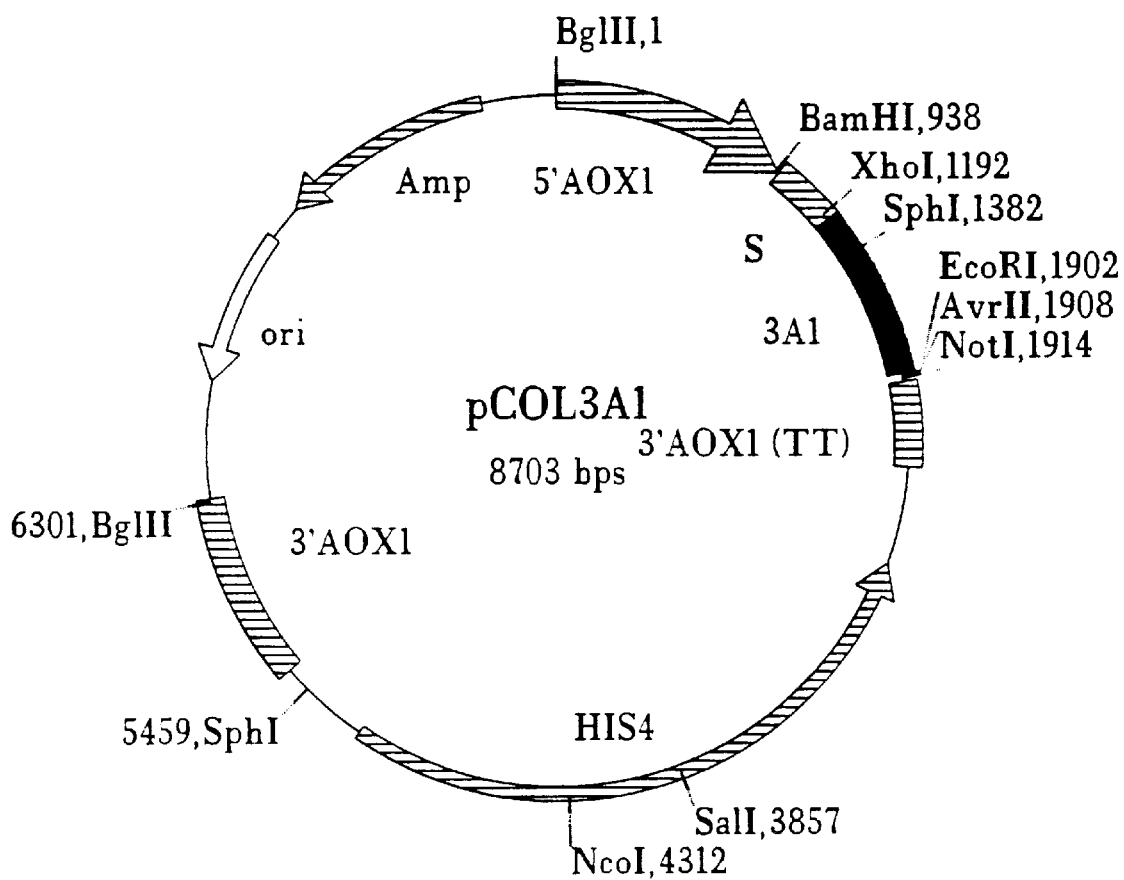

United States Patent
Van Heerde et al.

[11] Patent Number: 6,150,081
[45] Date of Patent: Nov. 21, 2000

[54] SILVER HALIDE EMULSIONS WITH RECOMBINANT COLLAGEN SUITABLE FOR PHOTOGRAPHIC APPLICATION AND ALSO THE PREPARATION THEREOF

[75] Inventors: George Valentino Van Heerde, Oosterhout; Alexis Cornelus Van Rijn, Rosmalen; Jan Bastiaan Bouwstra, Bilthoven; Frederik Anton De Wolf, Bunnik; Andreas Mooibroek, Renkum; Marc Willem Theodoor Werten; Richèle Deodata Wind, both of Wageningen; Tanja Jacoba Van Den Bosch, Zeist, all of Netherlands

[73] Assignee: Fuji Photo Film B.V., Tilburg, Netherlands

[21] Appl. No.: 09/219,849

[22] Filed: Dec. 23, 1998

[30] Foreign Application Priority Data

Dec. 24, 1997 [NL] Netherlands ............... 1007908

[51] Int. Cl.[7] .................................. G03C 1/047
[52] U.S. Cl. ........................... 430/569; 430/628
[58] Field of Search ...................... 430/569, 628

[56] References Cited

U.S. PATENT DOCUMENTS

| | | | |
|---|---|---|---|
| 5,380,642 | 1/1995 | Roberts et al. ................. | 430/569 |
| 5,385,819 | 1/1995 | Bowman et al. ................ | 430/569 |
| 5,580,712 | 12/1996 | Keevert, Jr. et al. ............ | 430/569 |
| 5,670,616 | 9/1997 | Weber et al. .................... | 530/300 |
| 5,795,707 | 8/1998 | Wagner et al. .................. | 430/569 |

FOREIGN PATENT DOCUMENTS

| | | |
|---|---|---|
| 2685347 | of 0000 | France . |
| 93/07889 | of 0000 | WIPO . |
| 93/10154 | of 0000 | WIPO . |
| 97/14431 | of 0000 | WIPO . |
| 97/38710 | of 0000 | WIPO . |

*Primary Examiner*—Hoa Van Le
*Attorney, Agent, or Firm*—Nixon and Vanderhye PC

[57] ABSTRACT

A tabular silver halide emulsion wherein the tabular grains account for more than 75% of the total grain projected area said emulsion comprising silver halide grains nucleated in the presence of nucleation peptizer and thereafter grown in the presence of growth peptizer, wherein at least one of the peptizers is substantially pure collagen like material prepared by genetic engineering, said peptizer having an amino acid sequence comprising more than 4 different amino acids. A process of preparing the AgX emulsion. A process of producing recombinant collagen like polypeptide comprising expression of a collagen like polypeptide encoding nucleic acid sequence by a microorganism to a degree exceeding 0.95 grammes/liter, said recombinant collagen being free of helix structure and preferably the expression occurring in a microorganism other than *E. coli* or *Saccharomyces cerevisiae*.

82 Claims, 13 Drawing Sheets

Fig 2

5'AOX1: 5'-GACTGGTTCCAATTGACAAGC-3'

3'AOX1: 5'-GCAAATGGCATTCTGACATCC-3'

αMF: 5'-TACTATTGCCAGCATTGCTGC-3'

Fig 3

1 YGNSGSPGNP GVAGPKGDAG QPGEKGPPGA OGPPGSPGPL GIAGLTGARG LAGPPGMPGP

61 RGSPGPQGIK GESGKPGASG HNGERGPPGP QGLPGQPGTA GEPGRDGNPG SDGQPGRDGS

121 PGGKGDRGEN GSPGAPGAPG HPGPPGPVGP SGKNGDRGET GPAGPSGAPG PAGARGAPGP

181 QGPRGDKGET GERGSNGIKG HRGFPGNPGP PGSPGAAGHQ GAVGSPGP

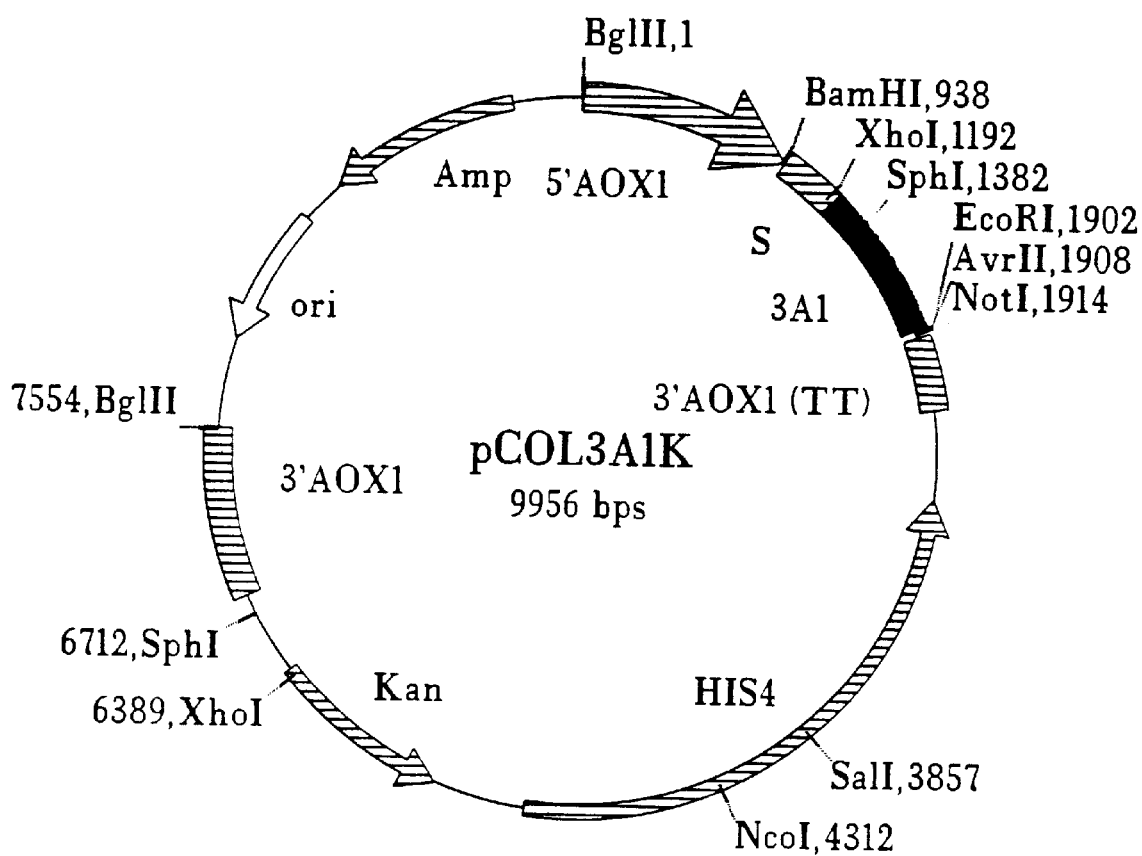

Fig 5

```
C1A1-FW  : 5'-CTTCCCAGATGTCCTATGGCTATGATG-3'
C1A1-RV1 : 5'-CCGCTCGAGGCTCGCCAGGAGGTCCAGGCAG-3'
C1A1-RV2 : 5'-GCGCTCGAGGGGAGGACCAATGGACCAGTCAG-3'
C1A1-RV3 : 5'-GCGCTCGAGGCCAGGAGAACCAGGAGGACCCTG-3'
```

```
N-X-FW : 5'-TCGAAAAGAGAGAGGCTGAAGCTCCCATGGGATAACTCGAGTAGG-3'
N-X-RV : 5'-AATTCCTACTCGAGTTATCCCATGGGAGCTTCAGCCTCTCTTT-3'
```

```
5'-TCGAAAAGAGAGAGGCTGAAGCTCCCATGGGATAACTCGAGTAGG    -3'
3'-    TTTCTCTCTCCGACTTCGAGGGTACCCTATTGAGCTCATCCTTAA-5'
```

Fig 8

```
  1  PMGPSGPRGL PGPPGAPGPQ GFQGPPGEPG EPGGSGPMGP RGPPGPPGKN GDDGEAGKPG
 61  RPGERGPPGP QGARGLPGTA GLPGMKGHRG FSGLDGAKGD AGPAGPKGEP GSPGENGAPG
121  QMGPRGLPGE RGRPGPPGTA GARGNDGAVG AAGPPGPTGP TGPPGFPGAV GAKGEAGPQG
181  ARGSEGPQGV RGEPGPPGPA GAAGPAGNPG ADGQPGAKGA NGAPGIAGAP GFPGARGPSG
241  PQGPSGPPGP KGNSGEPGAP GNKGDTGAKG EPGATGVQGP PGPAGEEGKR GARGEPGPSG
301  LPGPPGERLE
```

Fig 10

```
  1  PMGPSGPRGL PGPPGAPGPQ GFQGPPGEPG EPGGSGPMGP RGPPGPPGKN GDDGEAGKPG
 61  RPGERGPPGP QGARGLPGTA GLPGMKGHRG FSGLDGAKGD AGPAGPKGEP GSPGENGAPG
121  QMGPRGLPGE RGRPGPPGTA GARGNDGAVG AAGPPGPTGP TGPPGFPGAV GAKGEAGPQG
181  ARGSEGPQGV RGEPGPPGPA GAAGPAGNPG ADGQPGAKGA NGAPGIAGAP GFPGARGPSG
241  PQGPSGPPGP KGNSGEPGAP GNKGDTGAKG EPGATGVQGP PGPAGEEGKR GARGEPGPSG
301  LPGPPGERGG PGSRGFPGAD GVAGPKGPSG ERGAPGPAGP KGSPGEAGRP GEAGLPGAKG
361  LTGSPGSPGP DGKTGPPGPA GQDGRPGPAG PPGARGQAGV MGFPGPKGTA GEPGKAGERG
421  LPGPPGAVGP AGKDGEAGAQ GAPGPAGPAG ERGEQGPAGS PGFQGLPGPA GPPGEAGKPG
481  EQGVPGDLGA PGPSGARGER GFPGERGVQG PPGPAGPRGN NGAPGNDGAK GDTGAPGAPG
541  SQGAPGLQGM PGERGAAGLP GPKGDRGDAG PKGADGSPGK DGARGLTGPI GPPLE
```

Fig 12

```
  1  PMGPSGPRGL PGPPGAPGPQ GFQGPPGEPG EPGGSGPMGP RGPPGPPGKN GDDGEAGKPG
 61  RPGERGPPGP QGARGLPGTA GLPGMKGHRG FSGLDGAKGD AGPAGPKGEP GSPGENGAPG
121  QMGPRGLPGE RGRPGPPGTA GARGNDGAVG AAGPPGPTGP TGPPGFPGAV GAKGEAGPQG
181  ARGSEGPQGV RGEPGPPGPA GAAGPAGNPG ADGQPGAKGA NGAPGIAGAP GFPGARGPSG
241  PQGPSGPPGP KGNSGEPGAP GNKGDTGAKG EPGATGVQGP PGPAGEEGKR GARGEPGPSG
301  LPGPPGERGG PGSRGFPGAD GVAGPKGPSG ERGAPGPAGP KGSPGEAGRP GEAGLPGAKG
361  LTGSPGSPGP DGKTGPPGPA GQDGRPGPAG PPGARGQAGV MGFPGPKGTA GEPGKAGERG
421  LPGPPGAVGP AGKDGEAGAQ GAPGPAGPAG ERGEQGPAGS PGFQGLPGPA GPPGEAGKPG
481  EQGVPGDLGA PGPSGARGER GFPGERGVQG PPGPAGPRGN NGAPGNDGAK GDTGAPGAPG
541  SQGAPGLQGM PGERGAAGLP GPKGDRGDAG PKGADGSPGK DGARGLTGPI GPPGPAGAPG
601  DKGEAGPSGP PGPTGARGAP GDRGEAGPPG PAGFAGPPGA DGQPGAKGEP GDTGVKGDAG
661  PPGPAGPAGP PGPIGNVGAP GPKGPRGAAG PPGATGFPGA AGRVGPPGPS GNAGPPGPPG
721  PVGKEGGKGP RGETGPAGRP GEVGPPGPPG PAGEKGSPGA DGPAGSPGTP GPQGIAGQRG
781  VVGLPGQRGE RGFPGLPGPS GEPGKQGPSG SSGERGPPGP MG
```

Fig 13

```
  1  PMGPSGPRGL PGPPGAPGPQ GFQGPPGEPG EPGGSGPMGP RGPPGPPGKN GDDGEAGKPG
 61  RPGERGPPGP QGARGLPGTA GLPGMKGHRG FSGLDGAKGD AGPAGPKGEP GSPGENGAPG
121  QMGPRGLPGE RGRPGPPGTA GARGNDGAVG AAGPPGPTGP TGPPGFPGAV GAKGEAGPQG
181  ARGSEGPQGV RGEPGPPGPA GAAGPAGNPG ADGQPGAKGA NGAPGIAGAP GFPGARGPSG
241  PQGPSGPPGP KGNSGEPGAP GNKGDTGAKG EPGATGVQGP PGPAGEEGKR GARGEPGPSG
301  LPGPPGERGG PGSRGFPGAD GVAGPKGPSG ERGAPGPAGP KGSPGEAGRP GEAGLPGAKG
361  LTGSPGSPGP DGKTGPPGPA GQDGRPGPAG PPGARGQAGV MGFPGPKGTA GEPGKAGERG
421  LPGPPGAVGP AGKDGEAGAQ GAPGPAGPAG ERGEQGPAGS PGFQGLPGPA GPPGEAGKPG
481  EQGVPGDLGA PGPSGARGER GFPGERGVQG PPGPAGPRGN NGAPGNDGAK GDTGAPGAPG
541  SQGAPGLQGM PGERGAAGLP GPKGDRGDAG PKGADGSPGK DGARGLTGPI GPPLE
```

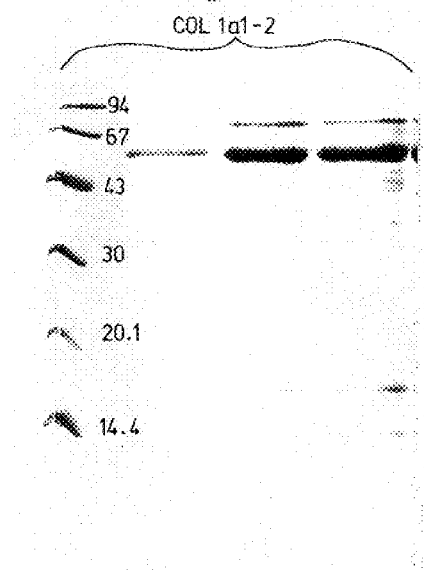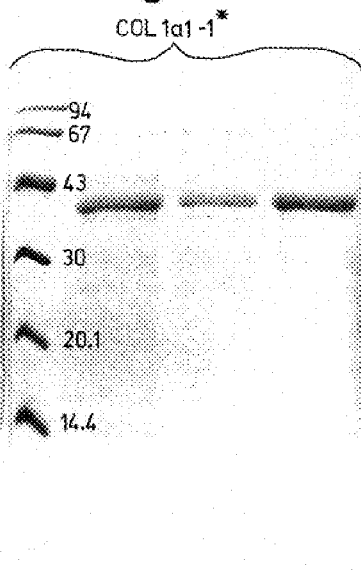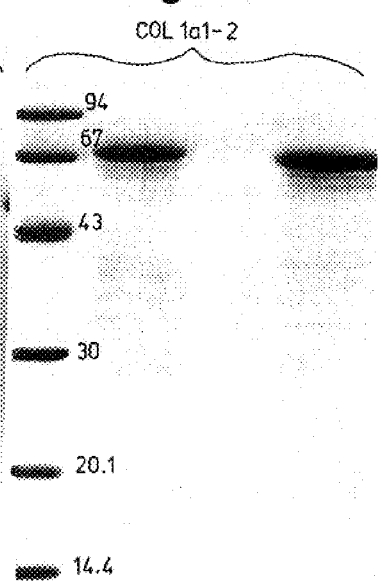

SILVER HALIDE EMULSIONS WITH RECOMBINANT COLLAGEN SUITABLE FOR PHOTOGRAPHIC APPLICATION AND ALSO THE PREPARATION THEREOF

SUMMARY OF THE INVENTION

The subject invention is directed at improved photographic products and improved methods of production of said products. In particular the improvement is arrived at through use of recombinant DNA technology in production of a component of a photographic product. The component of interest is collagen.

BACKGROUND OF THE INVENTION

The process of photographic product making is a complex procedure about which a lot has been disclosed and patented. In general terms the process to manufacture a photographic product like a photographic paper or triacetate cellulose film consists of coating several layers on top of either a laminated paper or a transparent polymer support. These layers are known as emulsion layers which can contain the radiation sensitive silver halide crystals as the most essential component or intermediate layers without these photosensitive components. The subject invention is directed at improving the photosensitive layer as such and improving the production process of photographic layers.

There are several stages at which gelatin is used in the process of film making. The function of the gelatin is different in each stage and thus the required characteristics for each stage are different and it is to be expected that collagen like substances can be specifically tailored to suit each particular application.

A lot of attention has been focussed on the process of making silver halide emulsions for photographic applications. A lot of attention has been paid to the role of grain morphology of silver halide crystals and aspects that influence the AgX nucleation process and the subsequent ripening process. The most essential component in an emulsion layer of a photographic product consists of radiation sensitive silver bromide, silver chloride or silver bromochloride microcrystals optionally containing iodide which are commonly referred to as silver halide grains. A peptizer is introduced during the precipitation of the grains to avoid uncontrolled coalescence which coalescence will otherwise exhibit a number of disadvantages i.a. limit the formation of thin intermediate and high aspect ratio tabular grain emulsions which in turn is disadvantageous in photography. Gelatin in numerous forms has been used in photographic manufacturing processes as peptizer. It is well known that the tabular grains with high aspect ratio have several photographic advantages like increased sharpness, improved speed granularity relationships, increased blue and minus blue speed separation, more rapid developability and higher silver covering power (Research Disclosure Vol. 225 January 1983, Item 22534; EP-A-0.610.796). It has also been desired to produce tabular grains not only with high aspect ratio but also with a narrow grain size distribution otherwise expressed as a desire for mono or homodispersity.

To date the gelatin used in commercial processes has been derived from animal sources in general simply by derival from animal bone and hide. The disadvantages of this material are the presence of impurities and the fact that the nature of the composition is unclearly defined and thus not reproducible. It is unclear what components are present and in which amounts. In addition it is also unclear which components actually are required for optimal activity. The reproducibility of the photographic manufacturing process is questionable due to the lack of consistency of the gelatin composition used at various stages of the photographic manufacturing process.

The disadvantages of gelatin in photographic applications have been addressed in detail over the years and have been the subject of various patent applications. Most of these documents have been directed at addressing processes of developing modified gelatins after the derival thereof from the animal source to introduce particular improvements in characteristics of the modified gelatins. In 1984 U.S. Pat. No. 4,439,520 describes a desirability for more than 50% of the crystals to have aspect ratios higher than 8 as this would increase blue speed. In 1987 U.S. Pat. No. 4,713,320 mentions using gelatin with a methionine content below 30 micromoles per gram, preferably less than 5 micromoles per gram to arrive at thin trapezoidal, hexagonal and triangular tabular grains. A normal bone derived gelatin was used which had been oxidized in order to achieve a level of methionine below 30 micromoles per gram of gelatin. The lower methionine content is also described in U.S. Pat. No. 4,914,014 in 1990 as offering a wider range of pBr during precipitation conditions. Numerous publications cover processes for reducing the methionine content of gelatin. EP-558.410 published in 1993 describes oxidizing reagent reaction of alkali hypochlorite or $H_2O_2$ as do articles in J.Photo.Sci 40 230—230 (Nippi), J.Photo.Sci 37, 14–18 (AGFA) of 1992 and J.Imag.Sci 33,1 3–17 of 1989. Even as early as 1959 oxidation was suggested as a manner to remove impurities.

There has also been a lot of research carried out on collagen and collagen like proteins per se using recombinant nucleic acid technology. The use of recombinant DNA technology in combination with collagen and the application thereof in photographic application has however been remarkably absent. Most of the documents published in the area of recombinant collagen have been directed at diagnostic applications using PCR technology on genomic nucleic acid not even requiring expression of the collagen encoding sequence. The mere presence of the sequence in the genome suffices for diagnosis in these instances. Any such documents actually mentioning expression of collagen encoding sequences certainly have not required a high degree of expression. Alternatively where expression is mentioned merely portions of the encoding sequence are expressed rather than the complete sequence. Often these partial sequences are used for eliciting antibodies for which amounts of proteinaceous material required are minimal. In addition once the antibodies are obtained the sequences are not required further for pharmaceutical application. Therefore in these instances low expression is not a relevant issue. Also the expression of small portions of the encoding sequence can be expected to eliminate expression problems which are attributed to the high degree of repetitivity of the encoding sequence.

Synthetic nucleic acid has been designed in an effort to overcome expression problems associated with longer repetitive sequences and also in an effort to design new types of protein i.e. synthetic protein. Such synthetic polypeptides are however extremely expensive to produce. It is thus not feasible to apply such in applications requiring large scale production such as required in the field of photographic film production.

Most applications of the prior art thus either do not require the high degree of expression required for production on an industrial scale or do not in fact provide the desired result. The documents discussing these types of application have consequently either not addressed or have not solved the problem of obtaining high expression of native collagen sequences or sequences of corresponding length and structure.

In general where the prior art has suggested expressing native sequences or parts thereof general terms have been used and referrals to handbooks for general transformation protocols have been given without further detail. Any examples provided have used *E. coli* or *S. cerevisiae* as producing organism and degree of expression has been of minor importance or has not been focussed on.

Where expression problems of collagen like protein have been addressed this has occurred by using either modified *E. coli* or higher animal cells and insect cells. The latter are also modified for post translational processing. The application of the latter type of cells is however prohibitive for large scale production due to the high costs of the cells, the media and the isolation of product. The disadvantage of *E. coli* is that it cannot secrete the desired product. In addition the repetitivity of a nucleic acid sequence to be expressed will provide instability of the transformed bacterium and thus result in low expression levels for any collagen like encoding sequence. It is thus not feasible to apply such production (micro)organisms in applications requiring large scale production as required in the field of photographic film production.

A lot of research effort has been directed at achieving the post transcription modification required to arrive at fibrillar or triple helix collagen which is the state of collagen as present in animal sources i.e. the state of collagen currently applied in industrial scale photographic applications. It has been generally accepted that host cells comprising post translational processing apparatus as such themselves or through addition of encoding sequences for post translational processing enzymes should be used when expressing collagen like material in order to arrive at collagen with a triple helix and more particularly to arrive at fibrillar collagen. It is commonly accepted that this form of collagen is the useful form for application.

Where the prior art has actually tentatively actually suggested recombinant collagen could be used in photographic applications the relevance of the particular form of collagen material has usually not been addressed vis a vis the requirements specific for such application. Some patent applications have mentioned in passing the use of recombinant collagen for photographic film, some even specifically mention photographic application. The teachings of such documents are clearly however directed at other issues and are not directed specifically at photographic applications and the special requirements thereof. Closer analysis actually shows that for various reasons none of the examples provided in such applications are in fact even suited for application in photographic films. The patent applications are considered non enabling and merely speculative of nature when it comes to applying recombinant collagen in photographic manufacturing processes. Examples of such documents are now provided.

WO90/05177 describes the production of novel polymers comprising small repeating sequences, specifically repeating groups such as silk are disclosed. Collagen is suggested as one of the structures capable of providing a repeating unit. It is stated "The properties of CLP were designed so they would undergo thermoreversible gelation at high temperatures as well as being non immunogenic. The high stability of the helices should create high tensile strength in fibres or membranes formulated from CLP. "These chain properties should allow the creation of hydrogel colloids in aqueous solutions which when applied to hard substrates should act as soft coatings." A suggestion is then given of a soft coating material with a ligand for a cellular receptor. The sequence (SEQ ID NO: 1) GLPGPKGDRGDAGPKGADGSP was to be added to the CLP monomer and an example of a construct to be expressed from *E. coli* is provided. With regard to this composition it is disclosed. "The subject compositions may find use as wound dressings, allowing for neovascularisation, eye applications, matrices for artificial organs and the like." The combination of CLP with other repetitive functional units thereby combining functions is also suggested. However no examples are provided of sequences used.

The only examples provided show a recombinantly produced synthetic CLP polypeptide (SEQ ID NO: 2) [[GAP (GPP)3]2[GPVGSP]n with N-terminal and C terminal spacers. The spacers are 33 amino acids and 25 amino acids in length. Thus the repetitive GPP portion of the polymer which is 24 amino acids in length is separated by 33+25+6 amino acids. In this manner *E coli* apparently managed to express a CLP protein of 760 amino acids, i.e. MW 63.800. The cell binding CLP had the same basic structure but the hexamer was replaced by the cell binding sequence given above resulting in an amino acid length of 814 amino acids and a MW of 70.560. The repetitive GXY motif that is expressed is short and is separated by long none repetitive sequences. The spacer DNA encodes 2 cysteine residues and also 3 methionine residues.

The cited document states in the introductory part concerning collagen "Chemically hydrolysed natural collagen can be denatured and renatured by heating and cooling to produce gelatin which is used in photographic and medical applications among other applications. The chain property of collagen responsible for this phenomenon is its ability to spontaneously form interchain aggregates having a conformation designated as a triple helix." It is thus particularly remarked in this prior art document that helical structure was required. The subsequent text is actually silent on any photographic applications and is clearly directed at completely other matters. The subsequent text is also silent on actual degree of expression obtained by *E. coli*. The repetitive structure is present to such a low degree it is unlikely to retain sufficient collagen like activity to be useful in photographic application. In addition the presence of cysteine and methionine residues at the levels provided herein in the expression product in fact render such inappropriate for use in AgX emulsions for photographic applications. Furthermore it is unclear whether the use of the less repetitive sequences as described here actually provided any improved level of expression in *E. coli*. Thus a person skilled in the art of photographic applications would be dissuaded from applying the teaching of this document in photographic applications. Firstly because it is unclear whether industrial scale production would be feasible. Considering instability of repetitive sequences this is unlikely. Secondly it is unlikely due to the undesired presence of cysteine and methionine in AgX emulsions for photographic applications. Thirdly this is unlikely due to the absence of helical structure of the expression product. The impact thereof is totally unpredictable vis a vis stability of expression product and vis avis applicability in photography considering the major structural difference of current gelatins.

The same inventors as the preceding cited patent application disclose in WO93/10154 high molecular weight collagen like protein polymers having repetitive triads with reduced proline content. They are stated as being capable of production in unicellular microorganisms at high molecular weights and at high efficiency. They indicate. "The uniqueness of collagen repetitive tripeptide is a challenge for recombinant technology in light of the high repetitiveness of the sequence and the frequent utility of the amino acids glycine and proline in the composition. Genes encoding proteins with high levels of glycine and proline are by necessity composed of high levels of the nuclcotides guanidine and cytidine in self complementary sequences. Thus as one synthesizes the gene there is substantial opportunity for strands to loop out, single stranded DNA to be excised, recombination events to occur which can result in loss of segments of the gene and inefficient transcription and/or translation. Thus there is substantial interest in developing techniques and compositions which provide the advantageous properties of collagen while at the same time allowing for stable expression of high molecular weight collagen like proteins." In addition it is stated. "The polymers will further be characterised in, being like collagen, providing helices, capable of denaturation and renaturation, forming gels etc." A molecular weight between 30–150 kD is suggested and at least 45 number % of the amino acids between the glycines are proline, at least 80 weight % of triads have glycine as first amino acid, at least 40% by number of the triads comprise at least one proline. The example shows use of 3 types of repetitive GXO encoding sequences and N terminal and C terminal spacer sequences. The same spacer sequences as in the previous patent application were used. The structure of the repetitive sequences was (SEQ ID NO: 3) [[GAHGPAGPK]2(GAPGPAGPP)24(GAHGPAGPK)2]2=[[C]2[A]24[C]2]2. The length of the polypeptide produced was 561 amino acids with a MW of 46.409 Dalton. In another example the repetitive sequence was (SEQ ID NO: 4) [[GAHGPAGPK]2(GAPGPAGPP)12(GAHGPAGPK)2]5=[[C]2[A]12[C]2]5. The length of the polypeptide produced was 777 amino acids with a MW of 64.094 Dalton, with an observed protein band at 100 kD. In the third example the structure was (SEQ ID NO: 5) [[GAHGPAGPK]2(GAPGPAGPPGSRDPGPP)12(GAHGPAGPK)2]4=[[C]2[AB]12[C]2]4. The example had 1065 amino acids and MW 91,966 with a protein band visual at 135 kD. Apparently smaller versions were also produced with protein band weights of 28 kD, 64 and 98 kD. With regard to expression the only details provided are that detection by western blot with antisera was carried out and that the expression of the full length polymer decreased with gene size, whilst the synthesis of full length mRNA was at equivalent levels. Another group of polymers with two other different repetitive units were produced [[C]2[DB]12[C]2]4, (SEQ ID NO: 6) [[C]2[DB]6[C]2]4 (SEQ ID NO: 7) and [[C]2[D]24[C]2]4, (SEQ ID NO: 8) wherein B and C are as above and D=GAQGPAGPG (SEQ ID NO: 9). Respectively these 3 proteins illustrated had 1065 amino acids and MW 91,533 D, 633 amino acids and MW 55,228 D, 1065 amino acids and MW 85,386 D with a protein band visual at 140 kD. Of the examples the only information concerning characteristics of the product are provided for number 6. This product is extremely soluble in water. At room temperature or above solutions thereof of more than 8% in water are viscous but they are fluid and form to a solid gel upon chilling to 0° C. Upon heating above 28° C. the gel forms a thick solution. A thermoreversible transition between liquid and gel is thus illustrated. The final example concerned a structure (GAPSQGAPGLQ)68 (SEQ ID NO: 10) also with the same spacers and 1077 amino acids and a MW 91.266 D. With regard to application of such polypeptide nothing more is stated than in the previously cited application of these inventors. Apparently by varying the block copolymer structure of the repetitive GXO motif it has become possible for expression of longer repetitive sequences to occur. How efficient such protein is expressed is however not clear. Yet again the expression problem due to repetitivity is not illustrated as being solved. It is questionable industrial scale expression could be achieved. No teaching specifically concerning photographic applications is provided. In particular all examples use spacer with cysteine and methionine which is undesirable in photographic applications. Thus a person skilled in the art of photographic applications would be dissuaded from applying the teaching of this document in photographic applications.

French patent 2685347 discusses the desirability of producing recombinant material similar in properties to gelatin. The advantage would be a more homogenous product solving reproducibility problems and the chance to modify chemical functions thereof. The idea is to produce oligopeptides as gelatin substitutes, The microorganism selected was *E. coli* and it is stated the absence of post translation modifications such as glycolisation common to coli is no problem. Other hosts are said to be possible. No examples are however given of such possible hosts. The nucleic acid sequence to be applied must comprise a gelatin peptide encoding sequence for (Gly-X-Y)n linked to Met-Cys-His-His-His-Leu-Met (SEQ ID NO: 11) codons in order for selection to occur. The sequence given by way of example encodes (SEQ ID NO: 12) Gly-Pro-Ala-Gly-Glu-Arg-Gly-Pro-Lys-Gly-Trp-Met. In a later thesis by the inventor it became apparent that the degree of expression was in fact found to be inadequate for any kind of industrial application. In addition the retrieval process of the produced amino acid was complicated. *E coli* was the host cell described and obviously presented as a matter of fact the disadvantages already presented above for a person skilled in the art interested in industrial scale production i.e. lack of secretion, instability of repetitive sequences and thus a low degree of expression. Finally nothing was actually illustrated concerning application of the suggested collagen in a photographic film in this prior art document. Thus a person skilled in the art of photographic applications would be dissuaded from applying the teaching of this document in photographic applications due to unpredictable outcome of such structurally different material.

Finally a U.S. Pat. No. 5,580,712 isssued to Eastman-Kodak in 1996 concerned with specificially modified collagen like polypeptides and application thereof for photographic purposes describes that collagen like peptizers with silver binding strengths below 50 mV can lead to a high degree of thin tabular grain. The document illustrates this for a number of synthetically produced polypeptides with a length of 25 amino acids. The document also mentions one polypeptide with a collagen like structure was produced using recombinant technology. The recombinant polypeptide is a synthetic polypeptide of block copolymer structure consisting of merely 4 different amino acids. No actual expression details are provided for this recombinant polypeptide, a reference is merely made to standard molecular biology production protocols and the use of Saccharomyces cerevisiae as expression host. The molecular weight is approximately 26 kDa. It thus is questionable whether a molecular biologist familiar with the expression problems provided in detail in other documents of the same date and later would seriously contemplate such production. In addition no details concerning binding strength of the recombinantly produced product are provided thus it is also questionable whether a person skilled in the art of photographic applications would seriously consider use of this product in a silver halide emulsion for photographic product or would seriously expect it to exhibit the characteristics of the short synthetic polypeptides disclosed. The document also suggests that the specific polypeptides disclosed comprising histidine and methionine at specific points namely at Xaa of the following formula will exhibit high binding strengths and will exhibit non tabular grain formation. The formula of the compound is (SEQ ID NO: 13) Gly Pro Xaa1 Gly Leu Xaa2 Gly Pro Arg Gly Pro Pro Gly Ala Ser Gly Ala Pro Gly Phe Gln Gly. Analysis of the Table providing details of the compounds researched by Eastman-Kodak reveals that all compounds with high binding strengths had at least one reducing amino acid (=histidine or methionine) per 25 amino acids thus resulting in contents higher than 400 micromoles of methionine per gram of polypeptide. Such compounds will not be useful in nucleation/growth AgX-emulsion processes for photographic applications. The synthetic compounds illustrated as having low binding strength and favouring tabular grain formation did not comprise any reducing amino acids Met or His. A number of other US patents are issued to Eastman-Kodak on related subject matter. These patents (U.S. Pat. No. 5,580,712 and U.S. Pat. No. 5,670,616) revealed other synthetic fragments purported to be useful for tabular grain formation but the same single recombinant product example is described so these patents offer nothing new vis a vis recombinant collagen expression and application of recombinant collagen in photographic applications with AgE-emulsions. It is also derivable from these descriptions of Eastman-Kodak that expression of the specific sequence shown which occurred in the host *S. cerevisiae* was in fact very low. Using 20 litres of culture merely ca 600 mgr of product could be isolated. No attention is paid to this aspect in the descriptions however. In fact the information derivable from these descriptions would dissuade the skilled person from using this system for producing collagen. As addressed already above this low degree of expression could be due to the repetitivity of the sequence to be transcribed/translated and/or the presence of protease. In particular due to the open structure of non helical collagen any non helical collagen expression product is likely to be extremely susceptible to protease attack.

DESCRIPTION OF THE INVENTION

The subject invention is directed at use of recombinant DNA technology thus now finally enabling production of large amounts of substantially pure collagen material overcoming the above mentioned difficulties. For the first time a recombinant collagen production process has been executed providing high level of expression without requiring expensive media, expression hosts or non secreting expression hosts. In addition it has now become possible to produce collagen selected and/or adapted for optimal use in each particular stage of the production process of the photographic product where gelatin has to date been applied. Thereby rendering even further improvement possible. Also an improved AgX emulsion production process is now possible leading to a reduction in production costs.

The subject inventors were interested in obtaining a more uniform photographic AgX-emulsion material and decided to investigate the possibility of producing collagen comparable to that of collagen derived from animal sources currently used in the industrial photographic paper and film making process. They expected that the use of recombinantly produced collagen could lead to improvements in the silver halide emulsion production due to the more uniform nature vis a vis the natural source which comprises a large number of contaminants and a mixture of collagen types of non defined and variable nature with collagen type I as major component. The idea was to use a substance coming close to the natural collagen rather than use of newly designed collagen like polypeptides with higly respective block copolymer structure. The hope was that expression problems for a sequence corresponding to the native sequence would be smaller than those encountered in the synthetically designed collagen like polypeptide sequences as described in detail in the prior art. This could be hoped for on the basis of a lower repetitivity of the sequence to be expressed. On the other hand use of a more random sequence could also lead to more susceptibility to attack by various proteases.

However differently to the native situation for collagen we decided to abandon attempts to produce helix like structures using the recombinant technology. In light of page 1 of WO93/07889 which states "Unless an appropriate number of y-position prolyl residues are hydroxylated to 4-hydroxyproline by prolyl 4 hydroxylase the newly synthesized chains cannot fold into a triple helical conformation at 37° C. If the hydroxylation does not occur the polypeptides remain non helical, are poorly secreted by the cells and cannot self assemble into collagen fibrils" it could have been expected problems would arise upon applying secretory cells to ensure secretion. Also the potential for protease attack would be markedly higher due to the resulting open non folded structure. Thus it is surprising that our recombinant sequences result in expression products that are quite readily secreted by the expression host and in high amounts. Also the production of recombinant collagen under such conditions that the recombinant collagen compound cannot form the fibrillar structure or the triple helix structure characteristic for the native collagen that is currently used in photographic applications could also have had a questionable effect on the photographic application itself. In view of this difference with the current commercial product it was of course also questionable whether the resulting recombinant compound would be as suitable for photographic application as the helix comprising compound currently in use.

The results after a lot of hard work in cloning a genomic sequence for collagen types I and III, overcoming expression problems in order to produce sufficient amounts to start testing it in photographic applications were however in spite of all possible setbacks unexpectedly good. Firstly the rate of expression was unexpectedly high it was higher than 0,95 grammes/liter and was in fact higher than 3 grammes/liter overall. This is in marked contrast to the prior art where any attempts to express collagen or collagenlike material failed to produce more than milligrammes per litre if any. Thus this amazingly high rate of expression was considered totally unexpected firstly in view of all problems described in the prior art. The rate of expression however even actually outnumbered production rates achieved with expression host *Pichia pastoris* for other proteins. Quite specifically even those proteins that were not expected to be as difficult to produce in high amounts like collagen. At long last it now seems feasible a form of recombinant collagen could be produced in an economically interesting amount with an economically interesting expression host. Other high expressing hosts are to be found amoung microorganisms of the fungal type. In particular high expression yeasts and most specifically protease negative strains with low proteolytic activity are preferred. Yeasts that can be suitably used are quite specifically methylotrophic yeasts. A particularly suitable example is the yeast *Pichia pastoris*. On the basis of the criteria established as being relevant for expression of collagen a suitable host cell capable of expression to a degree high enough and under economically feasible conditions can be found and used.

The fact that large scale production was finally made possible by the subject inventors finally also enabled actual tests in the photographic application field to be carried out. Tests for photographic application were only made possible after sufficient recombinant collagen had been produced in relatively large amounts, which is in contrast to the small amounts required in the pharmaceutical applications described in detail in the prior art. After carrying out these tests directed at photographic application it was discovered tabular grain formation was high (see Table II). For the first time the application of substantially pure collagen type III was applied in a photographic emulsion as peptizer. The results were outstanding. Quite unexpectedly however we found a degree of tabular grain formation higher than 80%. This even outdid the Eastman-Kodak polypeptide performances of polypeptides with low binding strengths and this was considered most surprising in view of the fact that a binding strength of 69,5 mV was found for this product and thus in line with the Eastman-Kodak teaching non tabular grain formation was to have been expected. Thus the theory postulated by Eastman-Kodak concerning the requirement of the binding strength being below 50 mV to get 80% tabular grain formation is overturned. Thus the pathway was opened to develop numerous peptizers with silver binding strengths higher than those stated in the prior art as being suitable for application in silver halide emulsions requiring tabular grains at a level of more than 80%. The pathway was also opened to apply other types of collagen than type III as major collagen component of peptizer in photographic emulsions. Considering the degree of homology between the various native collagens is 40–50%, one can expect good results also from slightly manipulated native sequences. An amino acid sequence exhibiting more than 50% homology with a native collagen amino acid sequence can be expected to provide good results. Mutations of native sequences can comprise insertions, deletions and substitutions vis a vis the native sequence. Besides, use can be made of synthetic DNA sequences with a certain degree of homology with native DNA sequences. The sequences useful according to the invention must however maintain a minimum degree of variability in order to prevent expression problems of their encoding nucleic acid sequences. Thus the mutations should always result in an amino acid sequence with more than 4 different amino acids. The GXY motif should not be in the form of a block copolymer and should not comprise spacer sequences between a number of GXY motifs. Preferably more than 8, even more than 9 different amino acids should be present. In the example a protein with as many as 19 different amino acids is used. There are only 20 amino acids that occur naturally. Suitably between 10–20 amino acids or 10–19 amino acids can be used (preferably however cysteine is avoided).

The invention thus comprises a tabular silver halide emulsion wherein the tabular grains account for more tan 75% of the total grain projected area said emulsion comprising silver halide grains nucleated in the presence of nucleation peptizer and thereafter grown in the presence of growth peptizer, wherein at least one peptizer is substantially pure collagen like material prepared by genetic engineering, said peptizer having an amino acid sequence comprising more than 4 different amino acids. Such an emulsion can suitably comprise a peptizer with an amino acid sequence which exhibits more than 50% homology with native collagen, preferably more than 60% Suitably the peptizer will have a size of at least 10 kDa. Sizes between 20–80 kDa are useful in photographic application as is apparent from the examples. Peptizers of ca 600 amino acids are illustrated.

The emulsion can comprise peptizer having an amino acid sequence equivalent to that occurring in nature for collagen, wherein equivalent implies amino acid identity of at least 80%, preferably at least 90%, the same as occurs in nature.

The emulsion can comprise a peptizer with an amino acid sequence substantially the same as occurs in nature, wherein substantially implies mutation of less than 5 amino acids, preferably less than 3. Suitable types of collagen are I, II and III. A preference exists for sequences close to the native sequence in order to assure activity and avoid expression problems. The DNA encoding for the peptizer amino acid sequence can be native or synthetic. A collagen type III amino acid sequence acording to the invention suitably comprises or has the sequence of FIG. 3. A collagen type I amino acid sequence according to the invention comprises or has the sequence of FIG. 8, 10 or 12. Collagen type III has the amino acid sequence defined in reference 5 of example 1 and is incorporated by reference.

An emulsion according to the invention wherein the peptizer is present in substantially pure form means that the peptizer is substantially free of nucleic acid, polysaccharides and other protein. The examples illustrate that this is indeed feasible. The presence of sugars and nucleic acid in even trace amounts could have some effects on crystal formation and it was indeed to be questioned whether sufficiently pure recombinant material for the specific photographic application could be produced.

It is advantageous when using *Pichia pastoris* as expression host to use a nucleic acid sequence encoding an amino acid sequence free of the sequence MGPR (SEQ ID NO: 14) even though it is present in the native sequence of collagen type I because we have unexpectedly found this sequence is a new recognition sequence of a protease present in *Pichia pastoris* to which some collagen types are susceptible. It is postulated the protease is a Kex-2 like protease and that a Kex-2 like protease negative host strain will be a suitable host cell. In general terms when using *Pichia pastoris* as host cell it could be advantageous to use a nucleic acid sequence encoding collagen of which the corresponding amino acid sequence is free of [Leu-Ile-Val-Met]-Xaa-Yaa-Arg (SEQ ID NO: 15) wherein Xaa and Yaa correspond to Gly and Pro or other amino acids and at least one of the amino acids between the brackets is amended. As the open structure of non helical collagen is susceptible to proteolysis the host should be selected and/or the sequence to be expressed is preferably mutated or selected such that proteolysis for the specific combination of host and sequence to be expressed is minimized. There are numerous options open to the skilled person to realise this on the basis of common general knowledge and the subject disclosure including the content of the cited references. Another way to increase the expression could lie in optimised codon usage for the host cell in which the sequence is introduced for expression. The use of multicopy transforming is also a way in which increased expression can be achieved. It is suggested in the art for *Saccharomyces cerevisiae* expression of bovine pancreatic trypsin inhibitor that the maximum level of protein secretion is ultimately determined by the protein folding capacity of the endoplasmic reticulum. Exceeding this capacity by the use of multicopy transformants is thought to result in the accumulation of unfolded proteins in the endoplasmic reticulum and a concomitant vast decrease in the level of expression due to physiological instability. This is described by Parekh et al in 1995 (Protein Expr.

Purif. 6, 537–545) and by Parekh and Wittrup in 1997 (Biotechnol. Prog. 13, 117–122. It is feasible that this negative aspect is negated in the case of our recombinant collagen being expressed as an unfolded molecule and/or that this phenomenon is less relevant in other expression hosts in particular other yeast hosts. In yeast hosts and in bacterial hosts prolylhydroxylating mechanisms are absent and as such expression of collagen in such hosts will lead to unfolded collagen. If collagen is unfolded it will not drain the folding capacity of the endoplasmic reticulum. Also due to outstanding solubility unfolded unhydroxylated collagen will most likely not aggregate and accumulate in the endoplasmic reticulum. In order to eliminate the risk of such folding becoming relevant to degree of expression it is thus preferred the collagen is not hydroxylated or is at least hydroxylated to as low a degree as possible.

It has recently been shown that it is possible to achieve hydroxylation in yeast cells such as *Saccharomyces cerevisiae* and *Pichia pastoris* by coexpression of heterologous prolyl-4-hydroxylase. This is described by Vuorela et al in 1997 (EMBO J. 16, 6702–6712) and by Vaughan et al in 1998 (DNA cell Biol. 17, 511–518). As the gelling temperature of gelatin will depend on the degree of hydroxylation it could now be possible to vary the degree of hydroxylation in a manner that will result in an expression product with a different gelling temperature. This could be of particular interest in processes with specific temperature requirements that previously prohibited economical use of collagen e.g. in processes requiring temperature above room temperature to prevent undesirable gelling.

The peptizer does not have to be identical to the native sequence it can be a fragment of defined length and composition derived from a native collagen encoding sequence, said fragment comprising the GXY motif characteristic of collagen, said length being such that the fragment weight on amino acid basis is at least 2,5 kDa. Suitably weights can be between 2.5 and 100 kDa. Fragments of various sizes are suitable. 5–50 kDa even 20–50 kDa are suitable embodiments to be applied. The peptizer can be made de novo from a synthetic nucleic acid sequence.

Various ways of ensuring absence of helix structure are available. For instance ensure the peptizer is free of hydroxyproline and/or free of procollagen and telopeptides. Preferably for photographic applications the peptizer should be free of cysteine. An AgX emulsion according to the invention, wherein the peptizer is not deaminated is an interesting further embodiment of the invention as is a peptizer with an isoelectric point of 7–10.

Further research was carried out to ascertain what else could be discovered to define what other parameters could be used to enhance the results. In order to do this we analysed a number of modified collagens i.e. non recombinantly produced collagens with our recombinant collagens in tests to determine relevant parameters. We subsequently defined various categories of compounds as suitable for producing silver halide emulsions with the required degree of tabular grain formation.

An emulsion according to the invention in any of the other embodiments already mentioned with the peptizer further comprising oxidated reducing amino acids i.e. to a degree that reducing amino acids are present at a level equivalent to a reducing strength of between 0,1–200 micromoles of methionine per gram of said peptizer is a suitable embodiment. Preferably less than 160 more preferably less than 120 micromoles of methionine per gram of said peptizer is present. A lower level of reducing power is preferred so preferred emulsions according to the invention will comprise peptizer comprising oxidated reducing amino acids to a degree that reducing amino acids are present at a level equivalent to a reducing strength of between 0,1–80 micromoles of methionine per gram of said peptizer. Quite high levels of oxidated reducing amino acids to a degree that reducing amino acids are present at a level equivalent to a reducing strength of between 30–80 micromoles of methionine per gram of said peptizer are also able to provide adequate results. This is quite surprising considering the previous teachings concerning requirements for low values of reducing power for tabular grain formation of numerous prior art publications. The invention also covers such modified collagen with lower levels of methionine than 80 $\mu$moles e.g. modified type I. The modification e.g. to the type I collagen does not necessarily have to be by oxidation but can also be the result of mutation of the encoding sequence such that reducing amino acids are replaced to the required degree by non reducing amino acids. This means a chemical treatment step of the collagen prior to use in silver halide emulsion can be omitted with the concomitant advantages in time and cost to the production process. Obviously one can apply a native collagen which does not have more than 80 $\mu$moles of reducing amino acid e.g. collagen type III.

Additionally we discovered contradictory to the teaching of Eastman-Kodak mentioned earlier and published in 1996 that an emulsion according to the invention in any of the other embodiments mentioned, comprising a peptizer with a binding strength for silver higher than 50 mV can function exceedingly well as an emulsion having a high level of tabular grain formation. A suitable peptizer will have a binding strength for silver below 100 mV. Contrary to the prior art teaching the peptizer can have a binding strength for silver between 50–100 mV and provide an emulsion with excellent tabular grain percentage.

The silver halide emulsion resulting from application of such collagen like material will suitably exhibit more than 80% tabular grains, preferably more than 90%. Most preferred is a tabular grain percentage higher than 95%. The grains will exhibit an average aspect ratio higher than 5 when determined using the single jet method under the reaction conditions described in the example. Note these reaction conditions are not the optimised reaction conditions used in actual photographic emulsion processes for obtaining the highest aspect ratios but merely provide an indication of whether the material is suitable to achieve high aspect ratios when such optimised conditions are applied. The compounds according to the invention upon application of optimised conditions currently used on normal collagen e.g. using the double jet method and an additional ripening process are expected to exhibit much higher aspect ratios. The applied test is merely a quick indicator of high aspect ratio forming capacity and the person skilled in the art will realise what measures can be taken to enhance the result further.

In our test the ripening process is carried out without any further addition of peptizer or extra silver. Obviously in a process according to the invention the ripening step could comprise such further addition. The peptizer can be the same material for both nucleation and ripening stage. An additional addition in the ripening stage could be advantageous due to increased steric stability at this stage.

A preferred AgX emulsion according to the invention comprises a peptizer that is stable vis a vis silver halide tabular grain formation at a pH between 4–8. Conventional gelatin derived from lime bone and hydrolysed gelatin do not exhibit such good tabular grain formation results at pH higher than 5,5. The peptizers according to the invention e.g. native recombinant collagen III do exhibit such characteristic thus making the requirement for strict pH control during emulsion production storage and application redundant. The native recombinant collagen can also undergo oxidation of methionine to exhibit improved behavior. Suitably the methionine level will be less than 80 micromoles per gramme. An emulsion according to the invention can thus have a nucleation and growth pH between 4–8 without negatively affecting tabular grain formation. In the process of emulsion production a variation in pH will not negatively effect the outcome upon further processing of the resulting emulsion for photographic element production.

An emulsion according to the invention offers the advantage over conventional collagen comprising silver halide emulsions that the peptizer is of a homo disperse nature. The crystallisation process by virtue of this fact is also more homogeneous with all the advantages mentioned above. It is possible to add at various stages of the nucleation and growth of the silver halide crystals a further homogenous peptizer also clearly defined and substantially pure thus combining price effectiveness and controlling crystallisation properties in a regulated manner previously not possible with a collagen like peptizer. As there are many types of collagen naturally these can also be applied in photographic silver halide emulsions according to the invention.

There are 23 collagen genes that have been discovered so far. Most of these have been sequenced in part or as a whole. The databanks comprise the various sequences therefore. Genbank for example has the coli sequence under accession number Genbank U08020 and the colIII sequence is given in reference 5 of example 1. These native collagen genes exhibit homologies when compared amoung themselves of 40–50%. The relevant information of the cited references with regard to sequence data is hereby incorporated by reference see also e.g WO95/31473 page 5. Application of any of these native sequences as such or modified, obtained by isolation from a natural source or by chemical synthesis, in order to produce a collagen like compound as defined above according to the invention, said compound subsequently being used in a silver halide emulsion for photographic application is covered by the subject invention. Suitably the sequences are applied i.e. sequences encoding polypeptides with the natural amino acid sequences or similar to the natural amino acid sequences as long as the encoded polypeptide falls within the parameters disclosed above. The type I has been the type mostly applied in silver halide emulsions as the source for silver halide emulsion gelatin was animal bones of which type I collagen is the most predominantly present collagen type. Now it has become possible to also test and apply other collagen types for suitability in silver halide emulsions. The other collagen types have not been applied as such in the prior art in photographic applications and certainly not as such in silver halide emulsions. Naturally a number of them have been present in animal tissue that has been used to date. Now it has become possible to see whether these collagen types can in fact be responsible for or contribute to even more favorable properties to photographic products previously unrecognised. A photographic sensitive emulsion comprising recombinant collagen like polypeptide other than type I as collagen like component is also considered to form a suitable embodiment of the invention as long as the specific requirements set out above are fulfilled. Specifically application in a silver halide emulsion is covered. In the case of silver halide emulsions a 100% uniform source of collagen is expected to provide maximum homo dispersity of crystal formation. The requirement of homodispersity and the value thereof have been addressed elsewhere in this description of the invention. It is not necessary for the peptizer to comprise the full length collagen it can comprise a fragment thereof. Suitably such fragment is however at least 2,5 kDa, preferably more than 10 kDa in length to ensure sufficient randomness of expression whilst maintaining collagen aspects required for the peptizer.

Besides the emulsions described above the invention is also concerned with a process for preparing tabular silver halide emulsion wherein the tabular grains account for more than 75% of the total grain projected area said process comprising nucleation of silver halide grains in the presence of nucleation peptizer and thereafter growing said silver halide grains in the presence of growth peptizer, wherein both peptizers are present in a defined amount and at least one peptizer is collagen like material prepared by genetic engineering, said peptizer having an amino acid sequence comprising more than 4 different amino acids. Such a process according to the invention can comprise addition of the peptizer in the nucleation step and/or during the grain growing step, said peptizer can be selected from any of the embodiments disclosed above or in the claims. In a special embodiment the process comprises addition of the peptizer both in the nucleation step and during the grain growing step. The peptizer to be used when both steps are taken can be the same or different depending on the circumstances of the case.

After preparing an AgX emulsion according to the invention the AgX emulsion can undergo the standard procedures for preparing a photographic element. The emulsion can be applied in a manner known per se for achieving a silver halide emulsion layer on photographic material wherein the silver halide crystals of said layer have an aspect ratio of 5 or more. Said photographic element is suitably a material sensitive to light, laser or x-ray radiation, said element being selected from black and white reversal film, black and white negative film, colour negative film, colour reversal film, film in which the sensitive photographic components are digitally scanned, black and white reversal paper, black and white paper, colour paper, reversal colour paper, paper in which the sensitive photographic components are sensitized by laser radiation out of a digital database. A photographic element obtained according to such a process is also covered by the invention as well as an element using the direct positive process with internal sensitised silver halide emulsion and elements using heat development.

Another aspect of the invention lies in a process of producing recombinant collagen like polypeptide comprising expression of a collagen like polypeptide encoding nucleic acid sequence by a microorganism to a degree exceeding 0.95 grammes/liter, said recombinant collagen being free of helix structure. Preferably the expression occurs in a microorganism other than *E. coli* or *Saccharomyces cerevisiae* in order to ensure high expression and preferably secretion. The process can suitably be carried out with a fungal cell preferably a yeast cell. Suitably the host cell is selected from the group consisting of high expression host cells like Hansenula, Trichoderma, Aspergillus and Pichia. Fungal and particularly yeast cells are preferred to bacteria as they are less susceptible to bad expression of repetitive sequences. Most preferably the host will not have a high level of proteases that attack the collagen structure expressed. In this respect Pichia offers an example of a very suitable expression system. Preferably the microorganism is free of active post translational processing mechanism for processing collagen like sequences to fibrils thereby ensuring absence of helix structure in the expression product. Also such a process can occur when the microorganism is free of active post translational processing mechanism for processing collagen like sequences to triple helices and/or when the nucleic acid sequence to be expressed is free of procollagen and telopeptide encoding sequences. The host to be used doe not require the presence of a gene for expression of prolyl-4-hydroxylase the enzyme required for collagen triple helix assembly contrary to previous suggestions in the art concerning collagen production. The selection of a suitable host cell from known industrial enzyme producing fungal host cells specifically yeast cells on the basis of the required parameters described herein rendering the host cell suitable for expression of recombinant collagen according to the invention suitable for photographic applications in combination with knowledge regarding the host cells and the sequence to be expressed will be possible by a person skilled in the art.

To ensure production of a non cleaved sequence a process according to the invention for producing recombinant collagen like material comprises use of a nucleic acid sequence encoding recombinant collagen amino acid sequence substantially free of protease cleavage sites of protease active in the expression host cell. In the case of *Pichia pastoris* for example and possibly also for other host cells a nucleic acid sequence encoding collagen of which the corresponding amino acid sequence is free of [Leu-Ile-Val-Met]-Xaa-Yaa-Arg (SEQ ID NO: 15) wherein Xaa and Yaa correspond to Gly and Pro or other amino acids and at least one of the amino acids between die brackets is amended could be preferred. A preferred process according to the invention comprises use of the microorganism *Pichia pastoris* as expression host.

The process suitably provides expression leading to peptide harvest exceeding 3 grammes/liter. The process can suitably be carried out with any of the recombinant collagen like peptizers defined above for the emulsion according to the invention. As is apparent from the examples under the circumstances described therein multicopy transformants provide more than 14 grams of gelatin per liter of clarified broth at a biomass wet weight of 435 grams per liter. Most suitably the product resulting from microbial expression is isolated and purified until it is substantially free of other protein, polysaccharides and nucleic acid. As is apparent from the examples numerous methods are available to the person skilled in the art to achieve this. The process according to the invention can provide the expression product isolated and purified to at least the following degree: content nucleic acid less than 100 ppm, content polysaccharides less than 5%, content other protein less than in commercial products. More preferably the DNA content of less than 1 ppm, RNA content less than 10 ppm even less than 5 ppm and polysaccharide content less than 1% can be achieved.

Another aspect of the invention covers novel recombinant collagen like peptides. In particular the invention covers a substantially pure collagen like material prepared by genetic engineering of collagen encoding nucleic acid, said peptizer having an amino acid sequence exhibiting more than 40% homology with native collagen and comprising more than 4 different amino acid types. The nucleic acid sequence can be derived from the native sequence or be synthetic nucleic acid synthesized de novo. Other suitable embodiments are those peptizers described in the emulsion embodiments according to the invention. As close a homology as possible is preferred as homologies higher than 50% preferably even in the order of 80% are desired, even 80–100%. We specifically point out the products are preferably free of block-copolymer structure within the GXY motif sequence.

In a preferred embodiment of the invention the collagen like material comprises no cysteine residues. The presence of cysteine in photographic product will disturb the product manufacturing process. It is thus preferred that cysteine is present in as small an amount as possible. This can be achieved either through chemical modification of the recombinant product or mutation in the nucleic acid sequence encoding the product by mutation or deletion of a cysteine encoding sequence such that cysteine is no longer encoded. Suitably photographic applications will employ material comprising less than 0,1% cysteine.

In particular for the optimal silver halide emulsion homogeneity of the collagen material is of the utmost importance. It is not merely a question of absence of impurities that provides an improvement it is the possibility of providing molecules of exactly the same composition and length allowing good control of the extremely sensitive process of crystallisation and also enabling uniform crystal growth. For this reason recombinant collagen like material will be valuable for this part of the photographic manufacturing process. In addition the absence of fibril formation and even of triple helices is required for this particular application in the photographic manufacturing process an aspect that until now had been completely overlooked. The insight in the relevance of the number of reducing groups in the photographic material is also of great importance. This is not the rigid low amount suggested in the prior art required for tabular grain formation. Thus the reduction in cysteine, histidine and methionine levels in the collagen like material to be applied forms a preferred embodiment of the invention.

The compounds according to the invention have also revealed an additional advantage. The known collagen materials e.g. regular and hydrolyzed collagen from animal sources such as bone and hide result in low tabular grain formation of the photographic film emulsion at higher pH than 5.5. The new group of recombinant collagens have been found to result in the same astonishingly high degree of tabular grain formation not only at pH 5.5 but also at higher pH e.g. pH 7. This offers the possibility of preparing silver halide emulsions which have less stringently controlled pH as the new compounds are apparently less pH dependent then the non recombinant collagens. Thus the invention is also directed at recombinant collagen like compounds that can be used in the production of silver halide emulsions at a pH between 4–8 whilst still arriving at high tabular grain percentages i.c. higher than 50% preferably higher than 80%. An additional characteristic of the recombinant collagens that can be considered useful is the fact that the isoelectric points are basic as opposed to the recombinant Eastman-Kodak polypeptide described in 1996 which has an acidic IEP. It is expected that the fact that the recombinant collagen according to the invention has an amino acid composition wherein more than 4 amino acids are present offers increased variability in the encoding sequence and thus allows higher degree of expression. Additional variety is introduced by use of a sequence with a GXY motif with less than 33% proline in the total GXY sequence. The good expression is achieved without use of a block copolymer amino acid structure in the GXY sequence.

The invention will further be illustrated by the examples.

EXAMPLES

Example 1

Gelatins, collagen or collagen fragments expressed as recombinant, heterologous protein in expression host organisms like yeast, fungi bacteria for photographic applications by recombinant-DNA techniques has several advantages. (i) In contrast to for example traditional gelatins, recombinant molecules can be produced as rigorously non cross-linked. (ii) The molecular composition is precisely-defined. (iii) The molecules produced are of a single type (or a well-defined mixture of only a few molecules), with minor or negligible contamination from other proteinaceous or non-proteinaceous molecules. The molecular weight distribution is very narrow and mono-disperse (single-component gelatins) or oligo-disperse. (iv) The product can be manufactured in a highly reproducible way, i.e. with constant quality. Especially yeast are well-suited production organisms for such polypeptides with a highly repetitive, glycine- and proline-rich sequence.

Whereas these molecular features often cause genetic instability (e.g. recombination and shuffling of parts of the gene) in bacterial systems, this appeared to be not much of a problem in yeast [1,2]. They are eukaryotic cells, in which post translational modifications like hydroxylation can be effectuated, and which allow to choose for either efficient secretion or intracellular expression. Several species grow efficiently on cheap substrates like methanol, in contrast to animal cell cultures. Secreted production allows efficient recovery of the product during or after fermentation (contrast with plants). Several strong and tightly-regulated inducible promoters are available for yeast systems, allowing a highly efficient expression and minimizing possible negative effects on the viability and growth of the host cells. As one of several well-suited systems that are available, we have chosen for secreted production by the methylotrophic yeast *Pichia pastoris*. Our expression levels are among the highest ever reported for recombinant proteins, indicating the ability of this expression host to cope with the aforementioned of the structure of gelatin/collagen at genetic (DNA, RNA) and protein levels. After transformation of the host, the integrative is incorporated into the yeast's genome, resulting in genetical stability of the transformants (loss of plasmids is then of no importance). It is possible to generate transformants (with the heterologous target gene under the control of e.g. the alcohol oxidase (AOX) promotor), in which the recombinant gene is either incorporated into the HIS4 locus or the AOX1 locus. In the latter case, depending on the type of integration, the AOX1-gene is disrupted, leading to slow utilisation of (and slow growth on) methanol (Mut$^S$ phenotype). If the functional AOX1 gene is still present, the phenotype is Mut$^+$. Although both phenotypes can be used, we generally preferred fast growth and thus, our protocols were mainly directed at the generation and selection of Mut$^+$ transformants. It is self-evident that yeast or fungal expression systems other than the *P. pastoris* expression system could in principle be used equally well for the efficient production of recombinant gelatins, depending on the exact type and quality of molecule to be produced, on the production scale envisaged, and on the production costs and applicable market prices. The Pichia system was used as a fast and efficient system for pilot production and relatively easy product recovery.

MATERIALS, METHODS & ANALYSES

General Molecular-biological Techniques

Cloning procedures were carried out essentially according to Maniatis et al. [3]. DNA was isolated using Wizard Plus SV miniprep, or Qiagen midiprep systems. DNA was isolated from agarose gels using the QIAquick Gel Extraction Kit (Qiagen). All enzymes used were from Pharmacia unless otherwise stated and were used according to the manufacturer's recommendations. Transformation of *E. coli* was performed by standard electroporation using the BioRad GenePulser. All procedures involving the handling and transformation of *Pichia pastoris* and the expression of proteins in this host organism were essentially carried out according to the manual of the Pichia Expression Kit (from Invitrogen) [4].

Insertion of a Rat COL3A1 cDNA Fragment into a Yeast (*Pichia pastoris*) Expression Vector Plasmid pRGR5, containing a partial rat proα1(III) collagen cDNA, was a kind gift of Dr. Vuorio [5]. It was digested with PstI, yielding an approximately 0.7 kb fragment of the helical domain. Using the 3'–5' exonuclease activity of T4 DNA polymerase the fragment was blunt-ended and subsequently ligated with T4 DNA ligase to SnaBI digested and CIP dephosphorylated pPIC9 *Pichia pastoris* expression vector (Invitrogen). The ligation reaction was then used to transform *E. coli* JM109.

It will be understood that the choice of possible and suitable vectors is not restricted to pPIC9. Anyone skilled in the art will be able to use and adapt a number of other possible vectors such as pHIL-S1, in which a *Pichia pastoris* acid phosphatase 1 (Pho1)-signal instead of the *Saccharomyces cerevisiae*-derived alpha-mating factor (αMF) prepro signal is used, or pHIL-D1, for intracellular expression, and many others.

Plasmid DNA was isolated, and the sequence of the pCOL3A1 construct thus created (FIG. 1) was verified by sequencing according to the method of Sanger [6], using an automated sequencer (ALF DNA Sequencer, Pharmacia) and by using the 5'AOX1, 3'AOX1 and α-Factor (αMF) sequencing primers suggested in the Pichia Expression Kit (see FIG. 2) (SEQ ID NOS: 35–37, respectively). The protein sequence expected for the expressed protein is indicated in FIG. 3 (SEQ ID NO: 38).

Transformation of *Pichia pastoris* with pCOL3A1

In order to obtain Mut$^+$ transformants upon transformation of *Pichia pastoris*, the construct was linearized with SalI. In order to obtain Mut$^S$ transformants the construct was digested with BglII. After phenol extraction and ethanol precipitation, the construct was then used to transform *Pichia pastoris* strain GS115 (Invitrogen) using electroporation according to Becker and Guarente [7] using the BioRad GenePulser (set at 1500V, 25 μF and 200 Ω and using 0.2 cm cuvettes). The transformation mix was plated out on Minimal Dextrose plates (MD-plates; 1.34% YNB, 4×10$^{-5}$% biotin, 1% dextrose and 1.5% agar) in order to select for the presence of the vector which converts the His strain GS115 to His$^+$. After growth at 30° C. for 3 days, several colonies were selected for PCR confirmation of the Mut genotype. Genomic DNA was isolated according to the yeast miniprep method of Lee [8] and RNase A treated. PCR was performed using 100 ng of genomic DNA, 50 pmol 5'AOX1 primer, 50 pmol 3'AOX1 primer, 1.25 U Taq polymerase (Pharmacia), 0.2 mM dNTPs (Pharmacia) and 1×Taq buffer (Pharmacia) in a total volume of 50 μl. After an initial denaturation at 94° C. for 5 minutes, 30 cycles were perfomed consisting of 1 minute at 94° C., 1 minute at 57° C. and 2 mimutes at 72° C. Final extension was at 72° C. for 10 minutes. The PCR machine used was the Perkin-Elmer GeneAmp 480. Agarose gel electrophoresis should reveal a 2.2 kb endogenous AOX1 band for Mut$^+$ transformants. Transformants without 2.2 kb band are Mut$^S$. Verified transformants of both the Mut$^+$ and Mut$^S$ genotype were selected for small-scale expression in 50 ml conical tubes (placed at an angle and with the cap loosely attached), or in 100 ml or 1l (baffled) flasks.

Expression of COL3A1 Fragment

Expression was performed essentially as described in the Pichia Expression Kit manual. Briefly, transformants were grown overnight in BMG (100 mM potassium phosphate pH6.0, 1.34% YNB, 4×10$^{-5}$% biotin and 1% glycerol) to an $OD_{600}$=2–6. Cultures were then centrifuged and resuspended in BMM (as BMG but 0.5% methanol replaced the glycerol) to an $OD_{600}$ of 1.0. Cells were grown for 4 days at 30° C. and 250 rpm, with methanol being added to 0.5% every day.

10 μl of the culture supernatants was analyzed by SDS-PAGE according to Laemmli [9] in a BioRad mini-PROTEAN II system. Coomassie Brilliant Blue staining revealed several bands, the highest of which had the expected apparent length of about 29 kD. It should be noted that gelatin, collagen and collagen fragments migrate according to an apparent Mw, which is about a factor 1.4 higher than the true Mw, at least partly due to the relatively low mean residue Mw [12].

In order to establish their identity, an SDS-PAGE gel loaded with acetone-fractionated COL3A1 fermentation supernatant (see below for the fractionation procedure) was blotted to an Immobilon P$^{SQ}$ membrane (Millipore) using the Biorad Mini Transblot Cell. Quantitative transfer was achieved by applying 100V for one hour, using CAPS buffer (2.2 g CAPS per liter of 10% MeOH, pH 11). After staining with Coomassie Brilliant Blue, the four most prominent bands were cut out and the N-terminal sequence was determined by Edman degradation. The 29 kD band did not give any signal and is probably N-terminally blocked. One of the two smaller fragments was not pure enough to be sequenced. The other two smaller bands did give readable signals and are underlined in FIG. 3. It is clear that the bands are caused by some form of proteolysis, which can be explained by the fact that gelatin is a very open protein in the random coil conformation and is thus highly susceptible to proteolysis.

Protease Activity

Degradation of the collagen was observed of collagen types I and III during fermentation at pH 5.0. Tests were carried out to further characterize this degradation. This degradation was markedly reduced when carrying out the fermentation process at a lower pH. Specifically pH 3,0 provided good results. We also researched the effect of addition of casamino acids. The addition gave protection for both types of collagen at pH 5,0. Furthermore the addition provided even better protection for collagen type I also at pH 3,0. This additional protection was not noticable in the case of collagen type III at pH 3,0. It is presumed extracellular neutral proteases attack the collagen which is extremely vulnerable to proteolytic degradation resulting from it's random coil conformation. (See below for a description of the fermentation procedure). The tests were carried out with the collagen-containing supernatants of a pCOL3A1 fermentation at pH 3.0, where degradation during fermentation was minimal. After removal of the cells by centrifugation, the pH of the supernatants was adjusted to pH 5.0. Subsequently, parallel incubations were carried out with the following additions:
(1) fresh *Pichia pastoris* cells (washed with MilliQ)
(2) fresh *Pichia pastoris* cells (washed with MilliQ) and glass beads: this mixture was vortexed (positive control I).
(3) nothing added (negative control)
(4) trypsin (5 mg/ml) (positive control II).

All samples were incubated for 96 hours at 30° C. and pH 5.0. (These were the conditions that caused degradation of the gelatin during fermentation). Finally, the incubated samples were analyzed on an SDS-PAGE gel according to Laemmli [9] in a Biorad mini-PROTEAN II system, followed by a Coomassie Brilliant Blue staining.

The results were:
(1) incubation at pH 5.0 with washed intact cells caused degradation of pCOL3A1 (originally produced at pH 3.0) into 4–5 discrete bands, probably as a result of cell-surface associated proteolytic enzyme activity;
(2) addition of broken cells caused degradation of both collagen types into a large number of proteolytic products (positive control I);
(3) no degradation occurred in the absence of cells at pH 5.0;
(4) addition of trypsin caused massive degradation of the gelatin (positive control II).

In different experiments, we verified that after removal of the cells at the end of the fermentations, the recombinant gelatins in the cell-free fermentation broth were stable for several days in the temperature range of 0–30° C. and the pH range of 3.0–7.0. Thus, some proteolytic degradation of gelatin occurred during fermentation, but after removal of cells, no relevant proteolytic activity remains and, no further precautions are necessary to stabilize the product. A similar stability was observed for the COL1A1 products described below. This stability of the recombinant gelatins came as a surprise, as they are not hydroxylated (shown by analysis of amino acid composition, as described below) and, accordingly, non-helical, i.e. without any secondary structure. The total absence of secondary structure (i.e. of collagen-type helix) and of hydroxyproline was verified, respectively, by circular dichroic spectroscopy (CD) according to ref. [13] and by HPLC analysis of the amino acid composition after full hydrolysis of the peptide bonds. At 5 degrees Celsius it was ascertained that the expression product remained largely in the random coil configuration and is thus essentially non gelling. This is in accordance with the absence of helix stabilizing hydroxyprolines as confirmed by the experiments. The recombinant gelatins are thus extremely open molecules (and as such unparalleled polypeptides!) that are bound to be extremely prone to proteolytic degradation. The unexpected stability of the product in this expression host (also after secretion) greatly facilitates the downstream processing and isolation of the product from this expression system and obviates the repeated addition of expensive and instable inhibitors of proteolytic activity (e.g. para-methyl-sulfonyl fluoride (PMSF)). In addition, it opens up possibilities for minimizing gelatin degradation during high cell-density fermentation, viz. by continuously separating the product from the cells during fermentation, using simple micro filtration or dialysis against nutrient broth, and by recirculating the cells to the fermenter Previously only TRIPLE-HELICAL collagen or folded polypeptides have been produced. These are more resistant to proteases. Triple helical collagen is even fully resistant to trypsin, pepsin, and other well-known proteases. In contrast, the production of intact, non-hydroxylated and unfolded gelatin was thus expected to be extremely difficult.

Production in a Protease-deficient Strain

In order to investigate if the pep4 proteinase A deficient strain SMD1168 (Invitrogen), is better suited for the expression of the protease sensitive gelatin sequences, this strain was also transformed with the pCOL3A1 construct. Methodology was as described above. Unfortunately there was no clear positive effect in both shake flask and fermenter expression experiments.

Analysis of Glycosylation

In order to establish if the protein is glycosylated, a PAS staining, involving the application of Schiff's reagent after oxidation by periodic acid, was performed on an SDS-PAGE gel. The gel was incubated for 1 hour in 12.5% TCA, 1 hour in 1% periodic acid/3% acetic acid, 1 hour in 15% acetic acid (replaced every 10 minutes) and 1 hour in Schiff's reagent (at 4° C. in the dark). The gel was then washed two times for 5 minutes in 0.5% sodium bisulfite and destained in 7% acetic acid. The expressed protein bands gave no signal, while there was a signal from a positive control (carboxypeptidase Y). As expected, no signal was obtained with a negative control (E. coli extract). It can be concluded that the expressed protein is not glycosylated.

Northern Blotting

A northern blot of methanol grown cells was performed. RNA was isolated according to the method of Schmitt et al. [10]. The pCOL3A1 vector was digested with EcoRI/SphI to give a 0.5 kb COL3A1 fragment. The fragment was $^{32}$P random primer-labeled and hybridized to the blot, after which the blot was washed to a final stringency of 0.2×SSC at 65° C. Autoradiography revealed a messenger of the expected length (1.3 kb).

Pichia Transformants Containing Multiple Copies of the Heterologous COL3A1 Gene

In order to investigate whether gelatin expression levels can be enhanced even further, the G418 multi copy selection method of Scorer et al. [11] has been applied. The pPIC9K vector was digested with BamHI/EcoRI and the 9.0 kb band was isolated. The pCOL3A1 vector was also digested with BamHI/EcoRI and the resulting 1.0 kb fragment was ligated to the 9.0 kb pPIC9K band after which E. coli JM109 was transformed. The construct pCOL3A1K (FIG. 4) thus obtained was verified by restriction digestion.

Pichia pastoris GS115 was transformed with the pCOL3A1K vector as described before (digested with SalI in order to obtain Mut$^+$ transformants). In order to select for multicopy transformants, the his$^+$ colonies on MD-plates were pooled (approximately 6000) and subjected to secondary screening on plates containing a series of 10 different G418 (Gibco-BRL) concentrations ranging from 0.25 to 4.0 mg/ml. The cells were plated at a density of approximately 10$^5$ cells per plate. After incubation for 4 days at 30° C. several resistant colonies of each G418 concentration were transferred to fresh plates at the corresponding level of G418 to verify their resistance.

In order to determine the copy number of the pCOL3A1K vector in the G418 resistant transformants, a semi-quantitative dot blot was performed. Genomic DNA of the verified G418 resistant transformants was isolated according to the protocol of Lee [8] and RNase A treated. Approximately 200 ng of genomic DNA of each of 40 transformants (4 per concentration of G418) was transferred to a positively charged nylon membrane (Boehringer Mannheim) by means of a vacuum blotting device (Gibco-BRL Convertible system). As a 1-copy control a pCOL3A1 transformant which had been verified to contain only 1-copy by Southern blot was also transferred to the blot (in duplo), as well as a non-transformed control (in duplo).

The pCOL3A1 vector was digested with EcoRI/SphI to give a 0.5 kb COL3A1 fragment. This fragment was $^{32}$P random primer-labeled and hybridized to the dot blot filter. After washing to a final stringency of 0.5×SSC at 65° C., autoradiography was performed. After stripping (the efficiency of which has been checked), the membrane was hybridized to a probe derived from a verified Pichia pastoris URA3-fragment, which had been picked up by PCR with heterologous URA3 primers. This control serves for normalization of the COL3A1 signals for the amount of DNA loaded. The membrane was washed and subjected to autoradiography as described for the COL3A1 probe. The signals on both autoradiograms were densitometrically quantified using a gel scanner (PDI, Pharmacia). As expected there was no COL3A1 signal for the 0-copy controls, while there was a URA3 signal. The copy number can be estimated by calculating the ratio of COL3A1 signal for each transformant and the average COL3A1 signal obtained for the 1-copy controls, as normalized by the ratio of the respective URA3 signals (i.e. to account for differences in the amount of DNA blotted to the membrane). Transformants containing approximately 1 to 15 copies were thus obtained.

Expression of COL3A1 Fragments in Multi-copy Transformants

A series of transformants containing 1 to 15 copies was subjected to small-scale expression as described above. Since SDS-PAGE indicated a higher yield at higher copy number, further tests were carried out at a 100 mL scale with the 2-, 5-, 10- and 15-copy transformants. They were grown overnight in 100 ml flasks, containing 25 ml BMG (100 mM potassium phosphate pH 6.0, 1.34% YNB, 4.10$^{-5}$% biotin and 1% glycerol). After centrifugation at 1500–3000 g for 5 minutes, the cells were resuspended in 100 ml BMM (as BMG but 0.5% methanol instead of the glycerol). They were grown in 1 liter baffled flasks at 30° C. and 250 rpm for 4 days, with methanol being added to 0.5% every day. 1 ml samples were taken each day and analyzed on SDS-PAGE. A higher copy number resulted in a higher amount of gelatin product. Selected 5- and 15-copy transformants were used for expression tests in a fermenter at a 1 L-scale. The highest COL3A1 production was obtained with the 15-copy transformant (about 14.8 g gelatin/L in the extracellular medium at a dry biomass of 177 g/L and after about 184 hours of fermentation, i.e. about 7.7 g/L overall, or 42 mg/(L.hour); at a dry biomass of 110 g/L and after about 120 hours of fermentation, it was about 7 g gelatin/L in the extracellular medium, i.e. about 3.7 g/L overall, or 31 mg/(L.hour)).

Cloning of a Mouse COL1A1 Fragment (COL1A1-1) Mouse

Figure 6:
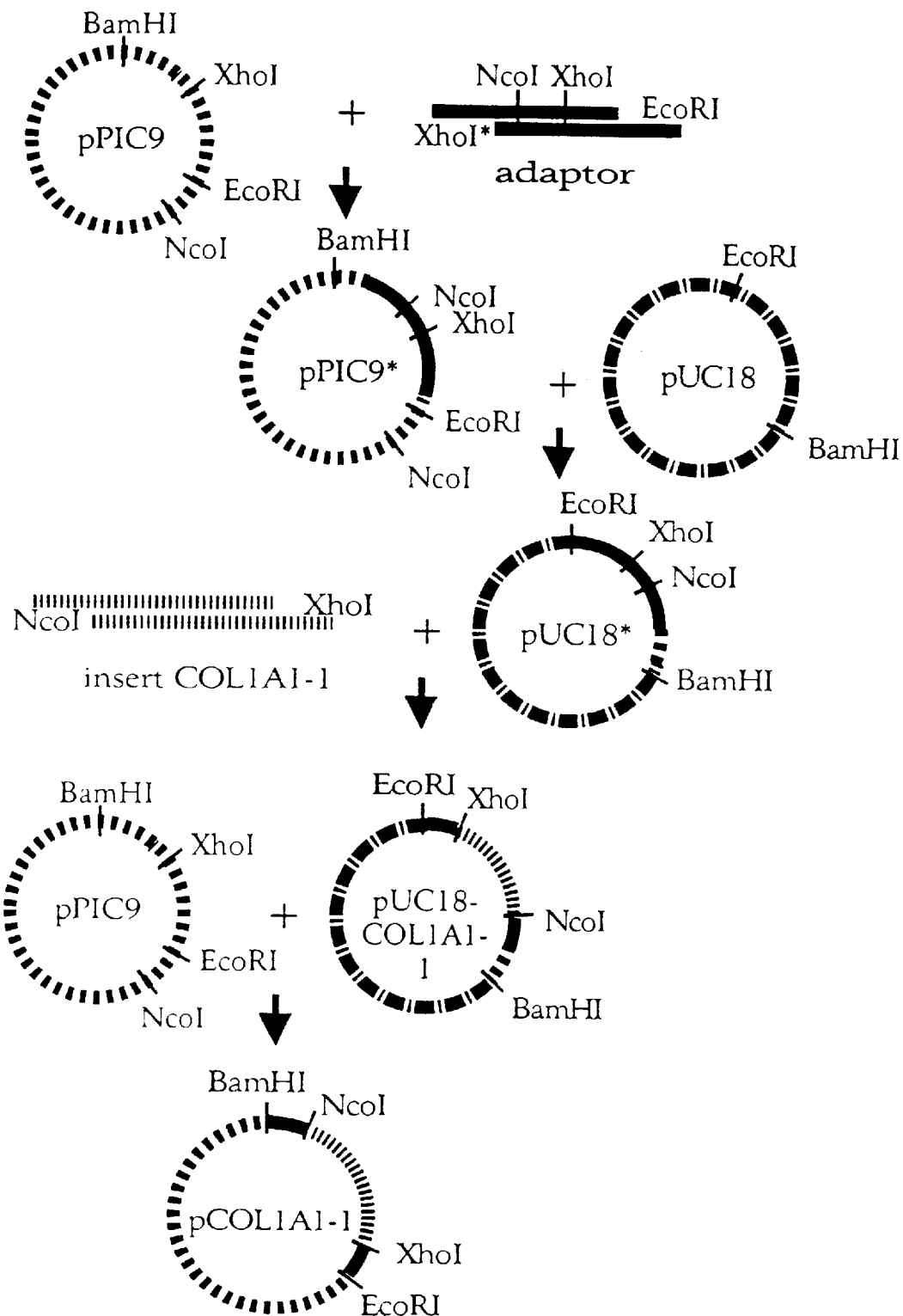
Figure 7:
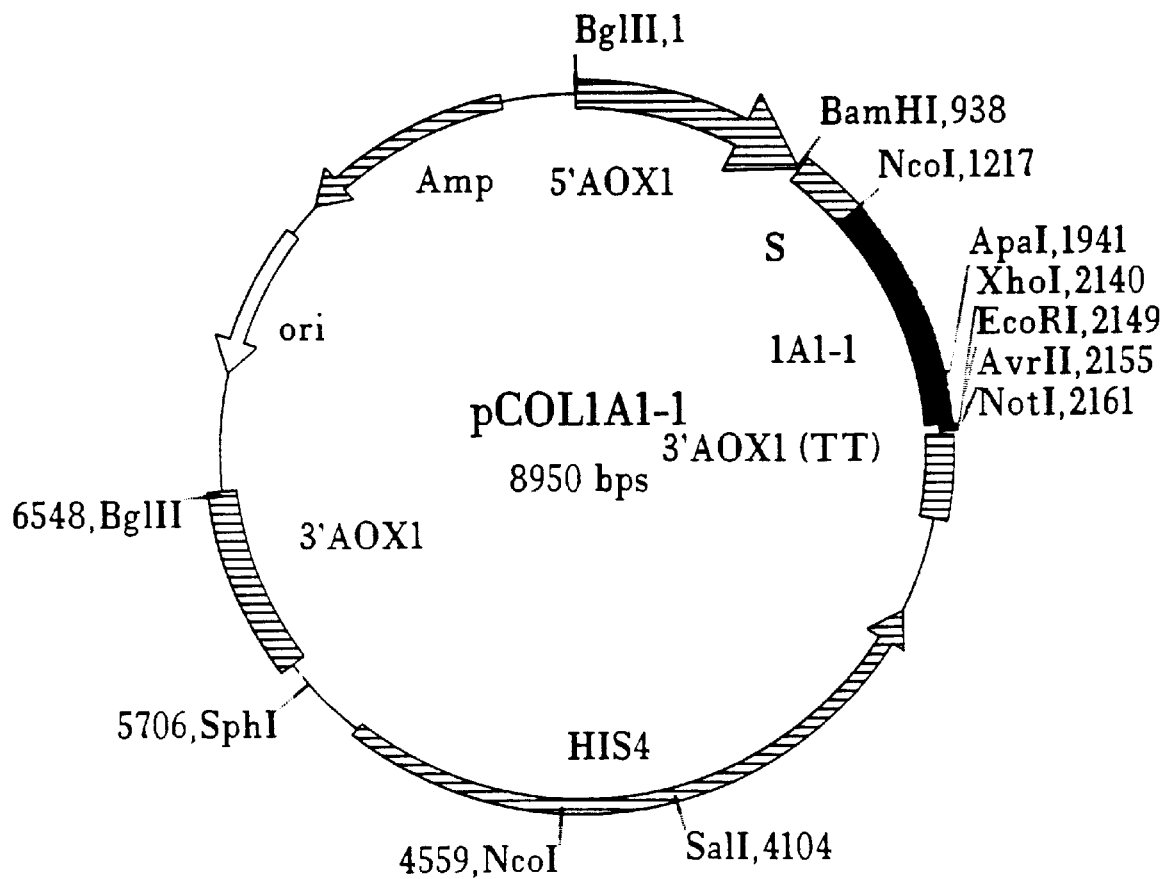

Primers were designed on the known sequence (FIG. 5) (SEQ ID NOS: 39–46, respectively). PCR was performed on Mouse 17-day Embryo QUICK-Clone™ (fibroblast) cDNA (Clontech), using 0.4 ng of cDNA, 0.4 μM C1A1-FW primer (FIG. 5), 0.4 μM C1A1-RV1 primer (FIG. 5), 1×Advantage KlenTaq Polymerase Mix (Clontech), 0.2 mM dNTP's (Pharmacia) and 1×KlenTaq PCR reaction buffer (Clontech) in a total volume of 20 μl. After an initial denaturation at 94° C. for 4 minutes, 35 cycles were performed of 1 minute at 94° C., 1 minute at 68° C. and 2 minutes at 72° C. Final extension was at 72° C. for 10 minutes. Agarose gel electrophoresis shows a 1 kb band, which is the size predicted from the sequence. DNA was isolated from the agarose gel and subsequently digested with NcoI and XhoI restriction enzymes. The digested fragment was isolated from agarose gel and cloned into the *Pichia pastoris* expression vector pPIC9 according to the following strategy (FIG. 6). First, an adaptor containing a NcoI and a XhoI site, was inserted in the multiple cloning site of pPIC9, yielding pPIC9*. The adapter was prepared by annealing the synthetic oligonucleotides N-X-FW and N-X-RV as shown in FIG., 5 and FIG. 6. The single-strand overhang originating from the 5' end of the oligonucleotide N-X-RV was designed to form an EcoR I site after annealing with the EcoR I-digested vector. The 5' overhang from N-X-FW (Xho I*) was complementary to the overhang created by the action of Xho I on the vector, but did not give rise to an Xho I site after ligation. Because the target vector, pPIC9, has an Nco I site outside the multiple cloning site, pUC18 has been used as an intermediate vector for the cloning of this fragment. The section between BamHI and EcoRI of the altered multiple cloning site of pPIC9* was transferred to the multiple cloning site of pUC18 vector, resulting in pUC18*. The NcoI-XhoI digested fragment COL-1A1-1 was ligated in the pUC18* vector between the NcoI and XhoI sites. From this pUC18-COL1A1-1 construct the COL1A1-1 fragment, together with the part of the multiple cloning site from the pPIC9, was digested with BamHI and EcoRI and ligated in pPIC9, yielding the construct pCOL1A1-1 (FIG. 7). Thus, a partial NcoI-digestion of the pPIC9 was not necessary. The correct insertion in pPIC9 was first checked by restriction analysis and then by DNA sequencing.

Transformation of Pichia with pCOL1A1-1 and Expression of the COL1A1-1 Fragment

*Pichia pastoris* GS115 was transformed with the pCOL1A1-1 vector as described for the pCOL3A1 vector. Sal I-digested DNA was used in order to specifically generate Mut$^+$ transformants. Several transforming were used for small-scale expression in shaking flasks and one of those was selected for expression in the fermenter at a 1–100 L scale. Typical yields are in the range of 4–5 g gelatin/L in the (extracellular) medium (as determined after acetone fractionation, described below), at a dry biomass of 100–120 g/L (about 3 g gelatin/L overall). The target gelatin (FIG. 8) (SEQ ID NO: 47) has a theoretical Mw of 27.4 kD. Collagenous proteins and gelatin are known to migrate at an apparent Mw approximately 1.4 times higher than the true Mw [10]. In agreement, an SDS-PAGE band migrating at an apparent Mw of about 38 kD was observed (interpolated value obtained with globular protein Mw markers). In addition, three shorter products with an apparent Mw of 24, 18 and 15 kD were observed (interpolated values). These could be the result of early proteolytic activity in the intracellular, cell surface-associated or extracellular compartments, or from problems at the level of translation. The degradation products were present already at very early stages of induction and no further degradation occurred. Even incubation in the presence of washed intact cells at pH 5.0 and 30° C. during 96 hours did not cause further degradation of pCOL1A1-1 with respect to the situation after fermentation at pH 3.0. (Massive degradation occurred in the presence of trypsin, as a positive control). In order to verify that problems at the mRNA level were not responsible for the occurrence of the 24, 18 and 15 kD products, Northern blotting was performed as described for COL3A1, using a $^{32}$P random-primer labeled 1.0 kb NcoI/XhoI COL-1A1-1 fragment from pCOL1A1-1 as the probe. The expected 1.6 kb messenger was found.

In order to establish the identity of the observed fragments, an SDS-PAGE gel loaded with acetone-fractionated COL1A1-1 fermentation supernatant was blotted to an Immobilon P$^{SQ}$ membrane (Millipore) using the Biorad Mini Trans-blot Cell. (See below for a description of the acetone fractionation procedure). Quantitative transfer was achieved by applying 100V for one hour, using CAPS bluffer (2.2 g CAPS per liter of 10% MeOH, pH 11). After staining with Coomassie Brilliant Blue, the four most prominent bands were cut out and the N-terminal sequence was determined by Edman degradation. The sequencing signals obtained were extremely low as compared with the amount of loaded material (on average around 5%). It is therefore likely that the fragments were for the most part N-terminally blocked. This supports the idea that proteolysis of COL1A1-1 takes place intracellularly. The large amount of COL1A1 supplied, allowed nevertheless an easy determination of the N-terminal sequence. The N-terminal sequences obtained are underlined in the protein sequence (FIG. 8) as encoded by the transfected COL1A1-1 gene. The fragments with an apparent Mw of 38 kD and 18 kD both gave the sequence expected for the N-terminus of the protein, but extended with 'EA'. This extension (or EAEA) is known to be present on some proteins expressed from expression vectors utilizing the *Saccharomyces cerevisiae*-derived alpha-mating factor (αMF) prepro signal. This effect is assumed to be due to steric hindrance of STE13 cleavage activity. However, because most of the protein is probably N-terminally blocked, it may well be that this extended version represents only the minor fraction that is sequenceable. Based on the N-terminal and internal sequences, the fragments with an apparent Mw of 38, 24, 18 and 15 kD were assigned to be fragments consisting of, respectively, residue 1-310, 126-310, 1-125, and 42–125 of the target product as shown in FIG. 8, and having theoretical Mw's of 28, 16, 12, and 8 kD, respectively. Fragments corresponding to residue 1-41 (theoretical Mw 4 kD) and 42–310 (theoretical Mw 24 kD, apparent Mw 34 kD) were not observed. This could be due to a (much) more frequent cleavage between residue 125 and 126 than between residue 41 and 42.

Cloning and Expression of Mouse COL1A1-2

Figure 9:
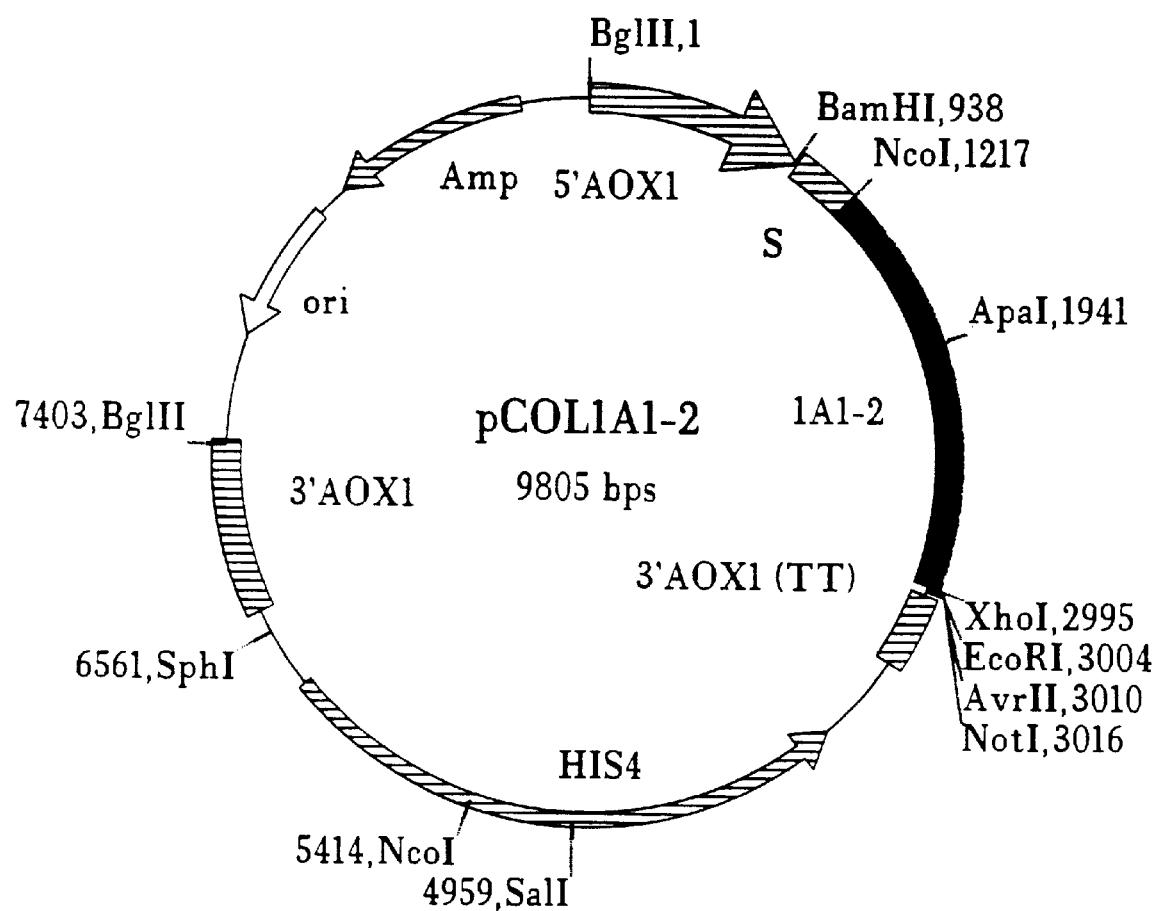

PCR has been carried out on Mouse 17-day Embryo QUICK-Clone™ cDNA (Clontech) in the same way as mouse COL1A1-1, using C1A1-FW and C1A1-RV2 primer. After denaturation at 94° C. for 4 minutes, 35 cycles were performed of 1 minute at 94° C., 1 minute at 65° C. and 3 minutes at 72° C. Final extension was at 72° C. for 10 minutes. Agarose gel electrophoresis shows a 1.8 kb band, which is the size predicted from the sequence. The further cloning of COL1A1-2 into the pPIC9 expression vector has been carried out in the same way as COL1A1-1, yielding pCOL1A1-2 (FIG. 9).

*Pichia pastoris* GS115 was transformed with the pCOL1A1-2 vector as described for the pCOL3A1 vector. Sal I-digested DNA was used in order to specifically generate Mut$^+$ transformants. Several transformants were used for small-scale expression in shaking flasks and one of those was selected for expression in the fermenter at a 1–100 L scale. FIG. 10 (SEQ ID NO: 48) shows the expected COL1A1-2 amino acid sequence. Typical yields are in the range of 4–5 g gelatin/L in the (extracellular) medium, at a dry biomass of 100–120 g/L (about 3 g gelatin/L overall). The target gelatin (FIG. 10) has a theoretical Mw of 53 kD. In agreement with this value (and with the known anomalous migration of gelatin in SDS-PAGE [10]), a SDS-PAGE band migrating at an apparent Mw of about 74 kD was observed (interpolated value obtained with globular protein Mw markers). In addition, tree shorter products with an apparent Mw of 56, 18 and 15 kD were observed (interpolated values). If the proteolytic cleavage would occur at corresponding sites in the COL1A1-1 and COL1A1-2 expression products (FIGS. 8, 10), fragments consisting of residue 1-595, 126-595, 1-125, and 42–125 of the COL1A1-2 product would be expected to occur. These would have theoretical Mw's of 53, 42, 12, and 8 kD, respectively, corresponding to apparent Mw's of 74, 58, 17 and 11 kD. Surprisingly, this corresponds well to the observed apparent Mw's, indicating that cleavage of COL1A1-2 was restricted mainly to the bond between residue 125 and 126, and (in addition), the bond between 41 and 42. Again, fragments corresponding to residue 1-41 (theoretical Mw 4 kD) and 42-595 (theoretical Mw 50 kD, apparent Mw 70 kD) were not observed. This could be due to a (much) more frequent cleavage between residue 125 and 126 than between residue 41 and 42, as mentioned for COL1A1-1.

Cloning and Expression of Mouse COL1A1-3

PCR has been carried out on Mouse 17-day Embryo QUICK-Clone™ cDNA (Clontech) in the same way as mouse COL1A1-1, using C1A1-FW and C1A1-RV3 primer. After denaturation at 94° C. for 4 minutes, 35 cycles were performed of 1 minute at 94° C., 1 minute at 65° C. and 3 minutes at 72° C. Final extension was at 72° C. for 10 minutes. Agarose gel electrophoresis shows a 2.8 kb band, which is the size predicted from the sequence.

Figure 11:
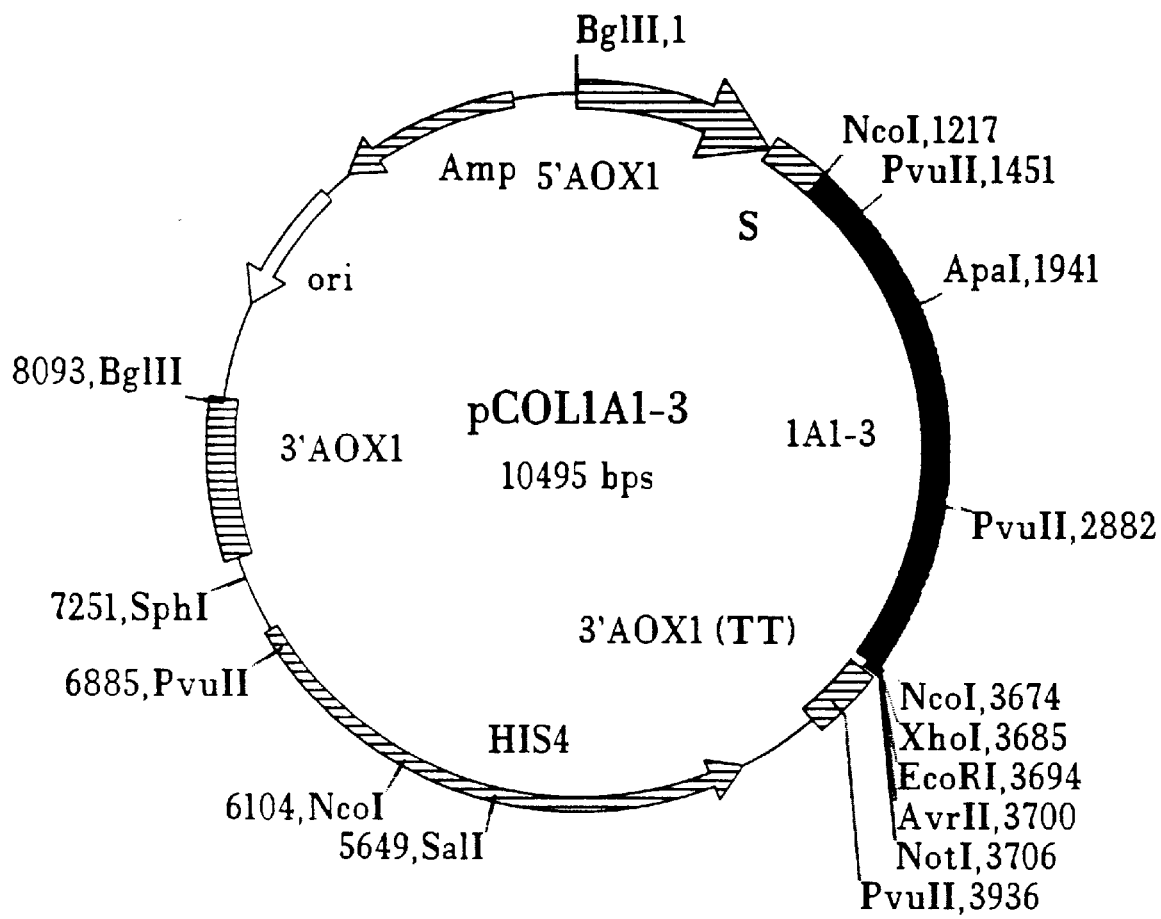

The PUC18* plasmid was digested with NcoI and dephosphorylated. The C1A1-FW/C1A1-RV3 PCR product was digested with NcoI and the resulting 2.5 kb fragment was gel purified and ligated into the NcoI digested and dephosphorylated vector. After transformation of *E. coli* XL1Blue, correct orientation of the insert in the resulting clones was verified by PvuII digestion. The further cloning of COL1A1-3 into the pPIC9 expression vector has been carried out in the same way as described for COL1A1-1, yielding pCOL1A1-3 (FIG. 11).

*Pichia pastoris* GS115 was transformed with the pCOL1A1-3 vector as described for the pCOL3A1 vector. Sal I-digested DNA was used in order to specifically generate Mut⁺ transformants. Several transformants were used for small-scale expression in shaking flasks and one of those was selected for expression in the fermenter at a 1–100 L scale. FIG. 12 (SEQ ID NO: 49) shows the expected COL1A1-3 amino acid sequence. Typical yields are in the range of 4–5 g gelatin/L in the extracellular compartment (determined after acetone fractionation, as described below), at a dry biomass of 100–120 g/L (about 3 g gelatin/L overall). The target gelatin (FIG. 12) has a theoretical Mw of 72 kD. In agreement with this value, an SDS-PAGE band migrating at an apparent Mw of about 100 kD was observed (interpolated value obtained with globular protein Mw markers). In addition, three shorter products with an apparent Mw of 85, 18 and 15 kD were observed (interpolated values). If the proteolytic cleavage would occur at homologous sites in the COL1A1-1 and COL1A1-3 expression products (FIGS. 8, 12), fragments consisting of residue 1-812, 126-812, 1-125, and 42-125 of the COL1A1-3 product would be expected to occur. These would have theoretical Mw's of 72, 60, 12, and 8 kD, respectively, corresponding to apparent Mw's of 100, 84, 17 and 11 kD. Surprisingly, this corresponds well to the observed apparent Mw's, indicating that cleavage of COL1A1-3 was restricted mainly to the bond between residue 125 and 126, and (to a lesser extent), the bond between 41 and 42. Again, fragments corresponding to residue 1-41 (theoretical Mw 4 kD) and 42-812 (theoretical Mw 68 kD, apparent Mw 96 kD) were not observed. This could be due to a (much) more frequent cleavage between residue 125 and 126 than between residue 41 and 42, as mentioned for COL1A1-1.

Table 1 summarizes the apparent COL1A1 fragment sizes derived by comparison with molecular weight marker proteins (LMW Calibration kit; Pharmacia), together with the size calculated from the sequence.

TABLE 1

Apparent and theoretical molecular weights of COL1A1 fragments

| Apparent molecular weight on SDS-PAGE gel | Molecular weight corrected for 40% slower migration | Residue | Molecular weight calculated from the sequence | Gene product |
| --- | --- | --- | --- | --- |
| 100 kD | 71 kD | 1-812 | 72 kD | (1A1-3) |
| 85 kD | 61 kD | 125-812 | 61 kD | (1A1-3) |
| 74 kD | 53 kD | 1-595 | 54 kD | (1A1-2) |
| 56 kD | 40 kD | 125-595 | 42 kD | (1A1-2) |
| 38 kD | 27 kD | 1-310 | 28 kD | (1A1-1) |
| 24 kD | 17 kD | 125-310 | 16 kD | (1A1-1) |
| 18 kD | 13 kD | 1-125 | 12 kD | (1A1-1,2,3) |
| 15 kD | 11 kD | 42-125 | 8 kD | (1A1-1,2,3) |

It is clear from table 1 that the 'MGPR' model fits the actual found fragment sizes well.

One would also expect fragments of residue 1-41 (4 kD; 1A1-1,2,3)) and 42-310 (theoretical Mw: 24 kD apparent Mw: 34 kD; 1A1-1), 42-595 (theoretical Mw: 50 kD apparent Mw: 70 kD; 1A1-2), or, 42-595 (theoretical Mw: 68 kD apparent Mw: 96 kD; 1A1-3). The fact that these fragments are not seen on gel, may be explained by assuming that the rate of cleavage at the second 'MGPR' site is much higher than that at the first site. This means that if the protein molecule is cut, it will always first occur at the second site. This difference in cleavage rates may be explained by the fact that the first site is preceded by a proline residue which may sterically hinder the protease.

Mouse COL1A1-1, COL1A1-2 AND COL1A1-3 'RGPM' (SEQ ID NO: 16) Mutants

We considered the possibility that the same amino acid sequence, functioning as recognition site for proteolytic enzyme(s), would be responsible for the degradation of all COL1A1 products (COL1A1-1, COL1A1-2, COL1A1-3). Surprisingly, both internal N-terminal sequences obtained from the 15 kD and 24 kD COL1A1-1 fragments were preceded by the same sequence 'MGPR'. Moreover, this sequence occurs only twice in the mouse COL1A1-1, COL1A1-2, or COL1A1-3 genes, viz. at residue 83-41 and 122-125. (As compared to COL1A1-1, COL1A1-2 and COL1A1-3 do not contain additional MGPR-sites). Also, the COL3A1 fragment from the rat did not contain such a site. This corresponds nicely to the observed cleavage pattern. Therefore, we think that 'MGPR' (SEQ ID NO: 14) is a motif recognized by a specific protease, resulting in the cleavage of the COL1A1 proteins. This MGPR (SEQ ID NO: 14) protease recognition site has not been described previously. A more generalized representation of the motif could possibly be MXXR, MXX[RK], or even [MLIV]XX [RKH](SEQ ID NO: 17). The former motifs are indeed present only twice in the entire mouse COL1A1 gene and are absent in the COL3A1 fragment, while the latter motif is so broad that it includes non-cleaved sites: MKGH (SEQ ID NO: 18) at residue 85-88 and VGAK (SEQ ID NO: 19) at residue 169-172 in COL1A1, and IKGH (SEQ ID NO: 20) at residue 198-201 in COL3A1. Thus, MXXR or MXX[RK] are more likely generalized motifs than [MLIV]XX[RKH (SEQ ID NO: 17). FIG. 13 (SEQ ID NO: 50) shows the 'MGPR' (SEQ ID NO: 14) motifs in the COL1A1-2 sequence. It is to be expected that this proteolytic cleavage site is only recognized by the enzymes involved if it occurs in relatively open, unfolded structures (like in our gelatin), but not so easily in more compactly folded structures (like in globular proteins). Thus, it may be important only in certain classes of proteins and polypeptides, including gelatins and unfolded collagens.

In order to be able to produce full-length COL1A1-1, COL1A1-2 AND COL1A1-3 without the occurrence of the three other main bands, the 'MGPR' (SEQ ID NO: 14) motifs should be removed by site-directed mutagenesis. In order to maintain the original amino acid composition of natural COL1A1 gelatin, the 'MGPR' (SEQ ID NO: 14) motif was removed by converting it to 'RGPM' (SEQ ID NO: 16). Two pairs of complementary primers were synthesized:

COL1A1MUT1FW:
R G P M (SEQ ID NO: 16)
5'-GAG-CCT-GGC-GGT-TCA-GGT-CCA-<u>CGA</u>-GGT-CC A-<u>ATG</u>-GGT-CCC-CCT-GG-3' (SEQ ID NO: 21)
COL1A1MUT1RV:
5'-CC-AGG-GGG-ACC-<u>CAT</u>-<u>TGG</u>-ACC-TCG-TGG-ACC-TGA-ACC-GCC-AGG-CTC-3' (SEQ ID NO: 22)
COL1A1MUT2FW:
R G P M (SEQ ID NO: 16)
5'-GGA-GCT-CCT-GGC-CAG-<u>CGA</u>-GGT-CCA-<u>ATG</u>-GGT-CTG-CCC-GGT-GAG-AG-3' (SEQ ID NO: 23)
COL1A1MUT2RV:
5'-CT-CTC-ACC-GGG-CAG-ACC-<u>CAT</u>-<u>TGG</u>-ACC-TCG-CTG-GCC-AGG-AGC-TCC-3' (SEQ ID NO: 24)

Note: mutant positions are underlined; the original C of the Pro residue has been converted itno A to avoid die generation of an NcoI site. Three primer combinations were used:
1. 5'AOX1 primer and COL1A1MUT1RV
2. COL1A1MUT1FW and COL1A1MUT2RV
3. COL1A1MUT2FW and 3'AOX1

The reactions contained: 1.25 U Pwo polymerase (Eurogentec), 50 pmol of each primer, 0.2 mM dNTPs (Pharmacia), 1×Pwo buffer (Eurogentec) and 15 ng pCOL1A1-1 template DNA in a total reaction volume of 50 µl. The PCR-machine used was the GeneAmp 9700 (Perkin-Elmer). After an initial incubation at 94° C. for 5 minutes, 18 cycles were performed consisting of 30 seconds at 94° C., 30 seconds at 60° C. and 45 seconds at 72° C. Final extension was performed at 72° C. for 10 minutes. Agarose electrophoresis of the PCR-reactions revealed products of the expected sizes (0.5, 0.3 and 0.7 kb respectively). The bands were cut out from the gel and purified. The isolated fragments were then subjected to overlap-extension PCR. Approximately 0.1 pmol of each fragment was mixed together. 50 pmol of 5'AOX1 and 3'AOX1 primer were added, as well as Pwo polymerase, dNTPs and buffer as described above. Cycling conditions were the same as described above with the exception that extension at 72° C. was performed for 90 seconds instead of 45 seconds. Agarose gel electrophoresis revealed the expected 1.5 kb product. The remainder of the PCR reaction was purified using the QIAquick PCR Purification Kit (Qiagen). The purified DNA was then digested with BamHI/ApaI, after which the resulting 1.0 kb fragment was purified from gel. *E.coli* strain JM110 was transformed with pCOL1A1-1, pCOL1A1-2 and pCOL1A1-3, in order to remove the dcm methylation of the ApaI site. After DNA isolation, the plasmids were digested with BamHI/ApaI. The resulting vector fragments of 7.9, 8.8 and 9.5 kb, respectively, were purified from agarose gel and ligated to the BamHI/ApaI digested PCR-product. *E. coli* XL1-Blue was transformed with these ligation reactions and plasmid DNA of PCR-verified insert containing clones was isolated and verified by automated sequencing. The mutant plasmids pCOL1A1-1*, pCOL1A1-2* and pCOL1A1-3* thus created were digested with SalI and used to transform *Pichia pastoris* strain GS(115. Small- and fermentor-scale expression was performed as described for COL1A1-1.

The SDS-PAGE analysis clearly shows that only one major band of the expected full-length size is formed, for COL1A1-1* as well as COL1A1-2* and COL1A1-3*.

Construction and Expression of Synthetic Gene.

A synthetic gene, encoding a polar gelatin (P monomer) was constructed by overlap extension PCR. The theoretical molecular weight and isoelectric point are 9.1 kD and 4.9, respectively. The gene was designed to have the codon usage of *Pichia pastoris* highly expressed genes (Sreekrishna, K. and Kropp, K. E. (1996) *Pichia pastoris*, Wolf, K. (Ed), Nonconventional yeasts in biotechnology. A handbook, Springer-Verlag, pp. 6/203–6/253). Two separate PCR reactions were performed, using the following oligonucleotides:
1 pmol OVL-PA-FW, 1 pmol OVL-PA-RV, 50 pmols HLP-PA-PW and 50 pmols HLP-PA-RV.
1 pmol OVL-PB-FW, 1 pmol OVL-PB-RV, 50 pmols HLP-PB-FW and 50 pmols HLP-PB-RV.

Oligonucleotide sequences were as follows:
H L P - PA - F W :
5'-GCGCTCGAGAAAAGAGAGGCTGAAGC-3' (SEQ ID NO: 25)
OVL-PA-FW:
5'-GCGCTCGAGAAAAGAGAGGCTGAAGCTGGT-CCACCCGGTGAGCCAGGTAACCCAGGATCTC-CTGGTAACCAAGGACAGCCCGGTAACAAGG-GTTCTCCAGGTAATCCA-3' (SEQ ID NO: 26)
OVL-PA-RV:
5'-TGAGAACCTTGTGGACCGTTGGAACCTGGCT-CACCAGGTTGTCCGTTCTGACCAGGTTGACCA-GGTTGACCTTCGTTTCCTGGTTGACCTGGATT-ACCTGGAGAACCCTT-3' (SEQ ID NO: 27)
H L P - PA - RV :
5'-TGAGAACCTTGTGGACCGTTGGAA-3' (SEQ ID NO: 28)
H L P - P B - F W :
5'-TTCCAACGGTCCACAAGGTTCTCA-3' (SEQ ID NO: 29)
OVL-PB-FW:
5'-TTCCAACGGTCCACAAGGTTCTCAGGGTAAC-CCTGGAAAGAATGGTCAACCTGGATCCCCAG-GTTCACAAGGCTCTCCAGGTAACCAAGGTTC-CCCTGGTCAGCCAGGTAACCCT-3' (SEQ ID NO: 30)
OVL-PB-RV:
5'-GCGTCTGCAGTACGAATTCTATTAGCCACCGG-CTGGACCCTGGTTTCCTGGTTTACCTTGTTCA-CCTGGTTGACCAGGGTTACCTGGCTGACCAG-GGGAACCTTGGTT-3' (SEQ ID NO: 31)
H L P - P B - R V :
5'-GCGTCTGCAGTACGAATTCTATTAGC-3' (SEQ ID NO: 32)

The 50 µl PCR reactions contained 0.2 mM dNTP's (Pharmacia), 1×Pwo buffer (Eurogentec) and 1.25 U Pwo polymerase (Eurogentec). Reaction 1 involved 18 cycles consisting of 15 seconds at 94° C. and 15 seconds at 72° C. Reaction 2 involved a touchdown PCR, whereby each cycle consisted of 15 seconds at 94° C., 15 seconds at the annealing temperature and 15 seconds at 72° C. The annealing temperature was lowered from 72° C. to 68° C. in the first 5 cycles, after which 20 additional cycles at an annealing temperature of 67° C. were performed.

The PCR products were isolated from agarose gel. 0.3 pmols of each fragment and 50 pmols of the outer primers HLP-PA-FW and HLP-PB-RV were subjected to overlap extension PCR. 25 cycles consisting of 15 seconds at 94° C., 15 seconds at 67° C. and 15 seconds at 72° C. were performed. The resulting 0.3 kb PCR fragment was digested with XhoI/EcoRI and cloned in cloning vector pMTL23. The sequence of the gene was verified by automated DNA sequencing.

In order to create a P tetramer (P4; theoretical molecular weight 36.8 kD), the fragment was released by digesting the vector with DraIII/Van91I. In a separate reaction the vector was digested with Van91I and dephosphorylated. The DraIII/Van91I fragment was then inserted into this Van91I digested vector. This yielded a vector containing a P dimer. This dimer was released by digestion with DraIII/Van91I and reinserted into the Van91I site of the dimer bearing vector, yielding the P tetramer (P4). The P and P4 fragments were then cloned into the XhoI/EcoRI sites of vector pPIC9. The encoded amino acid sequence of the mature (processed) P monomer and tetramer are as follows:
Monomer (P): (SEQ ID NO: 33)

gelatins (i.e. removal of endogenous proteins at 40% acetone and precipitation of gelatin at 80% acetone).

Expression/Production of Gelatin in a Fermentor

Fed-batch fermentations were performed according to the Pichia fermentation process guidelines of Invitrogen. Cells were grown in a 1-liter fermentor (Applikon) in the initial experimental stages to optimize protein production. Thereafter cells were grown in a 20-liter or a 140-liter fermentor (Biobench 20, Bio-pilot 140, Applikon) for pilot scale production of collagen. Working volumes were 1-liter, 15-liter and 100-liter, respectively. AD1020 controllers (Applikon) were used to monitor and control the fermentation parameters. The program BioXpert (Applikon) was used for data storage. Dissolved oxygen levels were monitored in the fermentor using an oxygen electrode (Ingold for 1-liter fermentations, Mettler Toledo for larger scale fermentations). Agitation (500–1000 rpm) and aeration (1–2 vvm, i.e. 1–2 $LL^{-1}min^{-1}$) were manually adjusted to keep the dissolved oxygen concentration above 20%. pH was measured by a pH electrode (Broadly James cooperation) and automatically kept at pH 3.0 or pH 5.0 by addition of ammonium hydroxide (25%), which also served as nitrogen source for growth of the microorganisms. An anti foam-electrode was used to prevent excessive foaming. When necessary, the anti foam Structol J673 (Schill and Seilacher, Hamburg, Germany) was used. Growth of the microorganisms was monitored by determination of the cell dry weight. A calibration curve was made by which cell wet weight could be converted into cell dry weight. Cell wet weight was determined after centrifugation of 2 ml-samples for 5 min at 15.000 rpm and removing the supernatant. Cell dry weight

```
  1 GPPGEPGNPG SPGNQGQPGN KGSPGNPGQP GNEGQPGQPG QNGQPGEPGS NGPQGSQGNP

61 GKNGQPGSPG SQGSPGNQGS PGQPGNPGQP GEQGKPGNQG PAGG
```

Tetramer (P4): (SEQ ID NO: 34)

was determined after addition of 200 µl of cells to a

```
  1 GPPGEPGNPG SPGNQGQPGN KGSPGNPGQP GNEGQPGQPG QNGQPGEPGS NGPQGSQGNP

61 GKNGQPGSPG SQGSPGNQGS PGQPGNPGQP GEQGKPGNQG PAGEPGNPGS PGNQGQPGNK

121 GSPGNPGQPG NEGQPGQPGQ NGQPGEPGSN GPQGSQGNPG KNGQPGSPGS QGSPGNQGSP

181 GQPGNPGQPG EQGKPGNQGP AGEPGNPGSP GNQGQPGNKG SPGNPGQPGN EGQPGQPGQN

241 GQPGEPGSNG PQGSQGNPGK NGQPGSPGSQ GSPGNQGSPG QPGNPGQPGE QGKPGNQGPA

301 GEPGNPGSPG NQGQPGNKGS PGNPGQPGNE GQPGQPGQNG QPGEPGSNGP QGSQGNPGKN

361 GQPGSPGSQG SPGNQGSPGQ PGNPGQPGEQ GKPGNQGPAG G
```

In order to prevent possible C-terminal degradation of the P and P4 gelatins, constructs were created that have identical sequences as P and P4, but which have a C-terminal Pro instead of a Gly residue (PC and P4C, respectively).

The vectors were linearized by digestion with SalI and were used to transform Pichia pastoris strain GS115. Fermentations were performed as described for COL1A1 (i.e. growth at pH 3 and in the presence of casamino acids). Culture supernatants were analyzed by SDS-PAGE and revealed protein bands having the expected N-terminal amino acid sequences. The yield was calculated to be 1 gram/liter fermentation medium. The products could be purified by acetone fractionation as described for the native pre-dried filter (0.45 µm membrane, Schleichner & Schüll, Dassel, Germany), washing with 25 ml of deionized water and drying e.g. in a microwave oven for 15 minutes at 1000 W. Cell dry weight was approximately a factor 3 lower than cell wet weight, Precultures were started from colonies on a MGY plate, in flasks containing a total of 10% of the initial fermentation volume of MGY. The volume of the medium was ≦20% of the total flask volume. Cells were grown at 30° C. at 200 rpm in a rotary shaker (Gallenkamp) for 24–60 hours.

Fermentation Medium

The fermentation basal salts medium in the fermentor contained per liter: 26.7 ml of phosphoric acid (85%), 0.93 g calcium sulfate, 18.2 g potassium sulfate, 14.9 g magnesium sulfate.7H$_2$O, 4.13 g potassium hydroxide and 40.0 g glycerol. An amount of 4.3 ml of PTM$_1$ trace salts was added per liter of fermentation basal salts medium. PTM$_1$ trace salts contained per liter: 4.5 g cupric chloride.2H$_2$O, 0.09 g potassium iodide, 3.5 g manganese chloride.4H$_2$O, 0.2 g sodium molybdate.2H$_2$O, 0.02 g boric acid, 1.08 g cobalt sulfate.7H$_2$O, 42.3 g zinc sulfate.7H$_2$O, 65.0 g ferrous sulfate.7HO, 0.2 g biotin and 5.0 ml sulfuric acid. Trace salts were filter sterilized (pore size 0.22 µm, Costar, USA). Casamino acids (caseine hydrolysate Merck) were separately sterilized and added to the fermentation medium in an amount of 5 g/l when collagen type I from the mouse was expressed (COL1A1-1, COL1A1-1*, COL1A1-2, COL1A1-2*, COL1A1-3, COL1A1-3*). During the fermentation after 50 hours a further amount of 5 g/l of sterile casamino acids was added to the fermentation medium.

Fermentation of Mut$^+$ Cultures

The fermentor was sterilized with the fermentation basal salts medium. The 20-liter and 120-liter fermentor were sterilized in situ with initial medium volumes of 5–7.5 l and 50-liter, respectively. The 1-liter fermentor was sterilized with 500 ml medium in an autoclave. After sterilization the temperature was set at 30° C., agitation and aeration were set at 500 rpm and 1 vvm (i.e. 1 LL$^{-1}$ min$^{-1}$), respectively. The pH was adjusted to set point (usually pH 5.0) with 25% ammonium hydroxyde. Trace salts were aseptically added to the medium. The fermentor was inoculated with 10% of the initial fermentation volume of precultured cells in MGY. The batch culture was grown until the glycerol was completely consumed (18–24 hours). This was indicated by an increase of the dissolved oxygen concentration to 100%. Cell dry weight was 25–35 g/l in this stage. Thereafter the glycerol fed-batch phase was started by initiating a 50% (v/v) glycerol feed containing 12 ml PTM$_1$ trace salts per liter of glycerol. The glycerol feed was set at 18 ml/h/liter initial fermentation volume. The glycerol feed was carried out for 4 hours, or overnight in the case of a long lag phase. During the glycerol batch phase the pH of the fermentation medium was lowered to 3.0. The protein induction phase was initiated by starting a 100% methanol feed containing 12 ml PTM$_1$ trace salts per liter of methanol. The feed rate was set to 3 ml/h/liter initial fermentor volume. During the first hours methanol accumulated in the fermentor. After 2–4 hours dissolved oxygen levels decreased due to adaptation to methanol. The methanol feed was increased to 6 ml/h/initial fermenter volume in the case of a fast dissolved oxygen spike. If the carbon source is limiting, shutting of the carbon source causes the culture to decrease its metabolic rate and the dissolved oxygen concentration rises (spike). After an additional 2 hours the methanol rate was increased to 9 ml/h/liter initial fermentor volume, This feed rate was maintained throughout the remainder of the fermentation. The fermentation was stopped after 70–130 h methanol fed-batch phase. During the fermentation samples were taken of 2 ml, centrifuged (5 min, 15.000 rpm) and the supernatant was stored at −20° C.

Concentration of gelatin and total protein was determined after filtration of the samples (0.22 µm) and subsequent acetone fractionation (40 vol-%, followed by 60–80 vol-% acetone). The BCA protein assay (Pierce) was routinely used, with gelatin from Merck as a reference. According to SDS-PAGE and analysis of the amino acid composition, the non-collagenous proteins precipitated at 40% acetone, while the COL3A1 and COL1A1 fragments precipitated at 60–80%. At 60% acetone, preferentially the higher molecular weight gelatin components precipitated. At increasing acetone concentration, increasing precipitation was obtained for the main degradation products described above. At 80%, all of the main degradation products were recovered in the precipitate (as checked with SDS-PAGE). Small, peptides and other low molecular weight contaminants remained in solution at 80% acetone.

At the end of the fermentation, the cells were removed by centrifugation (10,000 rpm, 30 min, 4° C.) in the case of the 1-liter fermentation. Cells were removed by micro filtration in the case of the 20-liter fermentation. The cell broth was first applied to a micro filtration module containing a polyether sulfone membrane with 0.50 µm pore size (type MF 05 M2 from X-Flow, fitted in a RX 300 filtration module from X-Flow). Thereafter the supernatant was applied to a similar type of micro filtration module containing a polyether sulfone membrane with 0.2 µm pore size (type MF 02 M1, similarly from X-Flow). In the case of the 120-liter fermentation cells were removed by a pilot plant scale micro filtration unit containing a polyether sulfone membrane with 0.2 µm pore size (type MF 02 M1, from X-Flow, fitted into a R-10 membrane module). These filtration units are mentioned merely as examples. It will be understood that any suitable micro filtration system could be applied to remove the cells. Optionally, the bulk of cells and debris was removed by centrifugation, and only the supernatant and the medium used to wash the cells was applied to the microfiltration units. Alternatively, it is possible to recover the product from the fermentation broth and separate it from the cells by directly applying the fermentation broth to a suitable expanded bed chromatography system, using a resin that specifically binds the gelatin produced. We successfully used SP Sepharose XL Streamline from Pharmacia as a cation exchanger in expanded bed mode, at pH 3–4.

Fermentation of Mut$^s$ Cultures

Glycerol batch and fed-batch phase were performed as described for the mut$^+$ cultures. Since Mut$^s$ cultures metabolize methanol poorly, their oxygen consumption is very low. Therefore spikes of the dissolved oxygen concentration cannot be used to evaluate the culture. The methanol feed was adjusted to maintain an excess of methanol in the medium which does not exceed 0.3%. The methanol feed was initiated at 1 ml/h/liter initial fermentor volume and increased slowly to 3 ml/h/liter. The total fermentation time required when using Mut$^s$ cultures was comparatively longer than when Mut$^+$ cultures were used.

Preparative Purification of Collagen/Gelatin on a Preparative Scale

After the micro filtration step, two alternative purification strategies were followed (see I, II below).

I. Purification by Differential Precipitation

Acetone Fractionation

Collagen type I and type III were partly purified from batches of 500 ml to 2 liter of supernatant by a 40–80% acetone fractionation. At 40% acetone, the non-collagenous proteins (from Pichia) were precipitated, while at 60–80% acetone, collagen as well as collagen breakdown products were precipitated, as shown by SDS-PAGE and analysis of the amino acid composition. At 60% acetone, preferentially the higher molecular weight gelatin components precipitated. At increasing acetone concentration, increasing precipitation was obtained for the main degradation products described above. At 80%, all of the main degradation products were recovered in the precipitate (as checked with SDS-PAGE). Small peptides and other low molecular weight contaminants remained in solution at 80% acetone. Acetone was cooled for 2–4 hours at −20° C. An amount of 40% of ice-cold acetone (v/v) was added slowly to the precooled supernatant from the fermentation at 4° C. under magnetic stirring. Supernatant was stirred overnight at 4° C. Precipitated proteins and particles were removed by centrifugation (4° C., 10,000 rpm, 30 min). The pellet was resuspended in 40% ice-cold acetone and again centrifuged. Both 40% acetone supernatant fractions were pooled. Thereafter the supernatant was brought to 60–80% acetone (v/v) and stirred overnight. Precipitated proteins were collected by centrifugation. The pellet was resuspended in 60–80% acetone and centrifuged again. The pellet was dissolved in an appropriate amount of a 5 mM acetic acid/ammonium hydroxide buffer at pH 3.0 (buffer A) to a protein concentration of 20–50 g/l.

Ammonium Sulphate Precipitation

Polysaccharides were subsequently removed by precipitation of the gelatin/collagen at 60% saturation of ammonium sulphate, where the polysaccharides remained in solution. Ammonium sulphate was slowly added to 60% saturation at 4° C. After 60 min stirring the sample was centrifuged (30 min, 4° C., 10,000 rpm). The pellet was resuspended in 60% ammonium sulphate and again centrifuged. If more than 1% (w/w) polysaccharides or sugars remained present, the complete ammonium sulphate precipitation procedure described above was repeated after complete redissolution of the gelatin/collagen in the absence of ammonium sulphate. Finally, the pellet was dissolved in deionized water or in buffer A to a protein concentration of 20–50 g/l. The pH of the sample was adjusted to 3.0. The sample was desalted by dialysis against buffer A, which was refreshed every 4 hours. Dialysis membranes of regenerated cellulose (Spectra Por®, from Spektrum) were used with a molecular weight cut-off of 8 kD. The dialysis was stopped after 2–7 days at the moment that the conductivity of the sample was judged to be sufficiently low (typically 20–150 $\mu$S.cm$^{-1}$ above background). Conductivity was measured with a digital conductivity meter (Radiometer), calibrated with 1 mM and 10 mM KCl solutions (140 and 1400 $\mu$S.cm$^{-1}$, respectively). As an alternative to dialysis, ultrafiltration and diafiltration were used to desalt the samples and (optionally) to concentrate them. Where applicable, the product was subsequently pre-dried (optional) by precipitation with high concentrations of acetone and evaporation of the acetone, and finally freeze-dried.

Purification by Cation-exchange Chromatography

The cation-exchange resin was SP Sepharose XL (Pharmacia Biotech), but other suitable resins could also be used. The purification was carried out at several scales. Thus, 25 mL bed in a XK16 column (Pharmacia) was used. Runs were performed with a FPLC (Pharmacia). Bed height was 12.5 cm. Flow rates were typically 1 ml/min. At an intermediate scale, a 100 mL bed was used, runs being controlled by an Äkta Explorer integrated pump/processor/multiple valve/multiple detector unit (Pharmacia). On pilot scale a 2 liter bed in an Index 140/200 column was used. Bed height was at least 13 cm. Runs were performed with the ÄKTA explorer pump-processor unit (Pharmacia) or other pump systems. Flow rates were 50–100 ml/min, or higher. As an example, the following buffer system and elution conditions were used. Buffer X was a 5 mM citric acid buffer at pH 3.2, buffer Y a 5 mM citric acid buffer with 1 M NaCl at pH 3.0. The column was equilibrated with 2–5 bed volumes of buffer X. The protein of interest was eluted with a linear gradient of 0–0.5 M NaCl in 5–10 column volumes. The main band of collagen type III eluted at 50–100 mM NaCl. The main band of collagen type I eluted at 70 mM NaCl, the other bands between 30–150 mM NaCl, in agreement with their theoretical isoelectric points. The column was cleaned with 1 bed volume of buffer Y. On a pilot scale the pooled fractions were desalted and concentrated, e.g. by addition of 80% acetone, and subsequently freeze-dried.

Characterization of the Gelatin/Collagen Product

The amino acid composition was determined after complete HCl-mediated hydrolysis of the peptide bonds at very low pH and elevated temperature, followed by derivatisation of the amino acids with a fluorophore, and HPLC.

The percentage Gly expected from pure collagen is 33%. This offers a means of estimating the purity of produced recombinant gelatins. In order to correct for the percentage of Gly in endogenously secreted proteins of *Pichia pastoris*, amino acid composition analysis was performed on fermentation supernatant of a Mut$^+$ transformant of pPIC9. The percentage Gly found was 9%. The purity of a sample can now be estimated by the formula:

(%Gly−9)/(33−9)=(%Gly−9)/24.

After dissolution of samples in MilliQ water, the following assays were performed.

The protein content was determined by the BCA assay from Pierce, using gelatin from Merck as a reference.

The protein Mw distribution was determined by SDS-PAGE.

The sugar content was determined by a phenol-based assy. 200 $\mu$L samples were mixed with 200 $\mu$L 5% (w/w) phenol. After thorough mixing using a Vortex mixer, 1 mL of concentrated sulphuric acid was added. After mixing, the samples were incubated for 10 min at room temperature and, subsequently, for 20 min. at 30° C. After cooling, the light absorption of the samples at 485 nm was determined. Starch, glucose and sucrose were used to prepare calibration curves.

The DNA content was determined by mixing aliquots of diluted SYBR® Gren I nucleic acid "gel" stain (10,000× conc. In DMSO) from Molecular Probes with our samples. After thorough spectral analysis, the excitation wavelength was chosen to be 490 nm, and the emission wavelength 523 nm. The calibration was by subsequent addition of known amounts of DNA to this same mixture, as internal standards. Thus, a calibration curve was constructed. Furthermore, it was checked that subsequent addition of DNA-degrading enzyme resulted in complete break down of the fluorescent signal.

A quantitative indication of the RNA plus DNA-content was subsequently obtained by using SYBR® Green II "RNA gel stain", instead of SYBR® Green I. After thorough spectral analysis, the excitation wavelength was chosen to be 490 nm, and the emission wavelength 514 nm. Calibration was by subsequent addition of known amount of RNA. The resulting value was denounced the "RNA" content of the sample. In the absence of DNA, it corresponded to the true RNA content. When present, the DNA-associated fluorescence may have biased the RNA values, although a final addition of RNAse was used to discern the DNA- and RNA-derived contributions to the fluorescence.

The conductivity of the samples was measured with a digital Radiometer conductivity meter, checking that 1 and 10 mM KCL solutions in MilliQ water gave readings of 140 and 1400 $\mu$S.cm$^{-1}$, respectively.

Data on Purity of Some Gelatin Batches Produced in Accordance with the Invention (examples)

GATO4a (col3a1)
    about 2.4 gram purification:
: micro filtration, precipitation (1×acetone fractionation (40%/80%), 1×(NH$_4$)$_2$SO$_4$), dialysis against 5 mM CH$_3$COOH/CH$_3$COO$^-$-buffer keeping the sample below pH 4 (initial pH about 3.5; buffer prepared by dilution from 500 mM acetic acid adjusted to pH 3.0 with 25% NH$_4$OH), lyophilization DNA: <1 ppm (w/w)

Figure 14:
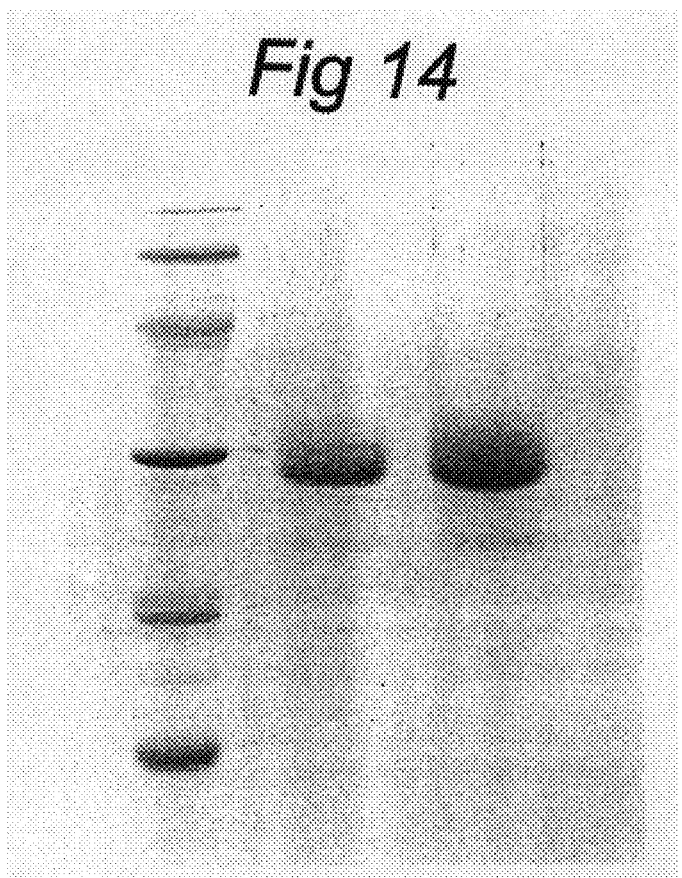

RNA: 12.7 ppm (w/w)

total sugars: 4.5% (w/w)

gelatin was not degraded during purification (SDS-PAGE: FIG. 14)

GATO4b (col3a1, further purified than GATO4a)
: about 1 gram
: purification:
  : further purified from GATO4a by repeated (2×additional) ammonium sulphate precipitation followed by dialysis against 5 mM CH$_3$COOH/CH$_3$COO$^-$-buffer keeping the sample below pH 4 (initial pH about 3.5; buffer prepared by dilution from 500 mM acetic acid adjusted to pH 3.0 with 25% NH$_4$O—H), lyophilization DNA: 0.56 ppm (w/w)

RNA: 3.2 ppm (w/w)

total sugars: 0.94% (w/w)

gelatin was not degraded during purification.

specific conductance after dialysis about 180 $\mu$Scm$^{-1}$ at 10 g gelatin/L (specific conductance of buffer about 100 $\mu$Scm$^{-1}$)

specific conductance after lyophilization and dissolving a sample: 180 $\mu$Scm$^{-1}$ at 10 g gelatin/L, 100 $\mu$Scm$^{-1}$ at 5 g gelatin/L GATO5 (col1a1-1)
: about 0.9 gram
: purification:
  : micro filtration, precipitation (1×acetone fractionation (40%/80%), 1×(NH$_4$)$_2$SO$_4$), dialysis against 5 mM CH$_3$COOH/CH$_3$COO$^-$-buffer keeping the sample below pH 4 (initial pH about 3.5; buffer prepared by dilution from 500 mM acetic acid adjusted to pH 3.0 with 25% NH$_4$OH), lyophilization DNA: <1 ppm (w/w)

Figure 15:
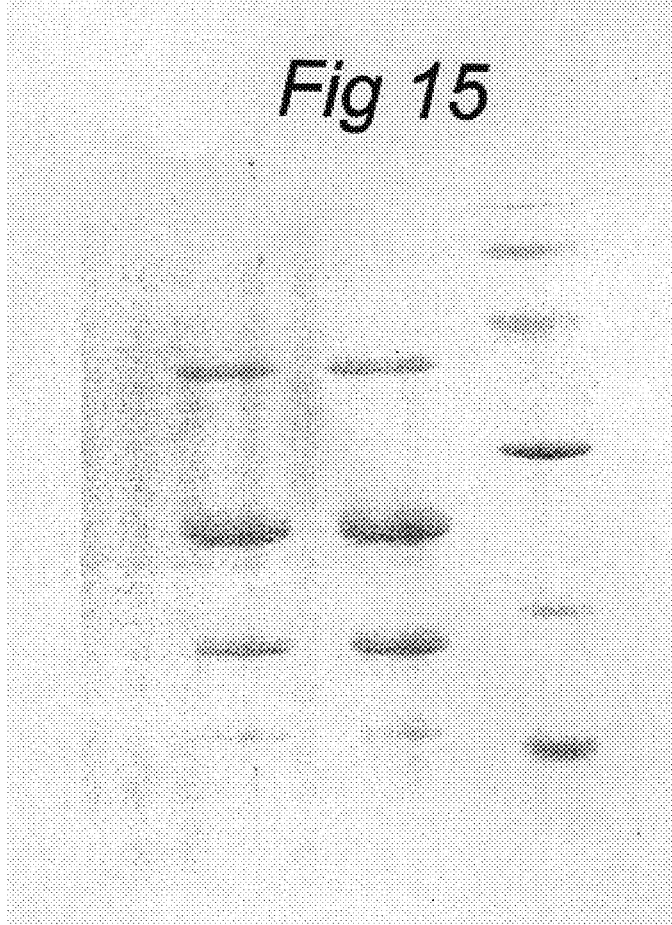

RNA: 87 ppm (w/w)

total sugars: 4.5% (w/w)

gelatin was not degraded during purification (SDS-PAGE: FIG. 15)

GATO6 (col3a1 purified by expanded bed cation exchange chromatography)
: about 50 mg
: purification:
  : expanded bed cation exchange chromatography at pH 3–3.5 (SP-Sepharose-XL "Streamline" resin from Pharmacia Biotech; sugar content after sub-optimal washing of the column and elution at 0.3 M NaCl: 1.8% (w/w)), further removal of sugar by a single (NH$_4$)$_2$SO$_4$-precipitation, followed by dialysis against 5 mM NH$_4^+$/CH$_3$COO$^-$-buffer (pH about 3.5), lyophilization DNA: <1 ppm(w/w, already before (NH$_4$)$_2$SO$_4$-precipitation and dialysis)

RNA: <9 ppm (w/w, already before (NH$_4$)$_2$SO$_4$-precipitation and dialysis)

total sugars: 1.1% specific conductance after dialysis about 94 $\mu$Scm$^{-1}$ at 0.55 g gelatin/L (specific conductance of buffer: about 100 $\mu$Scm$^{-1}$).

gelatin was not degraded during purification

GATO7 (col1a1-2)
: 400 mg
: purification:
  : micro filtration, precipitation (1×acetone fractionation (40%/71.5%), 3×(NH$_4$)$_2$SO$_4$), pre-desalting by acetone precipitations: 1×71.5%, 1×80%, dialysis against MilliQ water, lyophilization DNA: 0,79 ppm RNA: 9,5 ppm total sugars: 0.7% (w/w)

specific conductance after dialysis about 15.5 $\mu$Scm$^{-1}$ at 4 g gelatin/L gelatin was not degraded during purification GATO8 (col3a1)
: about 6 g
: purification.
  : microfiltration, dilution, cation exchange chromatography in a 2,1 litre bed SP Sepharose-XL from Pharmacia Biotech equilibrated with 20 mM citrate, pH 3,5 and elution at 0.15 M NaCl in the same buffer over a gradient of 0–1 M NaCl, concentration, partial desalination with 80% acetone, centrifugation, resolubilisation in MilliQ water, dialysis against MilliQ water and lyophilisation DNA: 1,55 ppm(w/w)

RNA: 10,9 ppm (w/w)

total sugars: 1.2% (w/w)

specific conductance after dialysis about 90 $\mu$Scm$^{-1}$ at 7,5 g gelatin/L gelatin was not degraded during purification FIG. 16 shows the result of purification.

GATO9 (col1a1-1)
: 1,7 g
: purification; see GATO8 with one difference i.e. elution from the cationic exchanger in a 1 salt step at 0,75 M NaCl.

DNA: <1 ppm (w/w)

RNA: 1,3 ppm (w/w)

total sugars: 2,2% (w/w)

specific conductance after dialysis about 70 $\mu$Scm$^{-1}$ at 12 g gelatin/L gelatin was not degraded during purification GATO10 (col1a1-2) wherein both MGPR sequences have been changed to RGPM
: 6 g
: purification: see GATO8

DNA: 0,04 ppm (w/w)

RNA: 2 ppm (w/w)

total sugars: 2% (w/w)

gelatin was not degraded during purification

N terminal amino acid sequence was as expected with Glu-Ala as N terminal extension due to incomplete removal of the propeptide.

The results are shown in FIG. 18.

In conclusion the amino acid composition of all samples matched the theoretical composition. The contamination with foreign protein was very low. On a glycine basis GATO4–GATO8 have less than 1% foreign protein as contaminant. GATO9 and GATO10 have less than 5%.

DESCRIPTION TO THE FIGURES

FIG. 1: vector pCOL3A1

FIG. 2: PCR primers for pCOL3A1 construct control

FIG. 3: The expected COL3A1 sequence. The N terminal Y is derived from the pPIC 9 vector. The rest of the sequence is derived from COL3A1 of the rat. The underlined sequences correspond to the N terminal sequences obtained for COL3A1 fragments.

FIG. 4: vector pCOL3A1K.

FIG. 5: Oligo sequences for cloning of COL1A1. The bootom sequence is the adaptor after annealing.

FIG. 6: Cloning strategy

FIG. 7: vector pCOL1A1-1

FIG. 8: The expected COL1A1-1 sequence. The singly underlined sequences correspond to the N terminal sequences obtained for COL1A1 fragments. The double underlined sequences share this sequence. Both fragment are extended at the N terminus by EA.

FIG. 9: vector pCOL1A1-2

FIG. 10: Expected COL1A1-2 sequence

FIG. 11: vector pCOL1A1-3

FIG. 12: Expected COL1A1-3* sequence

FIG. 13: MGPR sequence in the expected COL1A1-2 sequence. The singly underlined sequences correspond to the N terminal sequences obtained for COL1A1-1 fragments. The double underlined sequences is the MPPR sequence.

FIG. 14: SDS poly acryl amide gel electrophoresis of GATO4. The gel was stained with Coommassie Brilliant Blue. In the left most lane the molecular marker protein mix is visible. From top to bottom the bands correspond to molecular weights of 94,67,43,30,20 and 14,4 kD. The second and third lane from the left show GATO4 after purification.

FIG. 15: SDS poly acryl amide gel electrophoresis of GATO5. The gel was stained with Coommassie Brilliant Blue. In the right most lane the molecular marker protein mix is visible. From top to bottom the bands correspond to molecular weights of 94,67,43,30,20 and 14,4 kD. The second and third lane from the right show GATO5 after purification.

FIG. 16 SDS poly acryl amide gel electrophoresis of expression product col1A1-2. The gel was stained with Coommassie Brilliant Blue. In the left most lane the molecular marker protein mix is visible. From top to bottom the bands correspond to molecular weights of 94, 67, 43, 30, 20,1 and 14,4 Kd.

FIG. 17 SDS poly acryl amide gel electrophoresis of expression product col1A1-1 in which MGPR sequences have been mutated to RGPM. The gel was stained with Coommassie Brilliant Blue. In the left most lane the molecular marker protein mix is visible. From top to bottom the bands correspond to molecular weights of 94, 67, 43, 30, 20,1 and 14,4 kD.

FIG. 18 SDS poly acryl amide gel electrophoresis of expression product col1A1-2 in which MGPR sequences have been mutated to RGPM. The gel was stained with Coommassie Brilliant Blue. In the left most lane the molecular marker protein mix is visible. From top to bottom the bands correspond to molecular weights of 94, 67, 43, 30, 20,1 and 14,4 kD.

REFERENCES CITED IN EXAMPLE 1

[1] Capello, J. & Ferrari, F. (1994) in: Plastics from microbes (Mobley, D. P., ed.) Hanser, Munich, pp. 35–92

[2] Strausberg, R. L. & Link, R. P. (1990) TIBTECH 8: 53–57.

[3] Maniatis T., Fritsch, E. F. & Sambrook J. (1982) Molecular cloning: A laboratory manual. Cold Spring Harbor Laboratory, Cold Spring Harbor, N.Y.

[4] Manual of the Pichia Expression Kit Version E (Invitrogen, San Diego, Calif., USA).

[5] Glumoff, V., Mäkelä, J. K. & Vuorio, E (1994) Cloning of cDNA for rat proα1(III) collagen mRNA. Increased expression of type III collagen gene during induction of experimental granulation tissue. Biochim Biophys Acta 1217: 41–48.
EMBL/GenBank accession number X70369.

[6] Sanger, F., Nicklen, S. & Coulson, A. R. (1977) Proc. Natl. Acad. Sci. USA 74: 5463–5467.

[7] Becker, D. M. & Guarente, L. (1991) High efficiency transformation of yeast by electoporation. Methods in Enzymology, vol. 194: 182–187.

[8] Lee, F. J. S. (1992) Biotechniques 12 (5): 677

[9] Laemmli, U. K. (1970) Cleavage of structural proteins during the assembly of the head of bacteriophage T4. Nature 227: 680–685.

[10] Schmitt, M. E., Brown, T. A. and Trumpower, B. L. (1990) A rapid and simple method for preparation of RNA from *Saccharomyces cerevisiae*. Nucleic Acids Res. 18 (10): 3091.

[11] Scorer, C. A., Clare, J. J., McCombie, W. R., Romanos, M. A. & Sreekrishna, K. (1994) Rapid Selection using G418 of high copy number transformants of *Pichia pastoris* for high-level foreign gene expression. Bio/Technology 12: 181–184.

[12] Butkowsky R. J., Noelken, M. B. & Hudson, B. G. (1982) Estimation of the size of colagenous proteins by electrophoresis and gel chromatography. Meth. Enzymol. 82: 410–423.

[13] De Wolf, F. A. & Keller R. C. A (1996) Characterization of the helical structures in gelatin networks and model polypeptides by circular dichroism. Progr. Colloid Polym. Sci. 102: 9–14

Example 2 (control)

Preparation of Silver Bromide Crystals with Conventional Regular Type Gelatin.

Nucleation: At a temperature of 35° C. in a reaction vessel containing 2.1 g/l regular gelatin (a standard deionised IAG bone gelatin from PB Gelatins, Tessenderlo, Belgium) and 7.3 mM potassium bromide the pH is adjusted to a value of 5.5 by sodium hydroxide or sulphuric acid. By single jet addition an aqueous solution of 144 mM silver nitrate is added at a constant rate in a period of 10 sec while vigorously stirring. After addition of the silver nitrate the gelatin concentration in the reaction mixture has become 2.0 g/l and the bromide concentration 1 mM.

Ripening: After nucleation the content of the vessel is transferred to a ripening vessel, where the temperature is increased gradually to a value of 75 C and the bromide concentration is increased to 15 mmol/l by adding a 3.4 M potassium bromide solution. The ripening is continued for 56 minutes after which a standard deionised gelatin is added up to a concentration of 5 g/l; after 58 minutes the Ostwald ripening is strongly reduced by adding a solution of methyl phenyl tetrazole and cooling to room temperature. A sample of the prepared emulsion was analyzed by direct transmission electron microscopy as well as by replica thereof.

39

Result: As can be seen in table II very low % of tabular grains is formed.

Example 3 (control)
Preparation of Silver Bromide Crystals with Conventional Hydrolysed Gelatin.

Nucleation: The nucleation is performed applying the same conditions (also pH=5.5) as in example 2 except that the gelatin in the reaction mixture is replaced by a conventional hydrolysed gelatin sample (also deionised and supplied by Nitta Gelatin in Japan).

Ripening: The ripening is done according the same procedure as is used in example 2.

Result: A medium % tabular grains of ca 40% is shown in table II.

Example 4 (control)
Preparation of Silver Bromide Crystals with Oxidized Gelatin.

Nucleation: The nucleation is performed applying the same conditions (also pH=5.5) as in example 1 except that the gelatin in the reaction mixture is replaced by a conventional oxidized gelatin sample (supplied by PB Gelatins Tessenderlo in Belgium).

Ripening: The ripening is done according the same procedure as is used in example 2.

Result: A high % tabular grains of 70% with an average aspect ratio of 5:1 is shown in table II for the oxidized gelatins at pH 5.5. The better result than with the hydrolysed and regular gelatin is to be explained due to the lower methionine content of this gelatin (11 $\mu$mol/gram gelatin vs. 50–60 $\mu$mol/gram for the conventional gelatins).

Example 5 (this invention)
Preparation of Silver Bromide Crystals with Invented Native Recombinant Gelatins.

Nucleation: The nucleation is performed applying the same conditions (also pH=5.5) as in example 2 except that the gelatin in the reaction mixture is replaced by the invented native COL3A1 gelatin sample.

Ripening: The ripening is done according to the same procedure as is used in example 2.

Result: A high % tabular grains of more than 85% with an average aspect ratio of 5:1 is shown in table II.

Example 6 (control)
Preparation of Silver Bromide Crystals with Conventional Regular Gelatin at Different pH (Standard deionised IAG bone gelatin from PB Gelatins, Tessenderlo in Belgium).

Nucleation: the nucleation is performed applying a pH=7 condition while the other conditions remained the same as in example 2.

Ripening: The ripening is done according to the same procedure as is used in example 2 except the pH remained the same i.e. pH=7 as during the nucleation.

Result: No tabular grains of aspect ratio larger than 5 resulted as is shown in table II for conventional commercial gelatin.

Example 7 (control)
Preparation of Silver Bromide Crystals with Conventional Hydrolysed Gelatins at a Different pH (Nitta Gelatins in Japan).

Nucleation: The nucleation is performed applying a different pH=7 condition while the other conditions remained the same as in example 2.

Ripening: the ripening is done according to the same procedure as is used in example 2 except the pH remained the same at pH=7 as during the nucleation.

40

Result: A very low % tabular grains around 5% resulted as is shown in table II.

Example 8 (this invention)

Preparation of Silver Bromide Crystals with Invented Native Recombinant Gelatin at a Different pH.

Nucleation: The nucleation is performed applying a different pH condition i.e. pH=7 while the other conditions remained the same as in example 4.

Ripening: The ripening is done according to the same procedure as is used in example 4 except the pH remained the same i.e. at pH=7 as during the nucleation.

Result: A very high % tabular grains ca 80% is surprisingly found at this condition which is clearly higher than the state-of-the-art gelatins as is shown in table II.

Example 9

Relation Between Binding Strength and Tabular Grain Morphology.

45 mg gelatin is accurately weighed and 15 g 0.1M phosphate buffer pH=7.00 containing 0.1M potassium nitrate, is added. The solution is placed in a waterbath at 45° C. for 15 minutes. The solution is cooled to room temperature (23° C.). 10 ml of this pH 7.0 phosphate buffer solution (containing gelatin) is mixed at 23° C. with 100 $\mu$l 0.5 mM silver nitrate. The potential of this solution entitled as "vAg" is measured using an Ag electrode (Orion model 97-81) against an Ag/AgCl reference double junction electrode (Orion model 90-02). The same buffer solution without gelatin is also mixed with the silver nitrate solution and the potential "vAg" measured by the same method. The difference between the two measured potentials is calculated and expressed as "delta vAg" being the binding affinity of gelatin for the Ag-ion. Table II below contains the tested peptizers, the % tabular grains and the gelatin binding affinities "delta VAg" for pH 5.5 and pH 7 in which the criteria for tabularity has been defined at aspect ratio >5:

| Type gelatin | Bind. strength "delta vAg" (mV) | % tabular at nucleation/ ripening p = 5.5 | % tabular at nucleation/ ripening pH = 7.0 |
|---|---|---|---|
| oxidized | 55.4 | 73 | —* |
| hydrolysed | 74.4 | 42 | 5 |
| regular | 78.5 | 1 | 0 |
| nat.rec COL3 | 69.5 | 87 | 79 |

*not measured

What is claimed is:

1. A tabular silver halide emulsion wherein the tabular grains account for more than 75% of the total grain projected area said emulsion comprising silver halide grains nucleated in the presence of a nucleation peptizer and thereafter grown in the presence of a growth peptizer, wherein at least one of the peptizers is substantially pure collagen like materials prepared by genetic engineering, said peptizer having an amino acid sequence comprising more than 4 different amino acids.

2. An emulsion according to claim 1, said peptizer having an amino acid sequence comprising more than 10 amino acids that are different.

3. A emulsion according to claim 1 wherein the amino acid sequence of the peptizer exhibits more than 40% homology with native collagen.

4. An emulsion according to claim 1 said peptizer having an amino acid sequence which is at least 80% identical to naturally occurring collagen.

5. An emulsion according to claim 1, wherein the peptizer has an amino acid sequence of naturally occurring collagen comprising 0–5 amino acid mutations.

6. An emulsion according to claim 1, wherein the peptizer is substantially pure collagen like material prepared by native collagen encoding nucleic acid.

7. An emulsion according to claim 1, wherein the peptizer has an amino acid sequence substantially the same as occurs in nature for collagen type I, II or III.

8. An emulsion according to claim 1, wherein the peptizer has an amino acid sequence equivalent to the amino acid sequence occurring in nature for collagen type I, II or III.

9. An emulsion according to claim 1, wherein the peptizer has an amino acid sequence the same as occurs in nature for collagen type I, II or III.

10. An emulsion according to claim 1, wherein the collagen is collagen type I which comprises or has the amino acid sequence of FIGS. 8, 10 or 12 or Genbank accession number U08020.

11. An emulsion according to claim 1, wherein the collagen is collagen type III which comprises or has the amino acid sequence of FIG. 3 of EMBL accession number X70-369.

12. An emulsion according to claim 1, wherein the peptizer is a fragment of defined length and composition derived from a native collagen encoding sequence, said fragment comprising the GXY motif characteristic of collagen, and the length of said fragment being such that the fragment weight on an amino acid basis is at least 2.5 kDa.

13. An emulsion according to claim 1, wherein the peptizer is free of hydroxyproline.

14. An emulsion according to claim 1, wherein the peptizer is not deaminated.

15. An emulsion according to claim 1, wherein the peptizer has an isoelectric point of 7–10.

16. An emulsion according to claim 1, wherein the peptizer has a weight on amino acid basis of 2.5–100 kDa.

17. An emulsion according to claim 1, said peptizer being free of procollagen and telopeptides.

18. An emulsion according to claim 1, said peptizer being free of helix structure.

19. An emulsion according to claim 1, said peptizer being free of cysteine.

20. An emulsion according to claim 1, said peptizer comprising (oxidated) reducing amino acids to a degree that reducing amino acids methionine and histidine are present at a level equivalent to a reducing strength of between 0.1–200 micromoles of methionine per gram of said peptizer.

21. An emulsion according to claim 1, said peptizer comprising (oxidated) reducing amino acids to a degree that reducing amino acids are present at a level equivalent to a reducing strength of between 0.1–80 micromoles of methionine per gram of said peptizer.

22. An emulsion according to claim 1, said peptizer comprising (oxidated) reducing amino acids to a degree that reducing amino acids are present at a level equivalent to a reducing strength of between 30–80 micromoles of methionine per gram of said peptizer.

23. An emulsion according to claim 1, said peptizer having a binding strength for silver higher than 50 mV.

24. An emulsion according to claim 1, said peptizer having a binding strength for silver below 100 mV.

25. An emulsion according to claim 1, said peptizer having a binding strength for silver between 50–100 mV.

26. An emulsion according to claim 1, wherein the silver halide grains exhibit an average aspect ratio higher than 5.

27. An emulsion according to claim 1, wherein the peptizer is stable vis a vis silver halide tabular grain formation at a pH between 4–8.

28. An emulsion according to claim 1 comprising tabular grains at a level more than 90%.

29. An emulsion according to claim 1 wherein the peptizer is of a homo disperse nature.

30. An emulsion according to claim 1 wherein the peptizer is present in substantially pure form.

31. An emulsion according to claim 1, said emulsion being suitable for photographic application and comprising further compounds acceptable for such application.

32. A process of preparing tabular silver halide emulsion wherein the tabular grains account for more than 75% of the total grain projected area said process comprising nucleation of silver halide grains in the presence of nucleation peptizer and thereafter growing said silver halide grains in the presence of growth peptizer, wherein both peptizers are present in a defined amount and at least one peptizer is collagen like material prepared by genetic engineering, said peptizers having an amino acid sequence comprising more than 4 different amino acids.

33. A process for preparing an emulsion according to claim 32 comprising addition of the peptizer in the nucleation step and/or during the grain growing step, said peptizer being substantially pure collagen like material prepared by genetic engineering, said peptizer having an amino acid sequence comprising more than 4 different amino acids.

34. A process for preparing an emulsion according to claim 32 comprising addition of the peptizer both in the nucleation step and during the grain growing step.

35. A process for preparing an emulsion according to claim 32 comprising addition of the same peptizer in the nucleation step and during the grain growing step.

36. A process of photographic element production comprising application of an emulsion according to claim 1 for obtaining a silver halide emulsion to be applied in a manner known per se for photographic element production with at least one silver halide emulsion layer, wherein the silver halide crystals of said layer have an aspect ratio of 5 or more.

37. A process according to claim 36, said photographic element being a material sensitive to light, laser or x-ray radiation.

38. Photographic element obtained according to the process according to claim 36.

39. An emulsion according to claim 3 wherein the amino acid sequence of the peptizer has greater than 50% homology with native collagen.

40. An emulsion according to claim 4 wherein said amino acid sequence is at least 90% identical to naturally occurring collagen.

41. An emulsion according to claim 5 wherein said peptizer has an amino acid sequence of naturally occurring collagen comprising 0–3 amino acid mutations.

42. An emulsion according to claim 1 wherein said peptizer comprises collagen.

43. An emulsion according to claim 42 wherein said collagen is one of collagen type I, II or III.

44. An emulsion according to claim 1, said peptizer having an amino acid sequence substantially the same as occurs in nature for collagen type I, the peptizer being free of at least one of a sequence XXR or a sequence MGPR (SEQ ID NO: 14).

45. An emulsion according to claim 20 wherein said reducing strength is between 0.1–120 micromoles of methionine per gram of peptizer.

46. An emulsion according to claim 28 wherein said tabular grains are present at a level of more than 95%.

47. An emulsion according to claim 31, further comprising a second amount of growth peptizer.

48. A process of claim 33 wherein said peptizer has an amino acid sequence of more than 10 amino acids.

49. A process of claim 33 wherein the amino acid sequence of the peptizer exhibits more than 40% homology with native collagen.

50. A process of claim 33 wherein said peptizer has an amino acid sequence which is at least 80% identical to naturally occurring collagen.

51. A process of claim 33 wherein said peptizer has an amino acid sequence which is at least 90% identical to naturally occurring collagen.

52. A process of claim 33 wherein said peptizer has an amino acid sequence of naturally occurring collagen comprising 0–5 amino acid mutations.

53. A process of claim 33 wherein said peptizer has an amino acid sequence of naturally occurring collagen comprising 0–3 amino acid mutations.

54. A process according to claim 33 wherein said peptizer is substantially pure collagen like material prepared by native collagen encoding nucleic acid.

55. A process according to claim 33 wherein said peptizer has an amino acid sequence substantially the same as native collagen type I, II or III.

56. A process according to claim 33 wherein said peptizer has the amino acid sequence of naturally occurring collagen type I, II or III.

57. A process according to claim 33 wherein said collagen is collagen type I which comprises or has the amino acid sequence of FIG. 8, 10 or 12 or Genbank accession number U08020.

58. A process according to claim 33 wherein the collagen is collagen type III which comprises or has the amino acid sequence of FIG. 3 or EMBL accession number X70-369.

59. A process according to claim 33 wherein said peptizer has an amino acid sequence substantially the same as naturally occurring collagen type I, the peptizer being free of a sequence XXR.

60. A process according to claim 59 wherein said peptizer is free of a sequence MGPR (SEQ ID NO: 14).

61. A process according to claim 33 wherein said peptizer is a fragment derived from native collagen, said fragment comprising the GXY motif of collagen and the length of said fragment is such that the fragment weight on an amino acid basis is at least 2.5 kDa.

62. A process according to claim 33 wherein said peptizer is free of hydroxyproline.

63. A process according to claim 33 wherein said peptizer is not deaminated.

64. A process according to claim 33 wherein said peptizer has an isoelectric point of 7–10.

65. A process according to claim 33 wherein said peptizer has a molecular weight on an amino acid basis of 2.5–100 kDa.

66. A process according to claim 33 wherein said peptizer is free of procollagen and telopeptides.

67. A process according to claim 33 wherein said peptizer is free of a helix structure.

68. A process according to claim 33 wherein said peptizer is free of cysteine.

69. A process according to claim 33 wherein said peptizer comprises (oxidated) reducing amino acids to a degree that reducing amino acids methionine and histidine are present at a level equivalent to a reducing strength of between 0.1–200 micromoles of methionine per gram of said peptizer.

70. A process according to claim 33 wherein said peptizer comprises (oxidated) reducing amino acids in an amount equivalent to a reducing strength of between 0.1–80 micromoles of methionine per gram of said peptizer.

71. A process according to claim 33 wherein said peptizer comprises (oxidated) reducing amino acids in an amount equivalent to a reducing strength of between 30–80 micromoles of methionine per gram of said peptizer.

72. A process according to claim 33 wherein said peptizer has a binding strength for silver of greater than 50 mV.

73. A process according to claim 33 wherein said peptizer has a binding strength for silver of less than 100 mV.

74. A process according to claim 33 wherein said peptizer has a binding strength for silver of between 50–100 mV.

75. A process according to claim 33 wherein said silver halide grains exhibit an average aspect ratio of greater than 5.

76. A process according to claim 33 wherein said peptizer is stable as compared with silver halide tabular grain formation at a pH between 4–8.

77. A process according to claim 33 wherein said tabular grains are present in an amount of more than 90%.

78. A process according to claim 33 wherein said tabular grains are present in an amount of more than 95%.

79. A process according to claim 33 wherein said peptizer is a homo dispersion.

80. A process of claim 33 wherein said peptizer is present in substantially pure form.

81. A process of claim 33 wherein said substantially pure collagen is prepared by genetic engineering and said peptizer has an amino acid sequence which is more than 40% homologous with naturally occurring collagen and comprises more than 4 types of amino acids.

82. A process of claim 37 wherein said element is selected from the group consisting of black and white reversal film, black and white negative film, colour negative film, colour reversal film, film in which the sensitive photographic components are digitally scanned, black and white reversal paper, black and white paper, colour paper, reversal colour paper, paper in which the sensitive photographic components are sensitized by laser radiation out of a digital database.

* * * * *

SEQUENCE LISTING

<160> NUMBER OF SEQ ID NOS: 50

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 1

Gly Leu Pro Gly Pro Lys Gly Asp Arg Gly Asp Ala Gly Pro Lys Gly
 1               5                  10                  15

Ala Asp Gly Ser Pro
            20

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence:
      Recombinantly produced synthetic CLP polypeptide

<400> SEQUENCE: 2

Gly Ala Pro Gly Pro Pro Gly Pro Pro Gly Pro Pro Gly Ala Pro Gly
 1               5                  10                  15

Pro Pro Gly Pro Pro Gly Pro Pro Gly Pro Val Gly Ser Pro
            20                  25                  30

<210> SEQ ID NO 3
<211> LENGTH: 504
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 3

Gly Ala His Gly Pro Ala Gly Pro Lys Gly Ala His Gly Pro Ala Gly
 1               5                  10                  15

Pro Lys Gly Ala Pro Gly Pro Ala Gly Pro Pro Gly Ala Pro Gly Pro
            20                  25                  30

Ala Gly Pro Pro Gly Ala Pro Gly Pro Ala Gly Pro Pro Gly Ala Pro
         35                  40                  45

Gly Pro Ala Gly Pro Pro Gly Ala Pro Gly Pro Ala Gly Pro Pro Gly
     50                  55                  60

Ala Pro Gly Pro Ala Gly Pro Pro Gly Ala Pro Gly Pro Ala Gly Pro
 65                  70                  75                  80

Pro Gly Ala Pro Gly Pro Ala Gly Pro Pro Gly Ala Pro Gly Pro Ala
                 85                  90                  95

Gly Pro Pro Gly Ala Pro Gly Pro Ala Gly Pro Pro Gly Ala Pro Gly
             100                 105                 110

Pro Ala Gly Pro Pro Gly Ala Pro Gly Pro Ala Gly Pro Pro Gly Ala
         115                 120                 125

Pro Gly Pro Ala Gly Pro Pro Gly Ala Pro Gly Pro Ala Gly Pro Pro
     130                 135                 140

Gly Ala Pro Gly Pro Ala Gly Pro Pro Gly Ala Pro Gly Pro Ala Gly
145                 150                 155                 160

-continued

```
Pro Pro Gly Ala Pro Gly Pro Ala Gly Pro Gly Ala Pro Gly Pro
            165                 170                 175
Ala Gly Pro Pro Gly Ala Pro Gly Pro Ala Gly Pro Pro Gly Ala Pro
        180                 185                 190
Gly Pro Ala Gly Pro Pro Gly Ala Pro Gly Pro Ala Gly Pro Pro Gly
        195                 200                 205
Ala Pro Gly Pro Ala Gly Pro Pro Gly Ala Pro Gly Pro Ala Gly Pro
    210                 215                 220
Pro Gly Ala Pro Gly Pro Ala Gly Pro Pro Gly Ala His Gly Pro Ala
225                 230                 235                 240
Gly Pro Lys Gly Ala His Gly Pro Ala Gly Pro Lys Gly Ala His Gly
            245                 250                 255
Pro Ala Gly Pro Lys Gly Ala His Gly Pro Ala Gly Pro Lys Gly Ala
        260                 265                 270
Pro Gly Pro Ala Gly Pro Pro Gly Ala Pro Gly Pro Ala Gly Pro Pro
        275                 280                 285
Gly Ala Pro Gly Pro Ala Gly Pro Pro Gly Ala Pro Gly Pro Ala Gly
    290                 295                 300
Pro Pro Gly Ala Pro Gly Pro Ala Gly Pro Pro Gly Ala Pro Gly Pro
305                 310                 315                 320
Ala Gly Pro Pro Gly Ala Pro Gly Pro Ala Gly Pro Pro Gly Ala Pro
            325                 330                 335
Gly Pro Ala Gly Pro Pro Gly Ala Pro Gly Pro Ala Gly Pro Pro Gly
        340                 345                 350
Ala Pro Gly Pro Ala Gly Pro Pro Gly Ala Pro Gly Pro Ala Gly Pro
        355                 360                 365
Pro Gly Ala Pro Gly Pro Ala Gly Pro Pro Gly Ala Pro Gly Pro Ala
    370                 375                 380
Gly Pro Pro Gly Ala Pro Gly Pro Ala Gly Pro Pro Gly Ala Pro Gly
385                 390                 395                 400
Pro Ala Gly Pro Pro Gly Ala Pro Gly Pro Ala Gly Pro Pro Gly Ala
            405                 410                 415
Pro Gly Pro Ala Gly Pro Pro Gly Ala Pro Gly Pro Ala Gly Pro Pro
        420                 425                 430
Gly Ala Pro Gly Pro Ala Gly Pro Pro Gly Ala Pro Gly Pro Ala Gly
        435                 440                 445
Pro Pro Gly Ala Pro Gly Pro Ala Gly Pro Pro Gly Ala Pro Gly Pro
    450                 455                 460
Ala Gly Pro Pro Gly Ala Pro Gly Pro Ala Gly Pro Pro Gly Ala Pro
465                 470                 475                 480
Gly Pro Ala Gly Pro Pro Gly Ala His Gly Pro Ala Gly Pro Lys Gly
            485                 490                 495
Ala His Gly Pro Ala Gly Pro Lys
            500

<210> SEQ ID NO 4
<211> LENGTH: 720
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 4

Gly Ala His Gly Pro Ala Gly Pro Lys Gly Ala His Gly Pro Ala Gly
1               5                   10                  15
```

```
Pro Lys Gly Ala Pro Gly Pro Ala Gly Pro Ala Gly Pro
             20                  25                  30

Ala Gly Pro Pro Gly Ala Pro Gly Pro Ala Gly Pro Pro Gly Ala Pro
             35                  40                  45

Gly Pro Ala Gly Pro Pro Gly Ala Pro Gly Pro Ala Gly Pro Pro Gly
             50                  55                  60

Ala Pro Gly Pro Ala Gly Pro Pro Gly Ala Pro Gly Pro Ala Gly Pro
 65                  70                  75                  80

Pro Gly Ala Pro Gly Pro Ala Gly Pro Pro Gly Ala Pro Gly Pro Ala
                 85                  90                  95

Gly Pro Pro Gly Ala Pro Gly Pro Ala Gly Pro Pro Gly Ala Pro Gly
                100                 105                 110

Pro Ala Gly Pro Pro Gly Ala Pro Gly Pro Ala Gly Pro Pro Gly Ala
            115                 120                 125

His Gly Pro Ala Gly Pro Lys Gly Ala His Gly Pro Ala Gly Pro Lys
            130                 135                 140

Gly Ala His Gly Pro Ala Gly Pro Lys Gly Ala His Gly Pro Ala Gly
145                 150                 155                 160

Pro Lys Gly Ala Pro Gly Pro Ala Gly Pro Pro Gly Ala Pro Gly Pro
                165                 170                 175

Ala Gly Pro Pro Gly Ala Pro Gly Pro Ala Gly Pro Pro Gly Ala Pro
            180                 185                 190

Gly Pro Ala Gly Pro Pro Gly Ala Pro Gly Pro Ala Gly Pro Pro Gly
            195                 200                 205

Ala Pro Gly Pro Ala Gly Pro Pro Gly Ala Pro Gly Pro Ala Gly Pro
            210                 215                 220

Pro Gly Ala Pro Gly Pro Ala Gly Pro Pro Gly Ala Pro Gly Pro Ala
225                 230                 235                 240

Gly Pro Pro Gly Ala Pro Gly Pro Ala Gly Pro Pro Gly Ala Pro Gly
                245                 250                 255

Pro Ala Gly Pro Pro Gly Ala Pro Gly Pro Ala Gly Pro Pro Gly Ala
            260                 265                 270

His Gly Pro Ala Gly Pro Lys Gly Ala His Gly Pro Ala Gly Pro Lys
            275                 280                 285

Gly Ala His Gly Pro Ala Gly Pro Lys Gly Ala His Gly Pro Ala Gly
            290                 295                 300

Pro Lys Gly Ala Pro Gly Pro Ala Gly Pro Pro Gly Ala Pro Gly Pro
305                 310                 315                 320

Ala Gly Pro Pro Gly Ala Pro Gly Pro Ala Gly Pro Pro Gly Ala Pro
                325                 330                 335

Gly Pro Ala Gly Pro Pro Gly Ala Pro Gly Pro Ala Gly Pro Pro Gly
            340                 345                 350

Ala Pro Gly Pro Ala Gly Pro Pro Gly Ala Pro Gly Pro Ala Gly Pro
            355                 360                 365

Pro Gly Ala Pro Gly Pro Ala Gly Pro Pro Gly Ala Pro Gly Pro Ala
            370                 375                 380

Gly Pro Pro Gly Ala Pro Gly Pro Ala Gly Pro Pro Gly Ala Pro Gly
385                 390                 395                 400

Pro Ala Gly Pro Pro Gly Ala Pro Gly Pro Ala Gly Pro Pro Gly Ala
                405                 410                 415

His Gly Pro Ala Gly Pro Lys Gly Ala His Gly Pro Ala Gly Pro Lys
            420                 425                 430
```

-continued

Gly Ala His Gly Pro Ala Gly Pro Lys Gly Ala His Gly Pro Ala Gly
                435                 440                 445

Pro Lys Gly Ala Pro Gly Pro Ala Gly Pro Pro Gly Ala Pro Gly Pro
        450                 455                 460

Ala Gly Pro Pro Gly Ala Pro Gly Pro Ala Gly Pro Pro Gly Ala Pro
465                 470                 475                 480

Gly Pro Ala Gly Pro Pro Gly Ala Pro Gly Pro Ala Gly Pro Pro Gly
                485                 490                 495

Ala Pro Gly Pro Ala Gly Pro Pro Gly Ala Pro Gly Pro Ala Gly Pro
        500                 505                 510

Pro Gly Ala Pro Gly Pro Ala Gly Pro Pro Gly Ala Pro Gly Pro Ala
        515                 520                 525

Gly Pro Pro Gly Ala Pro Gly Pro Ala Gly Pro Pro Gly Ala Pro Gly
        530                 535                 540

Pro Ala Gly Pro Pro Gly Ala Pro Gly Pro Ala Gly Pro Pro Gly Ala
545                 550                 555                 560

His Gly Pro Ala Gly Pro Lys Gly Ala His Gly Pro Ala Gly Pro Lys
                565                 570                 575

Gly Ala His Gly Pro Ala Gly Pro Lys Gly Ala His Gly Pro Ala Gly
                580                 585                 590

Pro Lys Gly Ala Pro Gly Pro Ala Gly Pro Pro Gly Ala Pro Gly Pro
        595                 600                 605

Ala Gly Pro Pro Gly Ala Pro Gly Pro Ala Gly Pro Pro Gly Ala Pro
        610                 615                 620

Gly Pro Ala Gly Pro Pro Gly Ala Pro Gly Pro Ala Gly Pro Pro Gly
625                 630                 635                 640

Ala Pro Gly Pro Ala Gly Pro Pro Gly Ala Pro Gly Pro Ala Gly Pro
                645                 650                 655

Pro Gly Ala Pro Gly Pro Ala Gly Pro Pro Gly Ala Pro Gly Pro Ala
        660                 665                 670

Gly Pro Pro Gly Ala Pro Gly Pro Ala Gly Pro Pro Gly Ala Pro Gly
        675                 680                 685

Pro Ala Gly Pro Pro Gly Ala Pro Gly Pro Ala Gly Pro Pro Gly Ala
        690                 695                 700

His Gly Pro Ala Gly Pro Lys Gly Ala His Gly Pro Ala Gly Pro Lys
705                 710                 715                 720

<210> SEQ ID NO 5
<211> LENGTH: 960
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 5

Gly Ala His Gly Pro Ala Gly Pro Lys Gly Ala His Gly Pro Ala Gly
  1               5                  10                  15

Pro Lys Gly Ala Pro Gly Pro Ala Gly Pro Pro Gly Ser Arg Asp Pro
         20                  25                  30

Gly Pro Pro Gly Ala Pro Gly Pro Ala Gly Pro Pro Gly Ser Arg Asp
         35                  40                  45

Pro Gly Pro Pro Gly Ala Pro Gly Pro Ala Gly Pro Pro Gly Ser Arg
         50                  55                  60

Asp Pro Gly Pro Pro Gly Ala Pro Gly Pro Ala Gly Pro Pro Gly Ser
65                  70                  75                  80

-continued

```
Arg Asp Pro Gly Pro Pro Gly Ala Pro Gly Pro Ala Gly Pro Pro Gly
             85                  90                  95

Ser Arg Asp Pro Gly Pro Pro Gly Ala Pro Gly Pro Ala Gly Pro Pro
            100                 105                 110

Gly Ser Arg Asp Pro Gly Pro Pro Gly Ala Pro Gly Pro Ala Gly Pro
            115                 120                 125

Pro Gly Ser Arg Asp Pro Gly Pro Pro Gly Ala Pro Gly Pro Ala Gly
        130                 135                 140

Pro Pro Gly Ser Arg Asp Pro Gly Pro Pro Gly Ala Pro Gly Pro Ala
145                 150                 155                 160

Gly Pro Pro Gly Ser Arg Asp Pro Gly Pro Pro Gly Ala Pro Gly Pro
                165                 170                 175

Ala Gly Pro Pro Gly Ser Arg Asp Pro Gly Pro Pro Gly Ala Pro Gly
            180                 185                 190

Pro Ala Gly Pro Pro Gly Ser Arg Asp Pro Gly Pro Pro Gly Ala Pro
        195                 200                 205

Gly Pro Ala Gly Pro Pro Gly Ser Arg Asp Pro Gly Pro Pro Gly Ala
    210                 215                 220

His Gly Pro Ala Gly Pro Lys Gly Ala His Gly Pro Ala Gly Pro Lys
225                 230                 235                 240

Gly Ala His Gly Pro Ala Gly Pro Lys Gly Ala His Gly Pro Ala Gly
                245                 250                 255

Pro Lys Gly Ala Pro Gly Pro Ala Gly Pro Pro Gly Ser Arg Asp Pro
            260                 265                 270

Gly Pro Pro Gly Ala Pro Gly Pro Ala Gly Pro Pro Gly Ser Arg Asp
        275                 280                 285

Pro Gly Pro Pro Gly Ala Pro Gly Pro Ala Gly Pro Pro Gly Ser Arg
    290                 295                 300

Asp Pro Gly Pro Pro Gly Ala Pro Gly Pro Ala Gly Pro Pro Gly Ser
305                 310                 315                 320

Arg Asp Pro Gly Pro Pro Gly Ala Pro Gly Pro Ala Gly Pro Pro Gly
                325                 330                 335

Ser Arg Asp Pro Gly Pro Pro Gly Ala Pro Gly Pro Ala Gly Pro Pro
            340                 345                 350

Gly Ser Arg Asp Pro Gly Pro Pro Gly Ala Pro Gly Pro Ala Gly Pro
        355                 360                 365

Pro Gly Ser Arg Asp Pro Gly Pro Pro Gly Ala Pro Gly Pro Ala Gly
    370                 375                 380

Pro Pro Gly Ser Arg Asp Pro Gly Pro Pro Gly Ala Pro Gly Pro Ala
385                 390                 395                 400

Gly Pro Pro Gly Ser Arg Asp Pro Gly Pro Pro Gly Ala Pro Gly Pro
                405                 410                 415

Ala Gly Pro Pro Gly Ser Arg Asp Pro Gly Pro Pro Gly Ala Pro Gly
            420                 425                 430

Pro Ala Gly Pro Pro Gly Ser Arg Asp Pro Gly Pro Pro Gly Ala Pro
        435                 440                 445

Gly Pro Ala Gly Pro Pro Gly Ser Arg Asp Pro Gly Pro Pro Gly Ala
    450                 455                 460

His Gly Pro Ala Gly Pro Lys Gly Ala His Gly Pro Ala Gly Pro Lys
465                 470                 475                 480

Gly Ala His Gly Pro Ala Gly Pro Lys Gly Ala His Gly Pro Ala Gly
                485                 490                 495
```

-continued

```
Pro Lys Gly Ala Pro Gly Pro Ala Gly Pro Pro Gly Ser Arg Asp Pro
            500                 505                 510
Gly Pro Pro Gly Ala Pro Gly Pro Ala Gly Pro Pro Gly Ser Arg Asp
        515                 520                 525
Pro Gly Pro Pro Gly Ala Pro Gly Pro Ala Gly Pro Pro Gly Ser Arg
    530                 535                 540
Asp Pro Gly Pro Pro Gly Ala Pro Gly Pro Ala Gly Pro Pro Gly Ser
545                 550                 555                 560
Arg Asp Pro Gly Pro Pro Gly Ala Pro Gly Pro Ala Gly Pro Pro Gly
                565                 570                 575
Ser Arg Asp Pro Gly Pro Pro Gly Ala Pro Gly Pro Ala Gly Pro Pro
            580                 585                 590
Gly Ser Arg Asp Pro Gly Pro Pro Gly Ala Pro Gly Pro Ala Gly Pro
        595                 600                 605
Pro Gly Ser Arg Asp Pro Gly Pro Pro Gly Ala Pro Gly Pro Ala Gly
    610                 615                 620
Pro Pro Gly Ser Arg Asp Pro Gly Pro Pro Gly Ala Pro Gly Pro Ala
625                 630                 635                 640
Gly Pro Pro Gly Ser Arg Asp Pro Gly Pro Pro Gly Ala Pro Gly Pro
                645                 650                 655
Ala Gly Pro Pro Gly Ser Arg Asp Pro Gly Pro Pro Gly Ala Pro Gly
            660                 665                 670
Pro Ala Gly Pro Pro Gly Ser Arg Asp Pro Gly Pro Pro Gly Ala Pro
        675                 680                 685
Gly Pro Ala Gly Pro Pro Gly Ser Arg Asp Pro Gly Pro Pro Gly Ala
    690                 695                 700
His Gly Pro Ala Gly Pro Lys Gly Ala His Gly Pro Ala Gly Pro Lys
705                 710                 715                 720
Gly Ala His Gly Pro Ala Gly Pro Lys Gly Ala His Gly Pro Ala Gly
                725                 730                 735
Pro Lys Gly Ala Pro Gly Pro Ala Gly Pro Pro Gly Ser Arg Asp Pro
            740                 745                 750
Gly Pro Pro Gly Ala Pro Gly Pro Ala Gly Pro Pro Gly Ser Arg Asp
        755                 760                 765
Pro Gly Pro Pro Gly Ala Pro Gly Pro Ala Gly Pro Pro Gly Ser Arg
    770                 775                 780
Asp Pro Gly Pro Pro Gly Ala Pro Gly Pro Ala Gly Pro Pro Gly Ser
785                 790                 795                 800
Arg Asp Pro Gly Pro Pro Gly Ala Pro Gly Pro Ala Gly Pro Pro Gly
                805                 810                 815
Ser Arg Asp Pro Gly Pro Pro Gly Ala Pro Gly Pro Ala Gly Pro Pro
            820                 825                 830
Gly Ser Arg Asp Pro Gly Pro Pro Gly Ala Pro Gly Pro Ala Gly Pro
        835                 840                 845
Pro Gly Ser Arg Asp Pro Gly Pro Pro Gly Ala Pro Gly Pro Ala Gly
    850                 855                 860
Pro Pro Gly Ser Arg Asp Pro Gly Pro Pro Gly Ala Pro Gly Pro Ala
865                 870                 875                 880
Gly Pro Pro Gly Ser Arg Asp Pro Gly Pro Pro Gly Ala Pro Gly Pro
                885                 890                 895
Ala Gly Pro Pro Gly Ser Arg Asp Pro Gly Pro Pro Gly Ala Pro Gly
            900                 905                 910
```

```
Pro Ala Gly Pro Pro Gly Ser Arg Asp Pro Gly Pro Pro Gly Ala Pro
            915                 920                 925

Gly Pro Ala Gly Pro Pro Gly Ser Arg Asp Pro Gly Pro Pro Gly Ala
            930                 935                 940

His Gly Pro Ala Gly Pro Lys Gly Ala His Gly Pro Ala Gly Pro Lys
945                 950                 955                 960

<210> SEQ ID NO 6
<211> LENGTH: 960
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 6

Gly Ala His Gly Pro Ala Gly Pro Lys Gly Ala His Gly Pro Ala Gly
  1               5                  10                  15

Pro Lys Gly Ala Gln Gly Pro Ala Gly Pro Gly Gly Ser Arg Asp Pro
             20                  25                  30

Gly Pro Pro Gly Ala Gln Gly Pro Ala Gly Pro Gly Gly Ser Arg Asp
             35                  40                  45

Pro Gly Pro Pro Gly Ala Gln Gly Pro Ala Gly Pro Gly Gly Ser Arg
         50                  55                  60

Asp Pro Gly Pro Pro Gly Ala Gln Gly Pro Ala Gly Pro Gly Gly Ser
 65                  70                  75                  80

Arg Asp Pro Gly Pro Pro Gly Ala Gln Gly Pro Ala Gly Pro Gly Gly
                 85                  90                  95

Ser Arg Asp Pro Gly Pro Pro Gly Ala Gln Gly Pro Ala Gly Pro Gly
            100                 105                 110

Gly Ser Arg Asp Pro Gly Pro Pro Gly Ala Gln Gly Pro Ala Gly Pro
            115                 120                 125

Gly Gly Ser Arg Asp Pro Gly Pro Pro Gly Ala Gln Gly Pro Ala Gly
            130                 135                 140

Pro Gly Gly Ser Arg Asp Pro Gly Pro Pro Gly Ala Gln Gly Pro Ala
145                 150                 155                 160

Gly Pro Gly Gly Ser Arg Asp Pro Gly Pro Pro Gly Ala Gln Gly Pro
                165                 170                 175

Ala Gly Pro Gly Gly Ser Arg Asp Pro Gly Pro Pro Gly Ala Gln Gly
            180                 185                 190

Pro Ala Gly Pro Gly Gly Ser Arg Asp Pro Gly Pro Pro Gly Ala Gln
            195                 200                 205

Gly Pro Ala Gly Pro Gly Gly Ser Arg Asp Pro Gly Pro Pro Gly Ala
            210                 215                 220

His Gly Pro Ala Gly Pro Lys Gly Ala His Gly Pro Ala Gly Pro Lys
225                 230                 235                 240

Gly Ala His Gly Pro Ala Gly Pro Lys Gly Ala His Gly Pro Ala Gly
                245                 250                 255

Pro Lys Gly Ala Gln Gly Pro Ala Gly Pro Gly Gly Ser Arg Asp Pro
            260                 265                 270

Gly Pro Pro Gly Ala Gln Gly Pro Ala Gly Pro Gly Gly Ser Arg Asp
            275                 280                 285

Pro Gly Pro Pro Gly Ala Gln Gly Pro Ala Gly Pro Gly Gly Ser Arg
        290                 295                 300

Asp Pro Gly Pro Pro Gly Ala Gln Gly Pro Ala Gly Pro Gly Gly Ser
305                 310                 315                 320
```

-continued

```
Arg Asp Pro Gly Pro Pro Gly Ala Gln Gly Pro Ala Gly Pro Gly Gly
            325                 330                 335

Ser Arg Asp Pro Gly Pro Pro Gly Ala Gln Gly Pro Ala Gly Pro Gly
            340                 345                 350

Gly Ser Arg Asp Pro Gly Pro Pro Gly Ala Gln Gly Pro Ala Gly Pro
            355                 360                 365

Gly Gly Ser Arg Asp Pro Gly Pro Pro Gly Ala Gln Gly Pro Ala Gly
    370                 375                 380

Pro Gly Gly Ser Arg Asp Pro Gly Pro Pro Gly Ala Gln Gly Pro Ala
385                 390                 395                 400

Gly Pro Gly Gly Ser Arg Asp Pro Gly Pro Pro Gly Ala Gln Gly Pro
            405                 410                 415

Ala Gly Pro Gly Gly Ser Arg Asp Pro Gly Pro Pro Gly Ala Gln Gly
            420                 425                 430

Pro Ala Gly Pro Gly Gly Ser Arg Asp Pro Gly Pro Pro Gly Ala Gln
            435                 440                 445

Gly Pro Ala Gly Pro Gly Gly Ser Arg Asp Pro Gly Pro Pro Gly Ala
            450                 455                 460

His Gly Pro Ala Gly Pro Lys Gly Ala His Gly Pro Ala Gly Pro Lys
465                 470                 475                 480

Gly Ala His Gly Pro Ala Gly Pro Lys Gly Ala His Gly Pro Ala Gly
            485                 490                 495

Pro Lys Gly Ala Gln Gly Pro Ala Gly Pro Gly Gly Ser Arg Asp Pro
            500                 505                 510

Gly Pro Pro Gly Ala Gln Gly Pro Ala Gly Pro Gly Gly Ser Arg Asp
            515                 520                 525

Pro Gly Pro Pro Gly Ala Gln Gly Pro Ala Gly Pro Gly Gly Ser Arg
            530                 535                 540

Asp Pro Gly Pro Pro Gly Ala Gln Gly Pro Ala Gly Pro Gly Gly Ser
545                 550                 555                 560

Arg Asp Pro Gly Pro Pro Gly Ala Gln Gly Pro Ala Gly Pro Gly Gly
            565                 570                 575

Ser Arg Asp Pro Gly Pro Pro Gly Ala Gln Gly Pro Ala Gly Pro Gly
            580                 585                 590

Gly Ser Arg Asp Pro Gly Pro Pro Gly Ala Gln Gly Pro Ala Gly Pro
            595                 600                 605

Gly Gly Ser Arg Asp Pro Gly Pro Pro Gly Ala Gln Gly Pro Ala Gly
            610                 615                 620

Pro Gly Gly Ser Arg Asp Pro Gly Pro Pro Gly Ala Gln Gly Pro Ala
625                 630                 635                 640

Gly Pro Gly Gly Ser Arg Asp Pro Gly Pro Pro Gly Ala Gln Gly Pro
            645                 650                 655

Ala Gly Pro Gly Gly Ser Arg Asp Pro Gly Pro Pro Gly Ala Gln Gly
            660                 665                 670

Pro Ala Gly Pro Gly Gly Ser Arg Asp Pro Gly Pro Pro Gly Ala Gln
            675                 680                 685

Gly Pro Ala Gly Pro Gly Gly Ser Arg Asp Pro Gly Pro Pro Gly Ala
            690                 695                 700

His Gly Pro Ala Gly Pro Lys Gly Ala His Gly Pro Ala Gly Pro Lys
705                 710                 715                 720

Gly Ala His Gly Pro Ala Gly Pro Lys Gly Ala His Gly Pro Ala Gly
            725                 730                 735
```

-continued

```
Pro Lys Gly Ala Gln Gly Pro Ala Gly Pro Gly Gly Ser Arg Asp Pro
        740                 745                 750

Gly Pro Pro Gly Ala Gln Gly Pro Ala Gly Pro Gly Gly Ser Arg Asp
    755                 760                 765

Pro Gly Pro Pro Gly Ala Gln Gly Pro Ala Gly Pro Gly Gly Ser Arg
770                 775                 780

Asp Pro Gly Pro Pro Gly Ala Gln Gly Pro Ala Gly Pro Gly Gly Ser
785                 790                 795                 800

Arg Asp Pro Gly Pro Pro Gly Ala Gln Gly Pro Ala Gly Pro Gly Gly
                805                 810                 815

Ser Arg Asp Pro Gly Pro Pro Gly Ala Gln Gly Pro Ala Gly Pro Gly
            820                 825                 830

Gly Ser Arg Asp Pro Gly Pro Pro Gly Ala Gln Gly Pro Ala Gly Pro
        835                 840                 845

Gly Gly Ser Arg Asp Pro Gly Pro Pro Gly Ala Gln Gly Pro Ala Gly
    850                 855                 860

Pro Gly Gly Ser Arg Asp Pro Gly Pro Pro Gly Ala Gln Gly Pro Ala
865                 870                 875                 880

Gly Pro Gly Gly Ser Arg Asp Pro Gly Pro Pro Gly Ala Gln Gly Pro
                885                 890                 895

Ala Gly Pro Gly Gly Ser Arg Asp Pro Gly Pro Pro Gly Ala Gln Gly
            900                 905                 910

Pro Ala Gly Pro Gly Gly Ser Arg Asp Pro Gly Pro Pro Gly Ala Gln
        915                 920                 925

Gly Pro Ala Gly Pro Gly Gly Ser Arg Asp Pro Gly Pro Pro Gly Ala
    930                 935                 940

His Gly Pro Ala Gly Pro Lys Gly Ala His Gly Pro Ala Gly Pro Lys
945                 950                 955                 960
```

<210> SEQ ID NO 7
<211> LENGTH: 552
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 7

```
Gly Ala His Gly Pro Ala Gly Pro Lys Gly Ala His Gly Pro Ala Gly
1               5                   10                  15

Pro Lys Gly Ala Gln Gly Pro Ala Gly Pro Gly Gly Ser Arg Asp Pro
            20                  25                  30

Gly Pro Pro Gly Ala Gln Gly Pro Ala Gly Pro Gly Gly Ser Arg Asp
        35                  40                  45

Pro Gly Pro Pro Gly Ala Gln Gly Pro Ala Gly Pro Gly Gly Ser Arg
    50                  55                  60

Asp Pro Gly Pro Pro Gly Ala Gln Gly Pro Ala Gly Pro Gly Gly Ser
65                  70                  75                  80

Arg Asp Pro Gly Pro Pro Gly Ala Gln Gly Pro Ala Gly Pro Gly Gly
                85                  90                  95

Ser Arg Asp Pro Gly Pro Pro Gly Ala Gln Gly Pro Ala Gly Pro Gly
            100                 105                 110

Gly Ser Arg Asp Pro Gly Pro Pro Gly Ala His Gly Pro Ala Gly Pro
        115                 120                 125

Lys Gly Ala His Gly Pro Ala Gly Pro Lys Gly Ala His Gly Pro Ala
    130                 135                 140
```

```
Gly Pro Lys Gly Ala His Gly Pro Ala Gly Pro Lys Gly Ala Gln Gly
145                 150                 155                 160

Pro Ala Gly Pro Gly Gly Ser Arg Asp Pro Gly Pro Pro Gly Ala Gln
                165                 170                 175

Gly Pro Ala Gly Pro Gly Gly Ser Arg Asp Pro Gly Pro Pro Gly Ala
            180                 185                 190

Gln Gly Pro Ala Gly Pro Gly Gly Ser Arg Asp Pro Gly Pro Pro Gly
        195                 200                 205

Ala Gln Gly Pro Ala Gly Pro Gly Gly Ser Arg Asp Pro Gly Pro Pro
210                 215                 220

Gly Ala Gln Gly Pro Ala Gly Pro Gly Gly Ser Arg Asp Pro Gly Pro
225                 230                 235                 240

Pro Gly Ala Gln Gly Pro Ala Gly Pro Gly Gly Ser Arg Asp Pro Gly
                245                 250                 255

Pro Pro Gly Ala His Gly Pro Ala Gly Pro Lys Gly Ala His Gly Pro
                260                 265                 270

Ala Gly Pro Lys Gly Ala His Gly Pro Ala Gly Pro Lys Gly Ala His
            275                 280                 285

Gly Pro Ala Gly Pro Lys Gly Ala Gln Gly Pro Ala Gly Pro Gly Gly
        290                 295                 300

Ser Arg Asp Pro Gly Pro Pro Gly Ala Gln Gly Pro Ala Gly Pro Gly
305                 310                 315                 320

Gly Ser Arg Asp Pro Gly Pro Pro Gly Ala Gln Gly Pro Ala Gly Pro
                325                 330                 335

Gly Gly Ser Arg Asp Pro Gly Pro Pro Gly Ala Gln Gly Pro Ala Gly
                340                 345                 350

Pro Gly Gly Ser Arg Asp Pro Gly Pro Pro Gly Ala Gln Gly Pro Ala
            355                 360                 365

Gly Pro Gly Gly Ser Arg Asp Pro Gly Pro Pro Gly Ala Gln Gly Pro
        370                 375                 380

Ala Gly Pro Gly Gly Ser Arg Asp Pro Gly Pro Pro Gly Ala His Gly
385                 390                 395                 400

Pro Ala Gly Pro Lys Gly Ala His Gly Pro Ala Gly Pro Lys Gly Ala
                405                 410                 415

His Gly Pro Ala Gly Pro Lys Gly Ala His Gly Pro Ala Gly Pro Lys
                420                 425                 430

Gly Ala Gln Gly Pro Ala Gly Pro Gly Gly Ser Arg Asp Pro Gly Pro
            435                 440                 445

Pro Gly Ala Gln Gly Pro Ala Gly Pro Gly Gly Ser Arg Asp Pro Gly
        450                 455                 460

Pro Pro Gly Ala Gln Gly Pro Ala Gly Pro Gly Gly Ser Arg Asp Pro
465                 470                 475                 480

Gly Pro Pro Gly Ala Gln Gly Pro Ala Gly Pro Gly Gly Ser Arg Asp
                485                 490                 495

Pro Gly Pro Pro Gly Ala Gln Gly Pro Ala Gly Pro Gly Gly Ser Arg
                500                 505                 510

Asp Pro Gly Pro Pro Gly Ala Gln Gly Pro Ala Gly Pro Gly Gly Ser
            515                 520                 525

Arg Asp Pro Gly Pro Pro Gly Ala His Gly Pro Ala Gly Pro Lys Gly
        530                 535                 540

Ala His Gly Pro Ala Gly Pro Lys
545                 550
```

<210> SEQ ID NO 8
<211> LENGTH: 1008
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 8

```
Gly Ala His Gly Pro Ala Gly Pro Lys Gly Ala His Gly Pro Ala Gly
  1               5                  10                  15

Pro Lys Gly Ala Gln Gly Pro Ala Gly Pro Gly Gly Ala Gln Gly Pro
             20                  25                  30

Ala Gly Pro Gly Gly Ala Gln Gly Pro Ala Gly Pro Gly Gly Ala Gln
         35                  40                  45

Gly Pro Ala Gly Pro Gly Gly Ala Gln Gly Pro Ala Gly Pro Gly Gly
     50                  55                  60

Ala Gln Gly Pro Ala Gly Pro Gly Gly Ala Gln Gly Pro Ala Gly Pro
 65                  70                  75                  80

Gly Gly Ala Gln Gly Pro Ala Gly Pro Gly Gly Ala Gln Gly Pro Ala
                 85                  90                  95

Gly Pro Gly Gly Ala Gln Gly Pro Ala Gly Pro Gly Gly Ala Gln Gly
            100                 105                 110

Pro Ala Gly Pro Gly Gly Ala Gln Gly Pro Ala Gly Pro Gly Gly Ala
        115                 120                 125

Gln Gly Pro Ala Gly Pro Gly Gly Ala Gln Gly Pro Ala Gly Pro Gly
    130                 135                 140

Gly Ala Gln Gly Pro Ala Gly Pro Gly Gly Ala Gln Gly Pro Ala Gly
145                 150                 155                 160

Pro Gly Gly Ala Gln Gly Pro Ala Gly Pro Gly Gly Ala Gln Gly Pro
                165                 170                 175

Ala Gly Pro Gly Gly Ala Gln Gly Pro Ala Gly Pro Gly Gly Ala Gln
            180                 185                 190

Gly Pro Ala Gly Pro Gly Gly Ala Gln Gly Pro Ala Gly Pro Gly Gly
        195                 200                 205

Ala Gln Gly Pro Ala Gly Pro Gly Gly Ala Gln Gly Pro Ala Gly Pro
    210                 215                 220

Gly Gly Ala Gln Gly Pro Ala Gly Pro Gly Gly Ala His Gly Pro Ala
225                 230                 235                 240

Gly Pro Lys Gly Ala His Gly Pro Ala Gly Pro Lys Gly Ala His Gly
                245                 250                 255

Pro Ala Gly Pro Lys Gly Ala His Gly Pro Ala Gly Pro Lys Gly Ala
            260                 265                 270

Gln Gly Pro Ala Gly Pro Gly Gly Ala Gln Gly Pro Ala Gly Pro Gly
        275                 280                 285

Gly Ala Gln Gly Pro Ala Gly Pro Gly Gly Ala Gln Gly Pro Ala Gly
    290                 295                 300

Pro Gly Gly Ala Gln Gly Pro Ala Gly Pro Gly Gly Ala Gln Gly Pro
305                 310                 315                 320

Ala Gly Pro Gly Gly Ala Gln Gly Pro Ala Gly Pro Gly Gly Ala Gln
                325                 330                 335

Gly Pro Ala Gly Pro Gly Gly Ala Gln Gly Pro Ala Gly Pro Gly Gly
            340                 345                 350

Ala Gln Gly Pro Ala Gly Pro Gly Gly Ala Gln Gly Pro Ala Gly Pro
        355                 360                 365
```

-continued

```
Gly Gly Ala Gln Gly Pro Ala Gly Pro Gly Gly Ala Gln Gly Pro Ala
    370                 375                 380
Gly Pro Gly Gly Ala Gln Gly Pro Ala Gly Pro Gly Gly Ala Gln Gly
385                 390                 395                 400
Pro Ala Gly Pro Gly Gly Ala Gln Gly Pro Ala Gly Pro Gly Gly Ala
                405                 410                 415
Gln Gly Pro Ala Gly Pro Gly Gly Ala Gln Gly Pro Ala Gly Pro Gly
            420                 425                 430
Gly Ala Gln Gly Pro Ala Gly Pro Gly Gly Ala Gln Gly Pro Ala Gly
        435                 440                 445
Pro Gly Gly Ala Gln Gly Pro Ala Gly Pro Gly Gly Ala Gln Gly Pro
    450                 455                 460
Ala Gly Pro Gly Gly Ala Gln Gly Pro Ala Gly Pro Gly Gly Ala Gln
465                 470                 475                 480
Gly Pro Ala Gly Pro Gly Ala His Gly Pro Ala Gly Pro Lys Gly
                485                 490                 495
Ala His Gly Pro Ala Gly Pro Lys Gly Ala His Gly Pro Ala Gly Pro
            500                 505                 510
Lys Gly Ala His Gly Pro Ala Gly Pro Lys Gly Ala Gln Gly Pro Ala
        515                 520                 525
Gly Pro Gly Gly Ala Gln Gly Pro Ala Gly Pro Gly Gly Ala Gln Gly
    530                 535                 540
Pro Ala Gly Pro Gly Gly Ala Gln Gly Pro Ala Gly Pro Gly Gly Ala
545                 550                 555                 560
Gln Gly Pro Ala Gly Pro Gly Gly Ala Gln Gly Pro Ala Gly Pro Gly
                565                 570                 575
Gly Ala Gln Gly Pro Ala Gly Pro Gly Gly Ala Gln Gly Pro Ala Gly
            580                 585                 590
Pro Gly Gly Ala Gln Gly Pro Ala Gly Pro Gly Gly Ala Gln Gly Pro
        595                 600                 605
Ala Gly Pro Gly Gly Ala Gln Gly Pro Ala Gly Pro Gly Gly Ala Gln
    610                 615                 620
Gly Pro Ala Gly Pro Gly Gly Ala Gln Gly Pro Ala Gly Pro Gly Gly
625                 630                 635                 640
Ala Gln Gly Pro Ala Gly Pro Gly Gly Ala Gln Gly Pro Ala Gly Pro
                645                 650                 655
Gly Gly Ala Gln Gly Pro Ala Gly Pro Gly Gly Ala Gln Gly Pro Ala
            660                 665                 670
Gly Pro Gly Gly Ala Gln Gly Pro Ala Gly Pro Gly Gly Ala Gln Gly
        675                 680                 685
Pro Ala Gly Pro Gly Gly Ala Gln Gly Pro Ala Gly Pro Gly Gly Ala
    690                 695                 700
Gln Gly Pro Ala Gly Pro Gly Gly Ala Gln Gly Pro Ala Gly Pro Gly
705                 710                 715                 720
Gly Ala Gln Gly Pro Ala Gly Pro Gly Gly Ala Gln Gly Pro Ala Gly
                725                 730                 735
Pro Gly Gly Ala His Gly Pro Ala Gly Pro Lys Gly Ala His Gly Pro
            740                 745                 750
Ala Gly Pro Lys Gly Ala His Gly Pro Ala Gly Pro Lys Gly Ala His
        755                 760                 765
Gly Pro Ala Gly Pro Lys Gly Ala Gln Gly Pro Ala Gly Pro Gly Gly
    770                 775                 780
```

```
Ala Gln Gly Pro Ala Gly Pro Gly Gly Ala Gln Gly Pro Ala Gly Pro
785                 790                 795                 800

Gly Gly Ala Gln Gly Pro Ala Gly Pro Gly Gly Ala Gln Gly Pro Ala
                805                 810                 815

Gly Pro Gly Gly Ala Gln Gly Pro Ala Gly Pro Gly Gly Ala Gln Gly
            820                 825                 830

Pro Ala Gly Pro Gly Gly Ala Gln Gly Pro Ala Gly Pro Gly Gly Ala
        835                 840                 845

Gln Gly Pro Ala Gly Pro Gly Gly Ala Gln Gly Pro Ala Gly Pro Gly
    850                 855                 860

Gly Ala Gln Gly Pro Ala Gly Pro Gly Gly Ala Gln Gly Pro Ala Gly
865                 870                 875                 880

Pro Gly Gly Ala Gln Gly Pro Ala Gly Pro Gly Gly Ala Gln Gly Pro
                885                 890                 895

Ala Gly Pro Gly Gly Ala Gln Gly Pro Ala Gly Pro Gly Gly Ala Gln
                900                 905                 910

Gly Pro Ala Gly Pro Gly Gly Ala Gln Gly Pro Ala Gly Pro Gly Gly
            915                 920                 925

Ala Gln Gly Pro Ala Gly Pro Gly Gly Ala Gln Gly Pro Ala Gly Pro
930                 935                 940

Gly Gly Ala Gln Gly Pro Ala Gly Pro Gly Gly Ala Gln Gly Pro Ala
945                 950                 955                 960

Gly Pro Gly Gly Ala Gln Gly Pro Ala Gly Pro Gly Gly Ala Gln Gly
                965                 970                 975

Pro Ala Gly Pro Gly Gly Ala Gln Gly Pro Ala Gly Pro Gly Gly Ala
            980                 985                 990

His Gly Pro Ala Gly Pro Lys Gly Ala His Gly Pro Ala Gly Pro Lys
    995                 1000                1005

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 9

Gly Ala Gln Gly Pro Ala Gly Pro Gly
  1               5

<210> SEQ ID NO 10
<211> LENGTH: 748
<212> TYPE: PRT
<213> ORGANISM: Artificial Sequence
<220> FEATURE:
<223> OTHER INFORMATION: Description of Artificial Sequence: Example
      amino acid sequence

<400> SEQUENCE: 10

Gly Ala Pro Ser Gln Gly Ala Pro Gly Leu Gln Gly Ala Pro Ser Gln
  1               5                  10                  15

Gly Ala Pro Gly Leu Gln Gly Ala Pro Ser Gln Gly Ala Pro Gly Leu
                20                  25                  30

Gln Gly Ala Pro Ser Gln Gly Ala Pro Gly Leu Gln Gly Ala Pro Ser
            35                  40                  45

Gln Gly Ala Pro Gly Leu Gln Gly Ala Pro Ser Gln Gly Ala Pro Gly
        50                  55                  60
```

-continued

```
Leu Gln Gly Ala Pro Ser Gln Gly Ala Pro Gly Leu Gln Gly Ala Pro
 65                  70                  75                  80

Ser Gln Gly Ala Pro Gly Leu Gln Gly Ala Pro Ser Gln Gly Ala Pro
                 85                  90                  95

Gly Leu Gln Gly Ala Pro Ser Gln Gly Ala Pro Gly Leu Gln Gly Ala
            100                 105                 110

Pro Ser Gln Gly Ala Pro Gly Leu Gln Gly Ala Pro Ser Gln Gly Ala
        115                 120                 125

Pro Gly Leu Gln Gly Ala Pro Ser Gln Gly Ala Pro Gly Leu Gln Gly
    130                 135                 140

Ala Pro Ser Gln Gly Ala Pro Gly Leu Gln Gly Ala Pro Ser Gln Gly
145                 150                 155                 160

Ala Pro Gly Leu Gln Gly Ala Pro Ser Gln Gly Ala Pro Gly Leu Gln
                165                 170                 175

Gly Ala Pro Ser Gln Gly Ala Pro Gly Leu Gln Gly Ala Pro Ser Gln
            180                 185                 190

Gly Ala Pro Gly Leu Gln Gly Ala Pro Ser Gln Gly Ala Pro Gly Leu
        195                 200                 205

Gln Gly Ala Pro Ser Gln Gly Ala Pro Gly Leu Gln Gly Ala Pro Ser
    210                 215                 220

Gln Gly Ala Pro Gly Leu Gln Gly Ala Pro Ser Gln Gly Ala Pro Gly
225                 230                 235                 240

Leu Gln Gly Ala Pro Ser Gln Gly Ala Pro Gly Leu Gln Gly Ala Pro
                245                 250                 255

Ser Gln Gly Ala Pro Gly Leu Gln Gly Ala Pro Ser Gln Gly Ala Pro
            260                 265                 270

Gly Leu Gln Gly Ala Pro Ser Gln Gly Ala Pro Gly Leu Gln Gly Ala
        275                 280                 285

Pro Ser Gln Gly Ala Pro Gly Leu Gln Gly Ala Pro Ser Gln Gly Ala
    290                 295                 300

Pro Gly Leu Gln Gly Ala Pro Ser Gln Gly Ala Pro Gly Leu Gln Gly
305                 310                 315                 320

Ala Pro Ser Gln Gly Ala Pro Gly Leu Gln Gly Ala Pro Ser Gln Gly
                325                 330                 335

Ala Pro Gly Leu Gln Gly Ala Pro Ser Gln Gly Ala Pro Gly Leu Gln
            340                 345                 350

Gly Ala Pro Ser Gln Gly Ala Pro Gly Leu Gln Gly Ala Pro Ser Gln
        355                 360                 365

Gly Ala Pro Gly Leu Gln Gly Ala Pro Ser Gln Gly Ala Pro Gly Leu
    370                 375                 380

Gln Gly Ala Pro Ser Gln Gly Ala Pro Gly Leu Gln Gly Ala Pro Ser
385                 390                 395                 400

Gln Gly Ala Pro Gly Leu Gln Gly Ala Pro Ser Gln Gly Ala Pro Gly
                405                 410                 415

Leu Gln Gly Ala Pro Ser Gln Gly Ala Pro Gly Leu Gln Gly Ala Pro
            420                 425                 430

Ser Gln Gly Ala Pro Gly Leu Gln Gly Ala Pro Ser Gln Gly Ala Pro
        435                 440                 445

Gly Leu Gln Gly Ala Pro Ser Gln Gly Ala Pro Gly Leu Gln Gly Ala
    450                 455                 460

Pro Ser Gln Gly Ala Pro Gly Leu Gln Gly Ala Pro Ser Gln Gly Ala
465                 470                 475                 480
```

-continued

```
Pro Gly Leu Gln Gly Ala Pro Ser Gln Gly Ala Pro Gly Leu Gln Gly
                485                 490                 495

Ala Pro Ser Gln Gly Ala Pro Gly Leu Gln Gly Ala Pro Ser Gln Gly
        500                 505                 510

Ala Pro Gly Leu Gln Gly Ala Pro Ser Gln Gly Ala Pro Gly Leu Gln
        515                 520                 525

Gly Ala Pro Ser Gln Gly Ala Pro Gly Leu Gln Gly Ala Pro Ser Gln
        530                 535                 540

Gly Ala Pro Gly Leu Gln Gly Ala Pro Ser Gln Gly Ala Pro Gly Leu
545                 550                 555                 560

Gln Gly Ala Pro Ser Gln Gly Ala Pro Gly Leu Gln Gly Ala Pro Ser
                565                 570                 575

Gln Gly Ala Pro Gly Leu Gln Gly Ala Pro Ser Gln Gly Ala Pro Gly
        580                 585                 590

Leu Gln Gly Ala Pro Ser Gln Gly Ala Pro Gly Leu Gln Gly Ala Pro
        595                 600                 605

Ser Gln Gly Ala Pro Gly Leu Gln Gly Ala Pro Ser Gln Gly Ala Pro
        610                 615                 620

Gly Leu Gln Gly Ala Pro Ser Gln Gly Ala Pro Gly Leu Gln Gly Ala
625                 630                 635                 640

Pro Ser Gln Gly Ala Pro Gly Leu Gln Gly Ala Pro Ser Gln Gly Ala
                645                 650                 655

Pro Gly Leu Gln Gly Ala Pro Ser Gln Gly Ala Pro Gly Leu Gln Gly
        660                 665                 670

Ala Pro Ser Gln Gly Ala Pro Gly Leu Gln Gly Ala Pro Ser Gln Gly
        675                 680                 685

Ala Pro Gly Leu Gln Gly Ala Pro Ser Gln Gly Ala Pro Gly Leu Gln
        690                 695                 700

Gly Ala Pro Ser Gln Gly Ala Pro Gly Leu Gln Gly Ala Pro Ser Gln
705                 710                 715                 720

Gly Ala Pro Gly Leu Gln Gly Ala Pro Ser Gln Gly Ala Pro Gly Leu
                725                 730                 735

Gln Gly Ala Pro Ser Gln Gly Ala Pro Gly Leu Gln
        740                 745

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Example
      amino acid sequence

<400> SEQUENCE: 11

Met Cys His His His Leu Met
 1               5

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Example
      amino acid sequence

<400> SEQUENCE: 12

Gly Pro Ala Gly Glu Arg Gly Pro Lys Gly Trp Met
 1               5                  10
```

```
<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: Formula
      sequence
<221> NAME/KEY: MOD_RES
<222> LOCATION: (3)
<223> OTHER INFORMATION: His or Met
<221> NAME/KEY: MOD_RES
<222> LOCATION: (6)
<223> OTHER INFORMATION: His or Met

<400> SEQUENCE: 13

Gly Pro Xaa Gly Leu Xaa Gly Pro Arg Gly Pro Pro Gly Ala Ser Gly
  1               5                  10                  15

Ala Pro Gly Phe Gln Gly
            20

<210> SEQ ID NO 14
<211> LENGTH: 4
<212> TYPE: PRT
<213> ORGANISM: Murine sp.

<400> SEQUENCE: 14

Met Gly Pro Arg
  1

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Example
      amino acid sequence
<221> NAME/KEY: MOD_RES
<222> LOCATION: (1)..(4)
<223> OTHER INFORMATION: At least one amino acid is amended
<221> NAME/KEY: MOD_RES
<222> LOCATION: (5)
<223> OTHER INFORMATION: Gly or other amino acid
<221> NAME/KEY: MOD_RES
<222> LOCATION: (6)
<223> OTHER INFORMATION: Pro or other amino acid

<400> SEQUENCE: 15

Leu Ile Val Met Xaa Xaa Arg
  1               5

<210> SEQ ID NO 16
<211> LENGTH: 4
<212> TYPE: PRT
<213> ORGANISM: Murine sp.

<400> SEQUENCE: 16

Arg Gly Pro Met
  1

<210> SEQ ID NO 17
<211> LENGTH: 9
<212> TYPE: PRT
<213> ORGANISM: Murine sp.
<220> FEATURE:
<221> NAME/KEY: MOD_RES
<222> LOCATION: (5)..(6)
<223> OTHER INFORMATION: any amino acid
```

```
<400> SEQUENCE: 17

Met Leu Ile Val Xaa Xaa Arg Lys His
 1               5

<210> SEQ ID NO 18
<211> LENGTH: 4
<212> TYPE: PRT
<213> ORGANISM: Murine sp.

<400> SEQUENCE: 18

Met Lys Gly His
 1

<210> SEQ ID NO 19
<211> LENGTH: 4
<212> TYPE: PRT
<213> ORGANISM: Murine sp.

<400> SEQUENCE: 19

Val Gly Ala Lys
 1

<210> SEQ ID NO 20
<211> LENGTH: 4
<212> TYPE: PRT
<213> ORGANISM: Murine sp.

<400> SEQUENCE: 20

Ile Lys Gly His
 1

<210> SEQ ID NO 21
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 21
gagcctggcg gttcaggtcc acgaggtcca atgggtcccc ctgg            44

<210> SEQ ID NO 22
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 22 ccaggggggac ccattggacc tcgtggacct gaaccgccag gctc           44

<210> SEQ ID NO 23
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 23
ggagctcctg gccagcgagg tccaatgggt ctgcccggtg agag            44

<210> SEQ ID NO 24
<211> LENGTH: 44
<212> TYPE: DNA
<213> ORGANISM: Artificial Sequence
```

-continued

```
<220> FEATURE:
<223> OTHER INFORMATION: Description of Artificial Sequence: Primer

<400> SEQUENCE: 24
ctctcaccgg gcagacccat tggacctcgc tggccaggag ctcc                44

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 25
gcgctcgaga aaagagaggc tgaagc                                    26

<210> SEQ ID NO 26
<211> LENGTH: 108
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 26
gcgctcgaga aaagagaggc tgaagctggt ccacccggtg agccaggtaa cccaggatct    60
cctggtaacc aaggacagcc cggtaacaag ggttctccag gtaatcca              108

<210> SEQ ID NO 27
<211> LENGTH: 110
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 27
tgagaacctt gtggaccgtt ggaacctggc tcaccaggtt gtccgttctg accaggttga    60
ccaggttgac cttcgtttcc tggttgacct ggattacctg gagaacccctt             110

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 28
tgagaacctt gtggaccgtt ggaa                                       24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 29
ttccaacggt ccacaaggtt ctca                                       24

<210> SEQ ID NO 30
<211> LENGTH: 115
```

-continued

```
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 30
ttccaacggt ccacaaggtt ctcagggtaa ccctggaaag aatggtcaac ctggatcccc    60
aggttcacaa ggctctccag gtaaccaagg ttccctggt cagccaggta accct         115

<210> SEQ ID NO 31
<211> LENGTH: 108
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 31
gcgtctgcag tacgaattct attagccacc ggctggaccc tggtttcctg gtttaccttg    60
ttcacctggt tgaccagggt tacctggctg accaggggaa ccttggtt               108

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 32
gcgtctgcag tacgaattct attagc                                         26

<210> SEQ ID NO 33
<211> LENGTH: 104
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 33

Gly Pro Pro Gly Glu Pro Gly Asn Pro Gly Ser Pro Gly Asn Gln Gly
  1               5                  10                  15

Gln Pro Gly Asn Lys Gly Ser Pro Gly Asn Pro Gly Gln Pro Gly Asn
                 20                  25                  30

Glu Gly Gln Pro Gly Gln Pro Gly Gln Asn Gly Gln Pro Gly Glu Pro
             35                  40                  45

Gly Ser Asn Gly Pro Gln Gly Ser Gln Gly Asn Pro Gly Lys Asn Gly
         50                  55                  60

Gln Pro Gly Ser Pro Gly Ser Gln Gly Ser Pro Gly Asn Gln Gly Ser
 65                  70                  75                  80

Pro Gly Gln Pro Gly Asn Pro Gly Gln Pro Gly Glu Gln Gly Lys Pro
                 85                  90                  95

Gly Asn Gln Gly Pro Ala Gly Gly
                100

<210> SEQ ID NO 34
<211> LENGTH: 401
<212> TYPE: PRT
```

<213> ORGANISM: Artificial Sequence
<220> FEATURE:
<223> OTHER INFORMATION: Description of Artificial Sequence: Synthetic amino acid sequence

<400> SEQUENCE: 34

```
Gly Pro Pro Gly Glu Pro Gly Asn Pro Gly Ser Pro Gly Asn Gln Gly
  1               5                  10                  15

Gln Pro Gly Asn Lys Gly Ser Pro Gly Asn Pro Gly Gln Pro Gly Asn
             20                  25                  30

Glu Gly Gln Pro Gly Gln Pro Gly Gln Asn Gly Gln Pro Gly Glu Pro
         35                  40                  45

Gly Ser Asn Gly Pro Gln Gly Ser Gln Gly Asn Pro Gly Lys Asn Gly
     50                  55                  60

Gln Pro Gly Ser Pro Gly Ser Gln Gly Ser Pro Gly Asn Gln Gly Ser
 65                  70                  75                  80

Pro Gly Gln Pro Gly Asn Pro Gly Gln Pro Gly Glu Gln Gly Lys Pro
                 85                  90                  95

Gly Asn Gln Gly Pro Ala Gly Glu Pro Gly Asn Pro Gly Ser Pro Gly
                100                 105                 110

Asn Gln Gly Gln Pro Gly Asn Lys Gly Ser Pro Gly Asn Pro Gly Gln
            115                 120                 125

Pro Gly Asn Glu Gly Gln Pro Gly Gln Pro Gly Gln Asn Gly Gln Pro
        130                 135                 140

Gly Glu Pro Gly Ser Asn Gly Pro Gln Gly Ser Gln Gly Asn Pro Gly
145                 150                 155                 160

Lys Asn Gly Gln Pro Gly Ser Pro Gly Ser Gln Gly Ser Pro Gly Asn
                165                 170                 175

Gln Gly Ser Pro Gly Gln Pro Gly Asn Pro Gly Gln Pro Gly Glu Gln
            180                 185                 190

Gly Lys Pro Gly Asn Gln Gly Pro Ala Gly Glu Pro Gly Asn Pro Gly
        195                 200                 205

Ser Pro Gly Asn Gln Gly Gln Pro Gly Asn Lys Gly Ser Pro Gly Asn
    210                 215                 220

Pro Gly Gln Pro Gly Asn Glu Gly Gln Pro Gly Gln Pro Gly Gln Asn
225                 230                 235                 240

Gly Gln Pro Gly Glu Pro Gly Ser Asn Gly Pro Gln Gly Ser Gln Gly
                245                 250                 255

Asn Pro Gly Lys Asn Gly Gln Pro Gly Ser Pro Gly Ser Gln Gly Ser
            260                 265                 270

Pro Gly Asn Gln Gly Ser Pro Gly Gln Pro Gly Asn Pro Gly Gln Pro
        275                 280                 285

Gly Glu Gln Gly Lys Pro Gly Asn Gln Gly Pro Ala Gly Glu Pro Gly
    290                 295                 300

Asn Pro Gly Ser Pro Gly Asn Gln Gly Gln Pro Gly Asn Lys Gly Ser
305                 310                 315                 320

Pro Gly Asn Pro Gly Gln Pro Gly Asn Glu Gly Gln Pro Gly Gln Pro
                325                 330                 335

Gly Gln Asn Gly Gln Pro Gly Glu Pro Gly Ser Asn Gly Pro Gln Gly
            340                 345                 350

Ser Gln Gly Asn Pro Gly Lys Asn Gly Gln Pro Gly Ser Pro Gly Ser
        355                 360                 365

Gln Gly Ser Pro Gly Asn Gln Gly Ser Pro Gly Gln Pro Gly Asn Pro
    370                 375                 380
```

```
Gly Gln Pro Gly Glu Gln Gly Lys Pro Gly Asn Gln Gly Pro Ala Gly
385                 390                 395                 400

Gly

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 35
gactggttcc aattgacaag c                                           21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 36
gcaaatggca ttctgacatc c                                           21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 37
tactattgcc agcattgctg c                                           21

<210> SEQ ID NO 38
<211> LENGTH: 228
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 38

Tyr Gly Asn Ser Gly Ser Pro Gly Asn Pro Gly Val Ala Gly Pro Lys
 1               5                  10                  15

Gly Asp Ala Gly Gln Pro Gly Glu Lys Gly Pro Pro Gly Ala Gln Gly
            20                  25                  30

Pro Pro Gly Ser Pro Gly Pro Leu Gly Ile Ala Gly Leu Thr Gly Ala
        35                  40                  45

Arg Gly Leu Ala Gly Pro Pro Gly Met Pro Gly Pro Arg Gly Ser Pro
     50                  55                  60

Gly Pro Gln Gly Ile Lys Gly Glu Ser Gly Lys Pro Gly Ala Ser Gly
 65                  70                  75                  80

His Asn Gly Glu Arg Gly Pro Pro Gly Pro Gln Gly Leu Pro Gly Gln
                85                  90                  95

Pro Gly Thr Ala Gly Glu Pro Gly Arg Asp Gly Asn Pro Gly Ser Asp
            100                 105                 110

Gly Gln Pro Gly Arg Asp Gly Ser Pro Gly Gly Lys Gly Asp Arg Gly
        115                 120                 125

Glu Asn Gly Ser Pro Gly Ala Pro Gly Ala Pro Gly His Pro Gly Pro
    130                 135                 140
```

-continued

```
Pro Gly Pro Val Gly Pro Ser Gly Lys Asn Gly Asp Arg Gly Glu Thr
145                 150                 155                 160

Gly Pro Ala Gly Pro Ser Gly Ala Pro Gly Pro Ala Gly Ala Arg Gly
                165                 170                 175

Ala Pro Gly Pro Gln Gly Pro Arg Gly Asp Lys Gly Glu Arg Gly Glu
            180                 185                 190

Thr Gly Ser Asn Gly Ile Lys Gly His Arg Gly Phe Pro Gly Asn Pro
        195                 200                 205

Gly Pro Pro Gly Ser Pro Gly Ala Ala Gly His Gln Gly Ala Val Gly
    210                 215                 220

Ser Pro Gly Pro
225
```

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 39
cttcccagat gtcctatggc tatgatg         27

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 40
ccgctcgagg cgctcgccag gaggtccagg cag         33

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 41
gcgctcgagg ggaggaccaa tgggaccagt cag         33

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 42
gcgctcgagg ccaggagaac caggaggacc ctg         33

<210> SEQ ID NO 43
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 43
tcgaaaagag agaggctgaa gctcccatgg gataactcga gtagg         45

```
<210> SEQ ID NO 44
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 44
aattcctact cgagttatcc catgggagct tcagcctctc tcttt          45

<210> SEQ ID NO 45
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 45
tcgaaaagag agaggctgaa gctcccatgg gataactcga gtagg          45

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 46
aattcctact cgagttatcc catgggagct tcagcctctc tcttt          45

<210> SEQ ID NO 47
<211> LENGTH: 310
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 47
```

Pro Met Gly Pro Ser Gly Pro Arg Gly Leu Pro Gly Pro Pro Gly Ala
 1               5                  10                  15

Pro Gly Pro Gln Gly Phe Gln Gly Pro Pro Gly Glu Pro Gly Glu Pro
            20                  25                  30

Gly Gly Ser Gly Pro Met Gly Pro Arg Gly Pro Pro Gly Pro Pro Gly
        35                  40                  45

Lys Asn Gly Asp Asp Gly Glu Ala Gly Lys Pro Gly Arg Pro Gly Glu
    50                  55                  60

Arg Gly Pro Pro Gly Pro Gln Gly Ala Arg Gly Leu Pro Gly Thr Ala
65                  70                  75                  80

Gly Leu Pro Gly Met Lys Gly His Arg Gly Phe Ser Gly Leu Asp Gly
                85                  90                  95

Ala Lys Gly Asp Ala Gly Pro Ala Gly Pro Lys Gly Glu Pro Gly Ser
           100                 105                 110

Pro Gly Glu Asn Gly Ala Pro Gly Gln Met Gly Pro Arg Gly Leu Pro
       115                 120                 125

Gly Glu Arg Gly Arg Pro Gly Pro Pro Gly Thr Ala Gly Ala Arg Gly
   130                 135                 140

Asn Asp Gly Ala Val Gly Ala Ala Gly Pro Pro Gly Pro Thr Gly Pro
145                 150                 155                 160

Thr Gly Pro Pro Gly Phe Pro Gly Ala Val Gly Ala Lys Gly Glu Ala
                165                 170                 175

```
Gly Pro Gln Gly Ala Arg Gly Ser Glu Gly Pro Gln Gly Val Arg Gly
            180                 185                 190

Glu Pro Gly Pro Pro Gly Pro Ala Gly Ala Ala Gly Pro Ala Gly Asn
            195                 200                 205

Pro Gly Ala Asp Gly Gln Pro Gly Ala Lys Gly Ala Asn Gly Ala Pro
210                 215                 220

Gly Ile Ala Gly Ala Pro Gly Phe Pro Gly Ala Arg Gly Pro Ser Gly
225                 230                 235                 240

Pro Gln Gly Pro Ser Gly Pro Pro Gly Pro Lys Gly Asn Ser Gly Glu
            245                 250                 255

Pro Gly Ala Pro Gly Asn Lys Gly Asp Thr Gly Ala Lys Gly Glu Pro
            260                 265                 270

Gly Ala Thr Gly Val Gln Gly Pro Pro Gly Pro Ala Gly Glu Glu Gly
            275                 280                 285

Lys Arg Gly Ala Arg Gly Glu Pro Gly Pro Ser Gly Leu Pro Gly Pro
            290                 295                 300

Pro Gly Glu Arg Leu Glu
305                 310

<210> SEQ ID NO 48
<211> LENGTH: 595
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 48

Pro Met Gly Pro Ser Gly Pro Arg Gly Leu Pro Gly Pro Pro Gly Ala
  1               5                  10                  15

Pro Gly Pro Gln Gly Phe Gln Gly Pro Pro Gly Glu Pro Gly Glu Pro
             20                  25                  30

Gly Gly Ser Gly Pro Met Gly Pro Arg Gly Pro Pro Gly Pro Pro Gly
             35                  40                  45

Lys Asn Gly Asp Asp Gly Glu Ala Gly Lys Pro Gly Arg Pro Gly Glu
 50                  55                  60

Arg Gly Pro Pro Gly Pro Gln Gly Ala Arg Gly Leu Pro Gly Thr Ala
 65                  70                  75                  80

Gly Leu Pro Gly Met Lys Gly His Arg Gly Phe Ser Gly Leu Asp Gly
             85                  90                  95

Ala Lys Gly Asp Ala Gly Pro Ala Gly Pro Lys Gly Glu Pro Gly Ser
            100                 105                 110

Pro Gly Glu Asn Gly Ala Pro Gly Gln Met Gly Pro Arg Gly Leu Pro
            115                 120                 125

Gly Glu Arg Gly Arg Pro Gly Pro Pro Gly Thr Ala Gly Ala Arg Gly
            130                 135                 140

Asn Asp Gly Ala Val Gly Ala Ala Gly Pro Pro Gly Pro Thr Gly Pro
145                 150                 155                 160

Thr Gly Pro Pro Gly Phe Pro Gly Ala Val Gly Ala Lys Gly Glu Ala
                165                 170                 175

Gly Pro Gln Gly Ala Arg Gly Ser Glu Gly Pro Gln Gly Val Arg Gly
            180                 185                 190

Glu Pro Gly Pro Pro Gly Pro Ala Gly Ala Ala Gly Pro Ala Gly Asn
            195                 200                 205

Pro Gly Ala Asp Gly Gln Pro Gly Ala Lys Gly Ala Asn Gly Ala Pro
210                 215                 220
```

-continued

```
Gly Ile Ala Gly Ala Pro Gly Phe Pro Gly Ala Arg Gly Pro Ser Gly
225                 230                 235                 240

Pro Gln Gly Pro Ser Gly Pro Pro Gly Pro Lys Gly Asn Ser Gly Glu
            245                 250                 255

Pro Gly Ala Pro Gly Asn Lys Gly Asp Thr Gly Ala Lys Gly Glu Pro
            260                 265                 270

Gly Ala Thr Gly Val Gln Gly Pro Pro Gly Pro Ala Gly Glu Glu Gly
            275                 280                 285

Lys Arg Gly Ala Arg Gly Glu Pro Gly Pro Ser Gly Leu Pro Gly Pro
290                 295                 300

Pro Gly Glu Arg Gly Gly Pro Gly Ser Arg Gly Phe Pro Gly Ala Asp
305                 310                 315                 320

Gly Val Ala Gly Pro Lys Gly Pro Ser Gly Glu Arg Gly Ala Pro Gly
            325                 330                 335

Pro Ala Gly Pro Lys Gly Ser Pro Gly Glu Ala Gly Arg Pro Gly Glu
            340                 345                 350

Ala Gly Leu Pro Gly Ala Lys Gly Leu Thr Gly Ser Pro Gly Ser Pro
            355                 360                 365

Gly Pro Asp Gly Lys Thr Gly Pro Pro Gly Pro Ala Gly Gln Asp Gly
            370                 375                 380

Arg Pro Gly Pro Ala Gly Pro Pro Gly Ala Arg Gly Gln Ala Gly Val
385                 390                 395                 400

Met Gly Phe Pro Gly Pro Lys Gly Thr Ala Gly Glu Pro Gly Lys Ala
            405                 410                 415

Gly Glu Arg Gly Leu Pro Gly Pro Pro Gly Ala Val Gly Pro Ala Gly
            420                 425                 430

Lys Asp Gly Glu Ala Gly Ala Gln Gly Ala Pro Gly Pro Ala Gly Pro
            435                 440                 445

Ala Gly Glu Arg Gly Glu Gln Gly Pro Ala Gly Ser Pro Gly Phe Gln
            450                 455                 460

Gly Leu Pro Gly Pro Ala Gly Pro Pro Gly Glu Ala Gly Lys Pro Gly
465                 470                 475                 480

Glu Gln Gly Val Pro Gly Asp Leu Gly Ala Pro Gly Pro Ser Gly Ala
            485                 490                 495

Arg Gly Glu Arg Gly Phe Pro Gly Glu Arg Gly Val Gln Gly Pro Pro
            500                 505                 510

Gly Pro Ala Gly Pro Arg Gly Asn Asn Gly Ala Pro Gly Asn Asp Gly
            515                 520                 525

Ala Lys Gly Asp Thr Gly Ala Pro Gly Ala Pro Gly Ser Gln Gly Ala
            530                 535                 540

Pro Gly Leu Gln Gly Met Pro Gly Glu Arg Gly Ala Ala Gly Leu Pro
545                 550                 555                 560

Gly Pro Lys Gly Asp Arg Gly Asp Ala Gly Pro Lys Gly Ala Asp Gly
            565                 570                 575

Ser Pro Gly Lys Asp Gly Ala Arg Gly Leu Thr Gly Pro Ile Gly Pro
            580                 585                 590

Pro Leu Glu
            595

<210> SEQ ID NO 49
<211> LENGTH: 822
<212> TYPE: PRT
```

<213> ORGANISM: Artificial Sequence
<220> FEATURE:
<223> OTHER INFORMATION: Description of Artificial Sequence: Synthetic amino acid sequence

<400> SEQUENCE: 49

```
Pro Met Gly Pro Ser Gly Pro Arg Gly Leu Pro Gly Pro Pro Gly Ala
 1               5                  10                  15
Pro Gly Pro Gln Gly Phe Gln Gly Pro Pro Gly Glu Pro Gly Glu Pro
            20                  25                  30
Gly Gly Ser Gly Pro Met Gly Pro Arg Gly Pro Pro Gly Pro Pro Gly
        35                  40                  45
Lys Asn Gly Asp Asp Gly Glu Ala Gly Lys Pro Gly Arg Pro Gly Glu
    50                  55                  60
Arg Gly Pro Pro Gly Pro Gln Gly Ala Arg Gly Leu Pro Gly Thr Ala
65                  70                  75                  80
Gly Leu Pro Gly Met Lys Gly His Arg Gly Phe Ser Gly Leu Asp Gly
                85                  90                  95
Ala Lys Gly Asp Ala Gly Pro Ala Gly Pro Lys Gly Glu Pro Gly Ser
            100                 105                 110
Pro Gly Glu Asn Gly Ala Pro Gly Gln Met Gly Pro Arg Gly Leu Pro
        115                 120                 125
Gly Glu Arg Gly Arg Pro Gly Pro Pro Gly Thr Ala Gly Ala Arg Gly
    130                 135                 140
Asn Asp Gly Ala Val Gly Ala Ala Gly Pro Pro Gly Pro Thr Gly Pro
145                 150                 155                 160
Thr Gly Pro Pro Gly Phe Pro Gly Ala Val Gly Ala Lys Gly Glu Ala
                165                 170                 175
Gly Pro Gln Gly Ala Arg Gly Ser Glu Gly Pro Gln Gly Val Arg Gly
            180                 185                 190
Glu Pro Gly Pro Pro Gly Pro Ala Gly Ala Ala Gly Pro Ala Gly Asn
        195                 200                 205
Pro Gly Ala Asp Gly Gln Pro Gly Ala Lys Gly Ala Asn Gly Ala Pro
    210                 215                 220
Gly Ile Ala Gly Ala Pro Gly Phe Pro Gly Ala Arg Gly Pro Ser Gly
225                 230                 235                 240
Pro Gln Gly Pro Ser Gly Pro Pro Gly Pro Lys Gly Asn Ser Gly Glu
                245                 250                 255
Pro Gly Ala Pro Gly Asn Lys Gly Asp Thr Gly Ala Lys Gly Glu Pro
            260                 265                 270
Gly Ala Thr Gly Val Gln Gly Pro Pro Gly Pro Ala Gly Glu Glu Gly
        275                 280                 285
Lys Arg Gly Ala Arg Gly Glu Pro Gly Pro Ser Gly Leu Pro Gly Pro
    290                 295                 300
Pro Gly Glu Arg Gly Gly Pro Gly Ser Arg Gly Phe Pro Gly Ala Asp
305                 310                 315                 320
Gly Val Ala Gly Pro Lys Gly Pro Ser Gly Glu Arg Gly Ala Pro Gly
                325                 330                 335
Pro Ala Gly Pro Lys Gly Ser Pro Gly Glu Ala Gly Arg Pro Gly Glu
            340                 345                 350
Ala Gly Leu Pro Gly Ala Lys Gly Leu Thr Gly Ser Pro Gly Ser Pro
        355                 360                 365
Gly Pro Asp Gly Lys Thr Gly Pro Pro Gly Pro Ala Gly Gln Asp Gly
    370                 375                 380
```

-continued

```
Arg Pro Gly Pro Ala Gly Pro Gly Ala Arg Gly Gln Ala Gly Val
385                 390                 395                 400

Met Gly Phe Pro Gly Pro Lys Gly Thr Ala Gly Glu Pro Gly Lys Ala
            405                 410                 415

Gly Glu Arg Gly Leu Pro Gly Pro Pro Gly Ala Val Gly Pro Ala Gly
            420                 425                 430

Lys Asp Gly Glu Ala Gly Ala Gln Gly Ala Pro Gly Pro Ala Gly Pro
            435                 440                 445

Ala Gly Glu Arg Gly Glu Gln Gly Pro Ala Gly Ser Pro Gly Phe Gln
            450                 455                 460

Gly Leu Pro Gly Pro Ala Gly Pro Pro Gly Glu Ala Gly Lys Pro Gly
465                 470                 475                 480

Glu Gln Gly Val Pro Gly Asp Leu Gly Ala Pro Gly Pro Ser Gly Ala
                485                 490                 495

Arg Gly Glu Arg Gly Phe Pro Gly Glu Arg Gly Val Gln Gly Pro Pro
            500                 505                 510

Gly Pro Ala Gly Pro Arg Gly Asn Asn Gly Ala Pro Gly Asn Asp Gly
            515                 520                 525

Ala Lys Gly Asp Thr Gly Ala Pro Gly Ala Pro Gly Ser Gln Gly Ala
            530                 535                 540

Pro Gly Leu Gln Gly Met Pro Gly Glu Arg Gly Ala Ala Gly Leu Pro
545                 550                 555                 560

Gly Pro Lys Gly Asp Arg Gly Asp Ala Gly Pro Lys Gly Ala Asp Gly
            565                 570                 575

Ser Pro Gly Lys Asp Gly Ala Arg Gly Leu Thr Gly Pro Ile Gly Pro
            580                 585                 590

Pro Gly Pro Ala Gly Ala Pro Gly Asp Lys Gly Glu Ala Gly Pro Ser
            595                 600                 605

Gly Pro Pro Gly Pro Thr Gly Ala Arg Gly Ala Pro Gly Asp Arg Gly
            610                 615                 620

Glu Ala Gly Pro Pro Gly Pro Ala Gly Phe Ala Gly Pro Pro Gly Ala
625                 630                 635                 640

Asp Gly Gln Pro Gly Ala Lys Gly Glu Pro Gly Asp Thr Gly Val Lys
            645                 650                 655

Gly Asp Ala Gly Pro Pro Gly Pro Ala Gly Pro Ala Gly Pro Pro Gly
            660                 665                 670

Pro Ile Gly Asn Val Gly Ala Pro Gly Pro Lys Gly Pro Arg Gly Ala
            675                 680                 685

Ala Gly Pro Pro Gly Ala Thr Gly Phe Pro Gly Ala Ala Gly Arg Val
            690                 695                 700

Gly Pro Pro Gly Pro Ser Gly Asn Ala Gly Pro Pro Gly Pro Pro Gly
705                 710                 715                 720

Pro Val Gly Lys Glu Gly Lys Gly Pro Arg Gly Glu Thr Gly Pro
            725                 730                 735

Ala Gly Arg Pro Gly Glu Val Gly Pro Pro Gly Pro Pro Gly Pro Ala
            740                 745                 750

Gly Glu Lys Gly Ser Pro Gly Ala Asp Gly Pro Ala Gly Ser Pro Gly
            755                 760                 765

Thr Pro Gly Pro Gln Gly Ile Ala Gly Gln Arg Gly Val Val Gly Leu
            770                 775                 780

Pro Gly Gln Arg Gly Glu Arg Gly Phe Pro Gly Leu Pro Gly Pro Ser
785                 790                 795                 800
```

```
Gly Glu Pro Gly Lys Gln Gly Pro Ser Gly Ser Ser Gly Glu Arg Gly
                805                 810                 815

Pro Pro Gly Pro Met Gly
            820

<210> SEQ ID NO 50
<211> LENGTH: 595
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 50

Pro Met Gly Pro Ser Gly Pro Arg Gly Leu Pro Gly Pro Pro Gly Ala
  1               5                  10                  15

Pro Gly Pro Gln Gly Phe Gln Gly Pro Pro Gly Glu Pro Gly Glu Pro
                 20                  25                  30

Gly Gly Ser Gly Pro Met Gly Pro Arg Gly Pro Pro Gly Pro Pro Gly
             35                  40                  45

Lys Asn Gly Asp Asp Gly Glu Ala Gly Lys Pro Gly Arg Pro Gly Glu
 50                  55                  60

Arg Gly Pro Pro Gly Pro Gln Gly Ala Arg Gly Leu Pro Gly Thr Ala
 65                  70                  75                  80

Gly Leu Pro Gly Met Lys Gly His Arg Gly Phe Ser Gly Leu Asp Gly
                 85                  90                  95

Ala Lys Gly Asp Ala Gly Pro Ala Gly Pro Lys Gly Glu Pro Gly Ser
                100                 105                 110

Pro Gly Glu Asn Gly Ala Pro Gly Gln Met Gly Pro Arg Gly Leu Pro
            115                 120                 125

Gly Glu Arg Gly Arg Pro Gly Pro Pro Gly Thr Ala Gly Ala Arg Gly
        130                 135                 140

Asn Asp Gly Ala Val Gly Ala Ala Gly Pro Pro Gly Pro Thr Gly Pro
145                 150                 155                 160

Thr Gly Pro Pro Gly Phe Pro Gly Ala Val Gly Ala Lys Gly Glu Ala
                165                 170                 175

Gly Pro Gln Gly Ala Arg Gly Ser Glu Gly Pro Gln Gly Val Arg Gly
            180                 185                 190

Glu Pro Gly Pro Pro Gly Pro Ala Gly Ala Ala Gly Pro Ala Gly Asn
        195                 200                 205

Pro Gly Ala Asp Gly Gln Pro Gly Ala Lys Gly Ala Asn Gly Ala Pro
    210                 215                 220

Gly Ile Ala Gly Ala Pro Gly Phe Pro Gly Ala Arg Gly Pro Ser Gly
225                 230                 235                 240

Pro Gln Gly Pro Ser Gly Pro Pro Gly Pro Lys Gly Asn Ser Gly Glu
                245                 250                 255

Pro Gly Ala Pro Gly Asn Lys Gly Asp Thr Gly Ala Lys Gly Glu Pro
            260                 265                 270

Gly Ala Thr Gly Val Gln Gly Pro Pro Gly Pro Ala Gly Glu Glu Gly
        275                 280                 285

Lys Arg Gly Ala Arg Gly Glu Pro Gly Pro Ser Gly Leu Pro Gly Pro
    290                 295                 300

Pro Gly Glu Arg Gly Gly Pro Gly Ser Arg Gly Phe Pro Gly Ala Asp
305                 310                 315                 320

Gly Val Ala Gly Pro Lys Gly Pro Ser Gly Glu Arg Gly Ala Pro Gly
                325                 330                 335
```

-continued

```
Pro Ala Gly Pro Lys Gly Ser Pro Gly Glu Ala Gly Arg Pro Gly Glu
            340                 345                 350
Ala Gly Leu Pro Gly Ala Lys Gly Leu Thr Gly Ser Pro Gly Ser Pro
            355                 360                 365
Gly Pro Asp Gly Lys Thr Gly Pro Pro Gly Pro Ala Gly Gln Asp Gly
    370                 375                 380
Arg Pro Gly Pro Ala Gly Pro Pro Gly Ala Arg Gly Gln Ala Gly Val
385                 390                 395                 400
Met Gly Phe Pro Gly Pro Lys Gly Thr Ala Gly Glu Pro Gly Lys Ala
            405                 410                 415
Gly Glu Arg Gly Leu Pro Gly Pro Gly Ala Val Gly Pro Ala Gly
            420                 425                 430
Lys Asp Gly Glu Ala Gly Ala Gln Gly Ala Pro Gly Pro Ala Gly Pro
            435                 440                 445
Ala Gly Glu Arg Gly Glu Gln Gly Pro Ala Gly Ser Pro Gly Phe Gln
    450                 455                 460
Gly Leu Pro Gly Pro Ala Gly Pro Pro Gly Glu Ala Gly Lys Pro Gly
465                 470                 475                 480
Glu Gln Gly Val Pro Gly Asp Leu Gly Ala Pro Gly Pro Ser Gly Ala
            485                 490                 495
Arg Gly Glu Arg Gly Phe Pro Gly Glu Arg Gly Val Gln Gly Pro Pro
            500                 505                 510
Gly Pro Ala Gly Pro Arg Gly Asn Asn Gly Ala Pro Gly Asn Asp Gly
            515                 520                 525
Ala Lys Gly Asp Thr Gly Ala Pro Gly Ala Pro Gly Ser Gln Gly Ala
            530                 535                 540
Pro Gly Leu Gln Gly Met Pro Gly Glu Arg Gly Ala Ala Gly Leu Pro
545                 550                 555                 560
Gly Pro Lys Gly Asp Arg Gly Asp Ala Gly Pro Lys Gly Ala Asp Gly
            565                 570                 575
Ser Pro Gly Lys Asp Gly Ala Arg Gly Leu Thr Gly Pro Ile Gly Pro
            580                 585                 590
Pro Leu Glu
        595
```